(12) United States Patent
Gravenfors et al.

(10) Patent No.: US 8,163,928 B2
(45) Date of Patent: Apr. 24, 2012

(54) HETEROARYL SUBSTITUTED BENZOTHIAZOLES

(75) Inventors: Ylva Gravenfors, Sodertalje (SE); Catrin Jonasson, Sodertalje (SE); Jonas Malmstrom, Sodertalje (SE); Gunnar Nordvall, Sodertalje (SE); David Pyring, Sodertalje (SE); Can Slivo, Sodertalje (SE); Daniel Sohn, Sodertalje (SE); Peter Strom, Sodertalje (SE); David Wensbo, Lund (SE)

(73) Assignee: AstraZeneca AB, Sodertalje (SE)

( * ) Notice: Subject to any disclaimer, the term of this patent is extended or adjusted under 35 U.S.C. 154(b) by 611 days.

(21) Appl. No.: 12/162,255

(22) PCT Filed: Jan. 25, 2007

(86) PCT No.: PCT/SE2007/000068
§ 371 (c)(1),
(2), (4) Date: Jul. 25, 2008

(87) PCT Pub. No.: WO2007/086800
PCT Pub. Date: Aug. 2, 2007

(65) Prior Publication Data
US 2009/0028787 A1 Jan. 29, 2009

Related U.S. Application Data

(60) Provisional application No. 60/762,654, filed on Jan. 27, 2006.

(51) Int. Cl.
*A61K 51/00* (2006.01)
*A61K 51/04* (2006.01)
(52) U.S. Cl. ..... 546/270.1; 546/14; 424/1.81; 424/1.85; 424/1.89; 514/338
(58) Field of Classification Search .............. 546/270.1
See application file for complete search history.

(56) References Cited

U.S. PATENT DOCUMENTS

| | | | |
|---|---|---|---|
| 4,232,010 A | 11/1980 | Tsukamoto et al. | |
| 5,236,619 A | 8/1993 | Iwaki et al. | |
| 5,518,713 A | 5/1996 | Raspanti | |
| 2005/0101647 A1 | 5/2005 | Oda et al. | |
| 2007/0258887 A1 | 11/2007 | Tamagnan et al. | |
| 2008/0027051 A1 | 1/2008 | Malmstrom et al. | |

FOREIGN PATENT DOCUMENTS

| | | |
|---|---|---|
| EP | 120589 B1 | 6/1988 |
| EP | 1612204 A1 | 1/2006 |
| JP | 2004250411 A | 9/2004 |
| JP | 11116476 A | 5/2008 |
| WO | 9517095 A1 | 6/1995 |
| WO | 0216333 A2 | 2/2002 |
| WO | 02051821 A1 | 7/2002 |
| WO | 02085903 A2 | 10/2002 |
| WO | 02092086 A1 | 11/2002 |
| WO | 03051859 A1 | 6/2003 |
| WO | 03106439 A1 | 12/2003 |
| WO | 2004008319 A2 | 1/2004 |
| WO | 2004012736 A1 | 2/2004 |
| WO | 2004083195 A1 | 9/2004 |
| WO | 2004101558 A1 | 11/2004 |
| WO | 2006030032 A1 | 3/2006 |
| WO | 2006125324 A1 | 11/2006 |
| WO | 2007033080 A2 | 3/2007 |
| WO | 2007035405 A2 | 3/2007 |
| WO | 2007047204 A1 | 4/2007 |
| WO | 2007/070173 | 6/2007 |
| WO | 2007063946 A1 | 6/2007 |
| WO | 2007/086800 | 8/2007 |
| WO | 2007149030 A1 | 12/2007 |
| WO | 2008091195 A1 | 7/2008 |

OTHER PUBLICATIONS

Bastic et al., Chemical Abstract 62:74175, 1965.*
Allsop et al., "3-p-Toluoyl-2-[4'-(3-diethylaminopropoxy)-phenyl]-benzofuran and 2-[4'-(3-Diethylaminopropoxy)-phenyl]-benzofuran Do Not Act as Surfactants or Micelles when Inhibiting the Aggregation of B-Amyloid Peptide", Bioorg. Med.Chem.Lett, 2001, 255-257, 11(2).
Barni, et al., "2-(Methylpyridyl or quinoly)benz-X-azoles, Salts and Polymethine Dyes (1)", Journal of Heterocyclic Chemistry, 1979, p. 1579-82, 16(8).
Cai et al., "Synthesis an Evaluation of Two 18F-Labeled 6-Iodo (4-N,N-dimethylamino)phenylimidazo [1,2-a] pyridine Derivatives as Prospective Radioligands for B-Amyloid in Alzheimer's Disease", J.Med.Chem, 2004, 2208-2218, 47(9).
Chang et al., "Synthesis and evaluation of benzothiophene derivatives as ligands for imagining B-amyloid plaques in Alzheimer's disease", Nuclear Medicine and Biology, 2006, 811-820, 33.
Choi at al., "Synthesis of 2-(4-Hydroxyphenyl)benzofurans and Their Application to b-Amyloid Aggregation Inhibitor", Archives of Pharmacal Research, 2004, 19-24, 27(1).

(Continued)

*Primary Examiner* — Laura L. Stockton
(74) *Attorney, Agent, or Firm* — David Gryte

(57) ABSTRACT

The present invention relates to novel heteroaryl substituted benzothiazole derivatives, precursors thereof, and therapeutic uses for such compounds, having the structural formula (I) below: [Chemical formula should be inserted here. Please see paper copy] and to their pharmaceutically acceptable salt, compositions and methods of use. Furthermore, the invention relates to novel heteroaryl substituted benzothiazole derivatives that are suitable for imaging amyloid deposits in living patients, their compositions, methods of use and processes to make such compounds. More specifically, the present invention relates to a method of imaging amyloid deposits in brain in vivo to allow antemortem diagnosis of Alzheimer's disease as well as measuring clinical efficacy of Alzheimer's disease therapeutic agents.

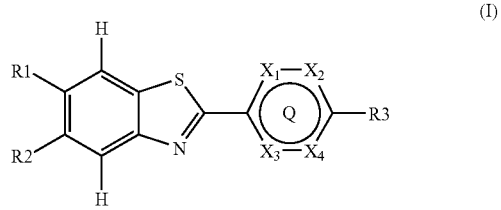

(I)

10 Claims, 7 Drawing Sheets

OTHER PUBLICATIONS

Coimbra et al., "The Role of MRI and PET/SPECT in Alzheimer's Disease", Curr.Top.Med.Chem, 2006, 629-647, vol. 6.
Guram et al., "New Catalysts for Suzuki-Miyaura Coupling Reactions of Heteroactom-Substituted Heteroaryl Chlorides", J. Org. Chem. 2007, p. 5104-5112, vol. 72.
Hardy et al., "The Amyloid Hypothesis of Alzheimer's Disease: Progress and Problems on the Road to Therapeutics", J. Science, 2002, 353-356, 297.
Howlett et al., "Inhibition of fibril formation in B-amyloid peptide by a novel series of benzofurans", Biochemical Journal, 1999, 283-289, 340(1).
Klunk et al., "Imaging Brain Amyloid in Alzheimer's Disease with Pittsburg Compound-B", Ann Neurol, 2004, 306-319, 55.
Kung et al., "IMPY: an improved thioflavin-T derivative for in vivo labeling of B-amyloid plaques", Brain Research, 2002, 202-210, 956.
Kung et al., "Binding of two potential imaging agents targeting amyloid plaques in postmortem brain tissues of patients with Alzheimer's disease", Brain Research, 2004, 98-105, 1025(1-2).
Kung et al., "Erratum to Binding of two potential imaging agents targeting amyloid plaques in postmortem brain tissues of patients with Alzheimer's disease", Brain Research, 2005, 302, 1031 (2).
Lockhart et al., "Evidence of the Presence of Three Distint Binding Sites for the Thioflavin T Class of Alzheimer's Disease PET Imaging Agents on B-Amyloid Peptide Fibrils", J Biol.Chem., 2005, 7677-7684, 280(9).
Lu, et al., "Synthesis and biodistribution of [131I]IMPY", Nuclear Science and Techniques, 2005, 289-292, 16(5).
Mathis et al., "Synthesis and Evalution of 11C-Labeled 6-Substituted 2-Arylbenzothiazoles as Amyloid Imaging Agents", Med Chem., 2003, 2740-2754, 46.
Miller, "A Better View of Brain Disorders", Science, 2006, 1376, 313.
Newberg et al., Safety, Biodistribution, and Dosimetry of 123I-IMPY: A Novel Amyloid Plaque-Imaging Agent for the Diagnosis of Alzheimer's Disease, Journal of Nuclear Medicine, 2006, 748-754, 47(5).
Nordberg, A. "PET imaging of amyloid in Alzheimer's disease", Lancet, Neurol., 2004, 519-527, 3.
Ono et al., Benzofuran derivatives as AB-aggregate-specific imaging agents for Alzheimer's disease, Nuclear Med. Biol., 2002, 633-642, 29(6).
Ono et al., "Synthesis and biological evaluation of (E)-3-styrylpyridine derivatives as amyloid imaging agents for Alzheimer's disease", Nuclear Medicine and Biology, 2005, 329-335, 32.
Ono et al., "Novel Benzofuran Derivatives for PET Imaging of B-Amyloid Plaques in Alzheimer's Disease Brains", J. Med. Chem., 2006, 2725-2730, 49.
Shi et al., "Antitumor Benzothiazoles. 3.1 Synthesis of 2-(4-Aminophenyl) benzothiazoles and Evaluation of Their Activities against Breast Cancer Cell Lines in Vitro and in Vivo", Journal of Medicinal Chemistry, 1996, 3375-3384, 39 (17).
Shoghi-Jadid et al., "Localization of Neurofibrillary Tangles and Beta-Amyloid Plaques in the Brains of Living Patients With Alzheimer Disease", The American Journal of Geriatric Psychiatry, 2002, 24-35, 10.
Thakak et al., "Reaction of guanidine with 3-formylchromones", Journal of the Indian Chemical Society, 1984, 550-2, 61(6): JICSAH;ISSN: 0019-4522, Abstract only AN 1985:149219, 1985.
Twyman et al., "A Short Synthesis of the B-amyloid (AB) Aggregation Inhibitor 3-p-Toluoyl-2-[4'-(3-diethylaminopropoxy)-phenyl]-benzofuran", Tetrahedron Lett, 1999, 9383-9384, 40(52).
Zeng et al., "Synthesis and evaluation of two 18F-labeled imidazol [1,2-a]pyridine analogues as potential agents for imaging B-amyloid in Alzheimer's disease", Bioorganic & Medicinal Chemistry Letters, 2006, 3015-3018, 16(11).
Zhang et al., "F-18 Stilbenes as PET Imaging Agents for Detecting B-Amyloid Plaques in the Brain", J.Med. Chem., 2005, 5980-5988, 48.
Zhang et al., "18F-labeled styrylpyridines as PET agents for amyloid plaque imaging", Nuclear Medicine and Biology, 2007, 89-97, 34.
Zhuang et al., "IBOX (2-(4'-dimethylaminophenyl)-6-iodobenzoxazole) : a ligand for imaging amyloid plaques in the brain", Nuclear Medicine and Biology, 2002, 887-894, 28(8), CODEN:NMBIEO;ISSN:0969-8051.
Zhuang et al., "Structure-Activity Relationship of Imidazo[1,2-a]pyridines as Ligands for Detecting B-Amyloid Plaques in the Brain", Journal of Medicinal Chemistry, 2003, 237-243, 46(2).
English abstract for JP11116476, 1999.
English abstract for JP2004250411, 2004.
STN International, File CAPLUS, CAPLUS accession No. 1988:580390, document No. 109:180390, Shiino, Yasuko et al., "Electrophotographic charge-generating disazo photoconductors", & JP, A, 63094248, 19880425, 1988.
STN International, File HCAPLUS, HCAPLUS accession No. 1999:476741, Document No. 131:228612, Benhida, Rachid et al:"Synthesis of 6-allyl—and 6-heteroarylindoles by palladium catalyzed stille cross-coupling reaction", &Tetrahedron Letters (1999), 40(31), 5701-5703.
158229 CAPLUS, AN 2002:293449, DN 136:319426, 2002.
STN International, File CAPLUS, CAPLUS accession No. 2003:60939, document No. 138:287190, Soares-Santos, P.C.R. et al., "Blue-emitting flurophores based on 1,3-benzoxazolyl and 1,3-benzothiazolyl-substituted indoles and carbazoles", & Advances in Colour Science and Technology (2002), 5(4), 94-98.
International Search Report for International Application No. PCT/SE2007/000068, 2007.
Swedish Patent Office Search Report dated Aug. 4, 2006.
Vippagunta et al., Crystalline Solids:, 2001, Advanced Drug Delivery Reviews, 48, pp. 3 and 18.
Office Action for U.S. Appl. No. 11/763,151 mailed Aug. 6, 2008.
Office Action for U.S. Appl. No. 11/763,151 mailed Jun. 12, 2008.
F. Catti Boccuzzi, et al, "NMR Spectra of the Pyridyl-benzo-X-azoles Systems"; Abstract XP-002595714; AN 1977:88596 CAPLUS, 1977.
F. Catti Boccuzzi, et al, "NMR Spectra of the Pyridyl-benzo-X-azoles Systems"; Italian full text version, Chimica Organica, 1975, 109 (5-6), pp. 655-660.
G. Di Modica, et al., "Benzo-x-azolylpyridine system in relation to the synthesis of dyes"; Abstract XP-002595715; AN 1975: 113165 CAPLUS, 1975.
G. Di Modica, et al., "Benzo-x-azolylpyridine system in relation to the synthesis of dyes"; Italian full text version, Tinctoria, 1974, 71(10), pp. 333-337.
P. Savarino, et al., "Azo dyes for polyamide and cellulose fibers containing pyridinebenzothiazole systems"; Abstract XP-002595716; AN 1976:578949 CAPLUS, 1976.
P. Savarino, et al., "Azo dyes for polyamide and cellulose fibers containing pyridinebenzothiazole systems"; Italian full text version, Chimica e l'Industria, 1976, 58(4), p. 293.
M. R. Jayanth, et al., "Studies in Vilsmeier-Haack Reaction: Part VIII—Synthesis of New Heterocyclic Derivatives from ... Naphth-2, I-Oxazole", Indian Journal of Chemistry, vol. 11, Nov. 1973, pp. 1112-1114.
Lisheng Cai, et al., "Synthesis and Evaluation of Two F-Labeled . . . in Alzheimer's Disease", J. Med. Chem. 2004, 47, pp. 2208-2218.
Bjorkman et al., "Synthesis of 11C/13C-Labelled Prostacyclins" Acta Chemica Scandinavia, 1998, vol. 52, pp. 635-640.
Langstrom et al., "Compounds Labelled with Short-Lived β -Emitting Radionuclides and Some Applications in Life Sciences. The Importance of Time as a Parameter " Acta Chemica Scandinavia, 1999, vol. 53, pp. 651-669.

* cited by examiner

[³H] PIB    [³H] AZAD

Human

APP / PS 1 mice

[³H] PIB    [³H] AZAD

Unrinsed

Rinsed 0-7 min   21-40 min   50-87 min     0-7 min   21-40 min   50-87 min 0-7 min   21-40 min   50-87 min

HETEROARYL SUBSTITUTED BENZOTHIAZOLES

The present invention relates to novel heteroaryl substituted benzothiazole derivatives and therapeutic uses for such compounds. Furthermore, the invention relates to novel heteroaryl substituted benzothiazole derivatives that are suitable for imaging amyloid deposits in living patients, their compositions, methods of use and processes to make such compounds. More specifically, the present invention relates to a method of imaging amyloid deposits in brain in vivo to allow antemortem diagnosis of Alzheimer's disease as well as measuring clinical efficacy of Alzheimer's disease therapeutic agents.

BACKGROUND OF THE INVENTION

Amyloidosis is a progressive, incurable metabolic disease of unknown cause characterized by abnormal deposits of protein in one or more organs or body systems. Amyloid proteins are manufactured, for example, by malfunctioning bone marrow. Amyloidosis, which occurs when accumulated amyloid deposits impair normal body function, can cause organ failure or death. It is a rare disease, occurring in about eight of every 1,000,000 people. It affects males and females equally and usually develops after the age of 40. At least 15 types of amyloidosis have been identified. Each one is associated with deposits of a different kind of protein.

The major forms of amyloidosis are primary systemic, secondary, and familial or hereditary amyloidosis. There is also another form of amyloidosis associated with Alzheimer's disease. Primary systemic amyloidosis usually develops between the ages of 50 and 60. With about 2,000 new cases diagnosed annually, primary systemic amyloidosis is the most common form of this disease in the United States. Also known as light-chain-related amyloidosis, it may also occur in association with multiple myeloma (bone marrow cancer). Secondary amyloidosis is a result of chronic infection or inflammatory disease. It is often associated with Familial Mediterranean fever (a bacterial infection characterized by chills, weakness, headache, and recurring fever), Granulomatous ileitis (inflammation of the small intestine), Hodgkin's disease, Leprosy, Osteomyelitis and Rheumatoid arthritis.

Familial or hereditary amyloidosis is the only inherited form of the disease. It occurs in members of most ethnic groups, and each family has a distinctive pattern of symptoms and organ involvement. Hereditary amyloidosis is though to be autosomal dominant, which means that only one copy of the defective gene is necessary to cause the disease. A child of a parent with familial amyloidosis has a 50-50 risk of developing the disease.

Amyloidosis can involve any organ or system in the body. The heart, kidneys, gastrointestinal system, and nervous system are affected most often. Other common sites of amyloid accumulation include the brain, joints, liver, spleen, pancreas, respiratory system, and skin.

Alzheimer's disease (AD) is the most common form of dementia, a neurologic disease characterized by loss of mental ability severe enough to interfere with normal activities of daily living, lasting at least six months, and not present from birth. AD usually occurs in old age, and is marked by a decline in cognitive functions such as remembering, reasoning, and planning.

Between two and four million Americans have AD; that number is expected to grow to as many as 14 million by the middle of the 21st century as the population as a whole ages. While a small number of people in their 40 s and 50 s develop the disease, AD predominantly affects the elderly. AD affects about 3% of all people between ages 65 and 74, about 20% of those between 75 and 84, and about 50% of those over 85. Slightly more women than men are affected with AD, even when considering women tend to live longer, and so there is a higher proportion of women in the most affected age groups.

The accumulation of amyloid Aβ-peptide in the brain is a pathological hallmark of all forms of AD. It is generally accepted that deposition of cerebral amyloid Aβ-peptide is the primary influence driving AD pathogenesis. (Hardy J and Selkoe D. J., Science. 297: 353-356, 2002).

Imaging techniques, such as positron emission tomography (PET) and single photon emission computed tomography (SPECT), are effective in monitoring the accumulation of amyloid deposits in the brain and correlating it to the progression of AD (Shoghi-Jadid et al. The American journal of geriatric psychiatry 2002, 10, 24; Miller, Science, 2006, 313, 1376; Coimbra et al. Curr. Top. Med. Chem. 2006, 6, 629; Nordberg, Lancet Neurol. 2004, 3, 519). The application of these techniques requires the development of radioligands that readily enter the brain and selectively bind to amyloid deposits in vivo.

A need exists for amyloid binding compounds that are non-toxic and can cross the blood-brain barrier, and consequently, can be used in diagnostics. Furthermore, it is important to be able to monitor the efficacy of the treatment given to AD patients, by measuring the effect of said treatment by measuring changes of AD plaque level.

Properties of particular interest of a detectable amyloid binding compound, besides high affinity for amyloid deposits in vivo and high and rapid brain entrance, include low unspecific binding to normal tissue and rapid clearance from the same. These properties are commonly dependant on the lipophilicity of the compound (Coimbra et al. Curr. Top. Med. Chem. 2006, 6, 629). Based partly on the relatively higher clearance from normal brain tissue as compared to related analogues, [$^{11}$C]PIB was selected from amongst these for further evaluations in human subjects (Mathis et al. J. Med. Chem. 2003, 46, 2740). Subsequently, a study on the use of [$^{11}$C]PIB for the detection of amyloid deposits in-vivo in the human by the PET-technique was conducted (Klunk et al. Ann Neurol. 2004, 55, 306). In this study, significant higher retention of [$^{11}$C]PIB in relevant regions of the brain, was observed in subjects with diagnosed AD as compared to healthy controls. Related methods and derivatives are described in WO 2002/16333 and WO 2004/083195.

There is a need for improved compounds in order to obtain a signal-to-noise ratio high enough to allow detailed detection of amyloid deposits throughout all brain regions, and providing improved reliability in quantiative studies on amyloid plaque load in relation to drug treatments.

The present invention provides heteroaryl substituted benzothiazole derivatives that carry such unexpected improvements over known benzothiazole derivatives providing inter alia advantageously associated low unspecific binding and rapid brain clearance.

DISCLOSURE OF THE INVENTION

The present invention provides methods for measuring effects of amyloid binding compounds, by measuring changes of AD plaque level.

In one aspect of the invention, there is provided a compound according to formula I:

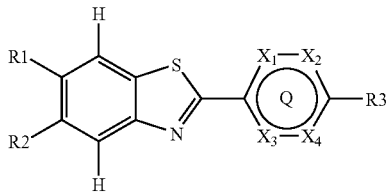

wherein
R1 is selected from hydrogen, halo, $C_{1-5}$ alkyl, $C_{1-6}$ fluoroalkyl, $C_{1-3}$ alkyleneO$C_{1-3}$ alkyl, $C_{1-3}$ alkyleneO$C_{1-3}$ fluorolkyl, $C_{1-3}$ alkyleneNH$_2$, $C_{1-3}$ alkyleneNH$C_{1-3}$ alkyl, $C_{1-3}$ alkyleneN($C_{1-3}$ alkyl)$_2$, $C_{1-3}$ alkyleneNH$C_{1-3}$ fluoroalkyl, $C_{1-3}$ alkyleneN($C_{1-3}$ fluoroalkyl)$_2$, $C_{1-3}$ alkyleneN($C_{1-3}$ alkyl) $C_{1-3}$ fluoroalkyl, hydroxy, $C_{1-6}$ alkoxy, $C_{1-6}$ fluoroalkoxy, amino, NH$C_{1-3}$ alkyl, NH$C_{1-3}$ fluoroalkyl, N($C_{1-3}$ alkyl)$_2$, N($C_{1-3}$ fluoroalkyl)$_2$, N($C_{1-3}$ alkyl)$C_{1-3}$ fluoroalkyl, NH(CO) $C_{1-3}$ alkyl, NH(CO)$C_{1-3}$ fluorolkyl, NH(CO)$C_{1-3}$ alkoxy, NH(CO)$C_{1-3}$ fluoroalkoxy, NHSO$_2$$C_{1-3}$ alkyl, NHSO$_2$$C_{1-3}$ fluoroalkyl, (CO)$C_{1-3}$ alkyl, (CO)$C_{1-3}$ fluoroalkyl, COOH, (CO)$C_{1-3}$ alkoxy, (CO)$C_{1-3}$ fluoroalkoxy, (CO)NH$_2$, (CO)NH$C_{1-3}$ alkyl, (CO)NH$C_{1-3}$ fluoroalkyl, (CO)N($C_{1-3}$ alkyl)$_2$, (CO)N($C_{1-3}$ fluoroalkyl)$_2$, (CO)N($C_{1-3}$ alkyl)$C_{1-3}$ fluoroalkyl, (CO)N($C_{4-6}$ alkylene), (CO)N($C_{4-6}$ fluoroalkylene), cyano and SO$_2$NH$_2$;
R2 is selected from hydrogen, halo, $C_{1-6}$ alkyl, $C_{1-6}$ fluoroalkyl, $C_{1-3}$ alkyleneO$C_{1-3}$ alkyl, $C_{1-3}$ alkyleneO$C_{1-3}$ fluorolkyl, $C_{1-3}$ alkyleneNH$_2$, $C_{1-3}$ alkyleneNH$C_{1-3}$ alkyl, $C_{1-3}$ alkyleneN($C_{1-3}$ alkyl)$_2$, $C_{1-3}$ alkyleneNH$C_{1-3}$ fluoroalkyl, $C_{1-3}$ alkyleneN($C_{1-3}$ fluoroalkyl)$_2$, $C_{1-3}$ alkyleneN($C_{1-3}$ alkyl) $C_{1-3}$ fluoroalkyl, hydroxy, $C_{1-6}$ alkoxy, $C_{1-6}$ fluoroalkoxy, amino, NH$C_{1-3}$ alkyl, NH$C_{1-3}$ fluoroalkyl, N($C_{1-3}$ alkyl)$_2$, N($C_{1-3}$ fluoroalkyl)$_2$, N($C_{1-3}$ alkyl)$C_{1-3}$ fluoroalkyl, NH(CO) $C_{1-3}$ alkyl, NH(CO)$C_{1-3}$ fluoroalkyl, NH(CO)$C_{1-3}$ alkoxy, NH(CO)$C_{1-3}$ fluoroalkoxy, NHSO$_2$$C_{1-3}$ alkyl, NHSO$_2$$C_{1-3}$ fluoroalkyl, (CO)$C_{1-3}$ alkyl, (CO)$C_{1-3}$ fluoroalkyl, COOH, (CO)$C_{1-3}$ alkoxy, (CO)$C_{1-3}$ fluoroalkoxy, (CO)NH$_2$, (CO)NH$C_{1-3}$ allyl, (CO)NH$C_{1-3}$ fluoroalkyl, (CO)N($C_{1-3}$ alkyl)$_2$, (CO)N($C_{1-3}$ fluoroalkyl)$_2$, (CO)N($C_{1-3}$ alkyl)$C_{1-3}$ fluoroalkyl, (CO)N($C_{4-6}$ alkylene), (CO)N($C_{4-6}$ fluoroalkylene) and cyano; or
R1 and R2 together forms a ring;

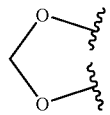

R3 is selected from fluoro, bromo, iodo, $C_{1-4}$ alkyl, $C_{1-4}$ fluoroalkyl, trifluoromethyl, $C_{1-3}$ alkyleneO$C_{1-3}$ alkyl, $C_{1-3}$ alkyleneO$C_{1-3}$ fluoroalkyl, $C_{1-3}$ alkyleneNH$_2$, $C_{1-3}$ alkyleneNH$C_{1-3}$ alkyl, $C_{1-3}$ alkyleneN($C_{1-3}$ alkyl)$_2$, $C_{1-3}$ alkyleneNH$C_{1-3}$ fluoroalkyl, $C_{1-3}$ alkyleneN($C_{1-3}$ fluoroalkyl)$_2$, $C_{1-3}$ alkyleneN($C_{1-3}$ alkyl)$C_{1-3}$ fluoroalkyl, hydroxy, $C_{1-4}$ alkoxy, $C_{1-4}$ fluoroalkoxy, amino, NH$C_{1-3}$ alkyl, NH$C_{1-3}$ fluoroalkyl, N($C_{1-3}$ alkyl)$_2$, N($C_{1-3}$ fluoroalkyl)$_2$, N($C_{1-3}$ alkyl)$C_{1-3}$ fluoroalkyl, NH($C_{0-3}$ alkylene)G2, N($C_{0-1}$ alkyl)N ($C_{0-1}$ alkyl)$_2$, N($C_{0-1}$ alkyl)O$C_{0-1}$ alkyl, NH(CO)$C_{1-3}$ alkyl, NH(CO)$C_{1-3}$ fluoroalkyl, NH(CO)G2, (CO)$C_{1-3}$ alkyl, (CO) $C_{1-3}$ fluorolkyl, (CO)$C_{1-3}$ alkoxy, (CO)$C_{1-3}$ fluoroalkoxy, (CO)NH$_2$, (CO)NH$C_{1-3}$ alkyl, (CO)NH$C_{1-3}$ fluoroalkyl, (CO)N($C_{1-3}$ alkyl)$_2$, (CO)N($C_{1-3}$ fluoroalkyl)$_2$, (CO)N($C_{1-3}$ alkyl)$C_{1-3}$ fluoroalkyl, (CO)N($C_{4-6}$ alkylene), (CO)N($C_{4-6}$ fluoroalkylene), (CO)NH$_2$G2, SO$_2$NH$_2$, SO$_2$NH$C_{1-3}$ alkyl, SO$_2$NH$C_{1-3}$ fluoroalkyl, SO$_2$N($C_{1-3}$ alkyl)$_2$, SO$_2$N($C_{1-3}$ fluoroalkyl)$_2$, SO$_2$N($C_{1-3}$ alkyl)$C_{1-3}$ fluoroalkyl, cyano, SO$_2$$C_{1-6}$ alkyl, S$C_{1-6}$ alkyl, S$C_{1-6}$ fluoroalkyl, N($C_{4-6}$ alkylene) and G1, wherein G1 is;

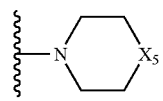

$X_5$ is selected from O, NH, N$C_{1-3}$ alkyl and N$C_{1-3}$ fluoroalkyl;
G2 is phenyl or a 5- or 6-membered aromatic heterocycle, optionally substituted with a substituent selected from fluoro, bromo, iodo, methyl and methoxy;
Q is a 6-membered aromatic heterocycle containing either one or two N-atoms, wherein $X_1$, $X_2$, $X_3$ and $X_4$ are independently selected from N or C, and wherein one or two of $X_1$, $X_2$, $X_3$ and $X_4$ is N and the remaining is C, and if $X_4$ is C, said C is optionally substituted with fluoro or iodo;
and one or more of the atoms of formula I is optionally a detectable isotope;
as a free base or a pharmaceutically acceptable salt, solvate or solvate of a salt thereof, with the proviso that when R1 and R2 both are H, R3 is not methyl, hydroxy, amino, aminophenyl, aminoacetyl or methoxy.

In another aspect of the invention, there is provided a compound according to formula I

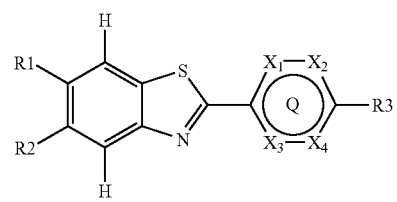

wherein
R1 is selected from hydrogen, halo, $C_{1-5}$ alkyl, $C_{1-6}$ fluoroalkyl, $C_{1-3}$ alkyleneO$C_{1-3}$ alkyl, $C_{1-3}$ alkyleneO$C_{1-3}$ fluorolkyl, $C_{1-3}$ alkyleneNH$_2$, $C_{1-3}$ alkyleneNH$C_{1-3}$ alkyl, $C_{1-3}$ alkyleneN($C_{1-3}$ alkyl)$_2$, $C_{1-3}$ alkyleneNH$C_{1-3}$ fluoroalkyl, $C_{1-3}$ alkyleneN($C_{1-3}$ fluoroalkyl)$_2$, $C_{1-3}$ alkyleneN($C_{1-3}$ alkyl) $C_{1-3}$ fluoroalkyl, hydroxy, $C_{1-6}$ alkoxy, $C_{1-6}$ fluoroalkoxy, amino, NH$C_{1-3}$ alkyl, NH$C_{1-3}$ fluoroalkyl, N($C_{1-3}$ alkyl)$_2$, N($C_{1-3}$ fluoroalkyl)$_2$, N($C_{1-3}$ alkyl)$C_{1-3}$ fluoroalkyl, NH(CO) $C_{1-3}$ alkyl, NH(CO)$C_{1-3}$ fluorolkyl, NH(CO)$C_{1-3}$ alkoxy, NH(CO)$C_{1-3}$ fluoroalkoxy, NHSO$_2$$C_{1-3}$ alkyl, NHSO$_2$$C_{1-3}$ fluoroalkyl, (CO)$C_{1-3}$ alkyl, (CO)$C_{1-3}$ fluoroalkyl, COOH, (CO)$C_{1-3}$ alkoxy, (CO)$C_{1-3}$ fluoroalkoxy, (CO)NH$_2$, (CO) NH$C_{1-3}$ alkyl, (CO)NH$C_{1-3}$ fluoroalkyl, (CO)N($C_{1-3}$ alkyl)$_2$, (CO)N($C_{1-3}$ fluoroalkyl)$_2$, (CO)N($C_{1-3}$ alkyl)$C_{1-3}$ fluoroalkyl, (CO)N($C_{4-6}$ alkylene), (CO)N($C_{4-6}$ fluoroalkylene) and cyano;
R2 is selected from hydrogen, halo, $C_{1-6}$ alkyl, $C_{1-6}$ fluoroalkyl, $C_{1-3}$ alkyleneO$C_{1-3}$ alkyl, $C_{1-3}$ alkyleneO$C_{1-3}$ fluorolkyl, $C_{1-3}$ alkyleneNH$_2$, $C_{1-3}$ alkyleneNH$C_{1-3}$ alkyl, $C_{1-3}$ alkyleneN($C_{1-3}$ alkyl)$_2$, $C_{1-3}$ alkyleneNH$C_{1-3}$ fluoroalkyl, $C_{1-3}$ alkyleneN($C_{1-3}$ fluoroalkyl)$_2$, $C_{1-3}$ alkyleneN($C_{1-3}$ alkyl) $C_{1-3}$ fluoroalkyl, hydroxy, $C_{1-6}$ alkoxy, $C_{1-6}$ fluoroalkoxy, amino, NHC$_{1-3}$ alkyl, NHC$_{1-3}$ fluoroalkyl, N(C$_{1-3}$ alkyl)$_2$, N(C$_{1-3}$ fluoroalkyl)$_2$, N(C$_{1-3}$ alkyl)C$_{1-3}$ fluoroalkyl, NH(CO)C$_{1-3}$ alkyl, NH(CO)C$_{1-3}$ fluoroalkyl, NH(CO)C$_{1-3}$ alkoxy, NH(CO)C$_{1-3}$ fluoroalkoxy, NHSO$_2$C$_{1-3}$ alkyl, NHSO$_2$C$_{1-3}$ fluoroalkyl, (CO)C$_{1-3}$ alkyl, (CO)C$_{1-3}$ fluoroalkyl, COOH, (CO)C$_{1-3}$ alkoxy, (CO)C$_{1-3}$ fluoroalkoxy, (CO)NH$_2$, (CO)NHC$_{1-3}$ alkyl, (CO)NHC$_{1-3}$ fluoroalkyl, (CO)N(C$_{1-3}$ alkyl)$_2$, (CO)N(C$_{1-3}$ fluoroalkyl)$_2$, (CO)N(C$_{1-3}$ alkyl)C$_{1-3}$ fluoroalkyl, (CO)N(C$_{4-6}$ alkylene), (CO)N(C$_{4-6}$ fluoroalkylene) and cyano;

R3 is selected from fluoro, bromo, iodo, C$_{1-4}$ alkyl, C$_{1-4}$ fluoroalkyl, trifluoromethyl, C$_{1-3}$ alkyleneOC$_{1-3}$ alkyl, C$_{1-3}$ alkyleneOC$_{1-3}$ fluoroalkyl, C$_{1-3}$ alkyleneNH$_2$, C$_{1-3}$ alkyleneNHC$_{1-3}$ alkyl, C$_{1-3}$ alkyleneN(C$_{1-3}$ alkyl)$_2$, C$_{1-3}$ alkyleneNHC$_{1-3}$ fluoroalkyl, C$_{1-3}$ alkyleneN(C$_{1-3}$ fluoroalkyl)$_2$, C$_{1-3}$ alkyleneN(C$_{1-3}$ alkyl)C$_{1-3}$ fluoroalkyl, hydroxy, C$_{1-4}$ alkoxy, C$_{1-4}$ fluoroalkoxy, amino, NHC$_{1-3}$ alkyl, NHC$_{1-3}$ fluoroalkyl, N(C$_{1-3}$ alkyl)$_2$, N(C$_{1-3}$ fluoroalkyl)$_2$, N(C$_{1-3}$ alkyl)C$_{1-3}$ fluoroalkyl, NH(C$_{0-3}$ alkylene)G2, N(C$_{0-1}$ alkyl)N(C$_{0-1}$ alkyl)$_2$, N(C$_{0-1}$ alkyl)OC$_{0-1}$ alkyl, NH(CO)C$_{1-3}$ alkyl, NH(CO)C$_{1-3}$ fluoroalkyl, NH(CO)G2, (CO)C$_{1-3}$ alkyl, (CO)C$_{1-3}$ fluorolkyl, (CO)C$_{1-3}$ alkoxy, (CO)C$_{1-3}$ fluoroalkoxy, (CO)NH$_2$, (CO)NHC$_{1-3}$ alkyl, (CO)NHC$_{1-3}$fluoroalkyl, (CO)N(C$_{1-3}$ alkyl)$_2$, (CO)N(C$_{1-3}$ fluoroalkyl)$_2$, (CO)N(C$_{1-3}$ alkyl)C$_{1-3}$ fluoroalkyl, (CO)N(C$_{4-6}$ alkylene), (CO)N(C$_{4-6}$ fluoroalkylene), (CO)NH$_2$G2, SO$_2$NH$_2$, SO$_2$NHC$_{1-3}$ alkyl, SO$_2$NHC$_{1-3}$ fluoroalkyl, SO$_2$N(C$_{1-3}$ alkyl)$_2$, SO$_2$N(C$_{1-3}$ fluoroalkyl)$_2$, SO$_2$N(C$_{1-3}$ alkyl)C$_{1-3}$ fluoroalkyl, cyano and G1, wherein G1 is;

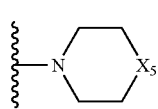

G1

X$_5$ is selected from O, NH, NC$_{1-3}$ alkyl and NC$_{1-3}$ fluorolkyl; G2 is phenyl or a 5- or 6-membered aromatic heterocycle, optionally substituted with a substituent selected from fluoro, bromo, iodo, methyl and methoxy;

Q is a 6-membered aromatic heterocycle containing either one or two N-atoms, wherein X$_1$, X$_2$, X$_3$ and X$_4$ are independently selected from N or C, and wherein one or two of X$_1$, X$_2$, X$_3$ and X$_4$ is N and the remaining is C;

as a free base or a pharmaceutically acceptable salt, solvate or solvate of a salt thereof, with the proviso that when R1 and R2 both are H, R3 is not methyl, hydroxy, amino, aminophenyl, aminoacetyl or methoxy.

In another aspect of the invention, there is provided a compound according to formula I, wherein R1 is selected from hydrogen, halo, C$_{1-5}$ alkyl, hydroxy, C$_{1-6}$ alkoxy, amino, NHC$_{1-3}$ alkyl, NHC$_{1-3}$ fluoroalkyl, N(C$_{1-3}$ alkyl)$_2$, NH(CO)C$_{1-3}$ alkyl, NH(CO)C$_{1-3}$ fluoroalkyl, (CO)NH$_2$, (CO)NHC$_{1-3}$ alkyl and (CO)NHC$_{1-3}$ fluoroalkyl.

In another aspect of the invention, there is provided a compound according to formula I, wherein R2 is selected from hydrogen, halo, C$_{1-6}$ alkyl, hydroxy, C$_{1-6}$ alkoxy, amino, NHC$_{1-3}$ alkyl, NHC$_{1-3}$ fluoroalkyl, N(C$_{1-3}$ alkyl)$_2$, NH(CO)C$_{1-3}$ alkyl, NH(CO)C$_{1-3}$ fluoroalkyl, (CO)NH$_2$, (CO)NHC$_{1-3}$ alkyl and (CO)NHC$_{1-3}$ fluoroalkyl.

In another aspect of the invention, there is provided a compound according to formula I, wherein R3 is selected from fluoro, bromo, iodo, hydroxy, C$_{1-4}$ alkoxy, trifluoromethyl, C$_{1-4}$ fluoroalkoxy, amino, NHC$_{1-3}$ alkyl, NHC$_{1-3}$ fluoroalkyl, N(C$_{1-3}$ alkyl)$_2$, N(C$_{1-3}$ fluoroalkyl)$_2$, N(C$_{1-3}$ alkyl)C$_{1-3}$ fluoroalkyl, (CO)NH$_2$, NH(C$_{1-3}$ alkylene)G2, NH(CO)C$_{1-3}$ alkyl and G1, wherein X$_5$ is selected from NH, O and NMe; G2 is phenyl or pyridyl, said phenyl or pyridyl optionally substituted with a substituent selected from fluoro, methyl and methoxy.

In another aspect of the invention, there is provided a compound according to formula I, wherein Q is a pyridine ring, wherein X$_1$ and X$_2$ are independently selected from N or C, and wherein one of X$_1$ and X$_2$ is N and the remaining of X$_1$, X$_2$, X$_3$ and X$_4$ are C.

In another aspect of the invention, there is provided a compound according to formula I, wherein Q is a pyrimidine ring, wherein X$_1$ and X$_2$ are independently selected from N or C, and wherein one of X$_1$ and X$_2$ is N; and wherein X$_3$ and X$_4$ are independently selected from N or C, and wherein one of X$_3$ and X$_4$ is N.

In another aspect of the invention, there is provided a compound according to formula I, wherein R2 is selected from hydrogen, fluoro, bromo, iodo, amino, methyl, hydroxy, methoxy, NHMe and (CO)NH$_2$.

In another aspect of the invention, there is provided a compound according to formula I, wherein R is selected from hydrogen, methoxy and amino.

In another aspect of the invention, there is provided a compound according to formula I, wherein R1 is selected from hydrogen, fluoro, bromo, iodo, amino, methyl, hydroxy, is methoxy, NHMe and (CO)NH$_2$.

In another aspect of the invention, there is provided a compound according to formula I, wherein R3 is selected from fluoro, methoxy, ethoxy, trifluoromethyl, NHMe, amino, N(C$_{1-3}$ alkyl)$_2$, (CO)NH$_2$, and G1, wherein X$_5$ is selected from NH, O and NMe.

In another aspect of the invention, there is provided a compound according to formula I, wherein Q is a pyridine ring, wherein X$_2$ is N, and X$_1$, X$_3$ and X$_4$ are C.

In another aspect of the invention, there is provided a compound according to formula I, wherein Q is a pyridine ring, wherein X$_4$ is N, and X$_1$, X$_2$ and X$_3$ are C.

In another aspect of the invention, there is provided a compound according to formula I, wherein Q is a pyrimidine ring, wherein X$_2$ and X$_4$ are N; and X$_1$ and X$_3$ are C.

In another aspect of the invention, there is provided a compound according to formula I, comprising one $^{11}$C atom, wherein one of R1 and R2 is either hydroxy or [$^{11}$C]methoxy, and the other one of R1 and R2 is H;

R3 is selected from amino, NHMe, NH$^{11}$CH$_3$ and N(Me)$^{11}$CH$_3$;

Q is a pyridine ring, wherein X$_1$ and X$_2$ are independently selected from N or C, and wherein one of X$_1$ and X$_2$ is N and the remaining of X$_1$, X$_2$, X$_3$ and X$_4$ are C.

In another aspect of the invention, there is provided a compound according to formula I, said compound being:

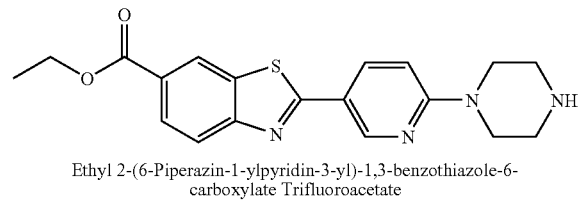

Ethyl 2-(6-Piperazin-1-ylpyridin-3-yl)-1,3-benzothiazole-6-carboxylate Trifluoroacetate -continued Ethyl 2-[6-(4-Methylpiperazin-1-yl)pyridin-3-yl]-1,3-benzothiazole-6-carboxylate 2-[6-(4-Methylpiperazin-1-yl)pyridin-3-yl]-1,3-benzothiazole-6-carboxamide Acetate 6-Methoxy-2-(6-piperazin-1-ylpyridin-3-yl)-1,3-benzothiazole 6-Methoxy-2-[6-(4-methylpiperazin-1-yl)pyridin-3-yl]-1,3-benzothiazole 2-[6-(4-Methylpiperazin-1-yl)pyridin-3-yl]-1,3-benzothiazol-6-ol Acetate Ethyl 2-(6-Methoxypyridin-3-yl)-1,3-benzothiazole-6-carboxylate 2-(6-Methoxypyridin-3-yl)-1,3-benzothiazole-6-carboxylic Acid 2-(6-Methoxypyridin-3-yl)-1,3-benzothiazole-6-carboxamide 2-(6-Methoxypyridin-3-yl)-N-methyl-1,3-benzothiazole-6-carboxamide 2-(6-Methoxypyridin-3-yl)-6-(pyrrolidin-1-ylcarbonyl)-1-3-benzothiazole -continued 2-(6-Piperazin-1-ylpyridin-3-yl)-1,3-benzothiazol-6-amine N-[2-(6-Piperazin-1-ylpyridin-3-yl)-1,3-benzothiazol-6-yl]methanesulfonamide 2-[6-(4-Methylpiperazin-1-yl)pyridin-3-yl]-1,3-benzothiazol-6-amine Trifluoroacetate N-{2-[6-(4-Methylpiperazin-1-yl)pyridin-3-yl]-1,3-benzothiazol-6-yl}acetamide 2-[6-(4-Methylpiperazin-1-yl)pyridin-3-yl]-N-(2,2,2-trifluoroethyl)-1,3-benzothiazol-6-amine Ethyl {2-[6-(4-Methylpiperazin-1-yl)pyridin-3-yl]-1,3-benzothiazol-6-yl}carbamate N-Methyl-2-[6-(4-methylpiperazin-1-yl)pyridin-3-yl]-1,3-benzothiazol-6-amine 2-(6-Methoxypyridin-3-yl)-1,3-benzothiazol-6-amine N-[2-(6-Methoxypyridin-3-yl)-1,3-benzothiazol-6-yl]acetamide N-[2-(6-Methoxypyridin-3-yl)-1,3-benzothiazol-6-yl]methanesulfonamide

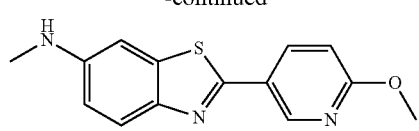

2-(6-Methoxypyridin-3-yl)-N-methyl-1,3-
benzothiazol-6-amine

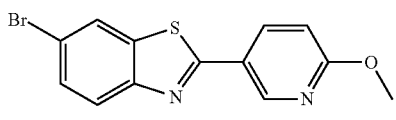

6-Bromo-2-(6-methoxypyridin-3-yl)-1,3-
benzothiazole

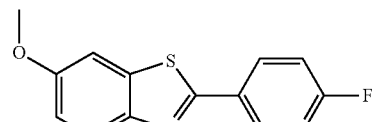

2-(6-Fluoropyridin-3-yl)-6-methoxy-
1,3-benzothiazole

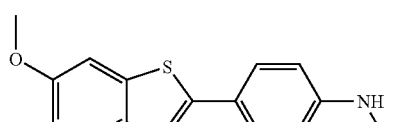

5-(6-Methoxy-1,3-benzothiazol-2-yl)-
N-methylpyridin-2-amine

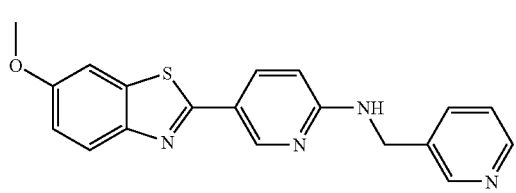

5-(6-Methoxy-1,3-benzothiazol-2-yl)-
N-(pyridin-3-ylmethyl)pyridin-2-amine

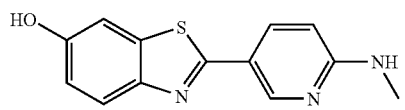

2-[6-(Methylamino)pyridin-3-yl]-
1,3-benzothiazol-6-ol

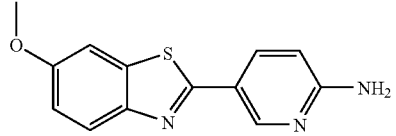

5-(6-Methoxy-1,3-benzothiazol-
2-yl)pyridin-2-amine

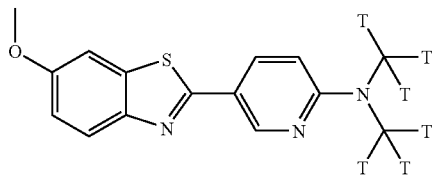

[N-Dimethyl-3H6]-[5-(6-Methoxy-benzothiazol-2-yl)-pyridin-2-yl]-
dimethyl-amine

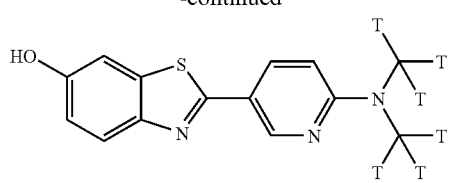

[N-Dimethyl-3H6]-2-(6-Dimethylamino-pyridin-3-yl)-
benzothiazol-6-ol

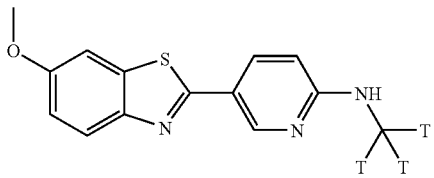

[N-Methyl-3H3]-[5-(6-Methoxy-benzothiazol-2-yl)-
pyridin-2-yl]-methyl-amine

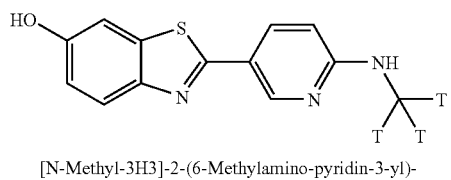

[N-Methyl-3H3]-2-(6-Methylamino-pyridin-3-yl)-
benzothiazol-6-ol

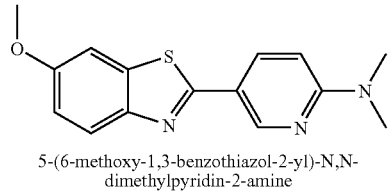

5-(6-methoxy-1,3-benzothiazol-2-yl)-N,N-
dimethylpyridin-2-amine

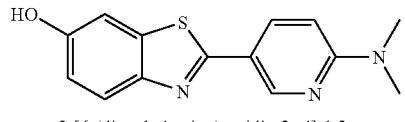

2-[6-(dimethylamino)pyridin-3-yl]-1,3-
benzothiazol-6-ol

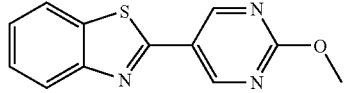

2-(2-methoxypyrimidin-5-yl)-
1,3-benzothiazole

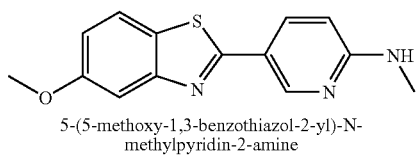

5-(5-methoxy-1,3-benzothiazol-2-yl)-N-
methylpyridin-2-amine

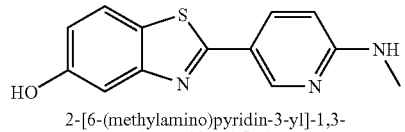

2-[6-(methylamino)pyridin-3-yl]-1,3-
benzothiazol-5-ol

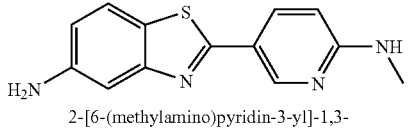

2-[6-(methylamino)pyridin-3-yl]-1,3-
benzothiazol-5-amine

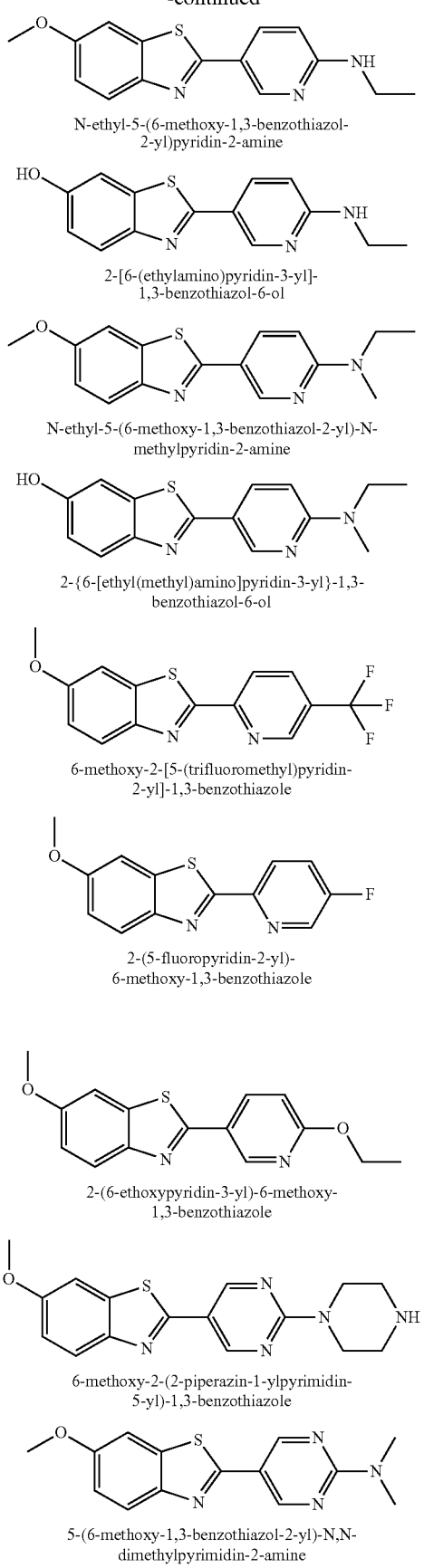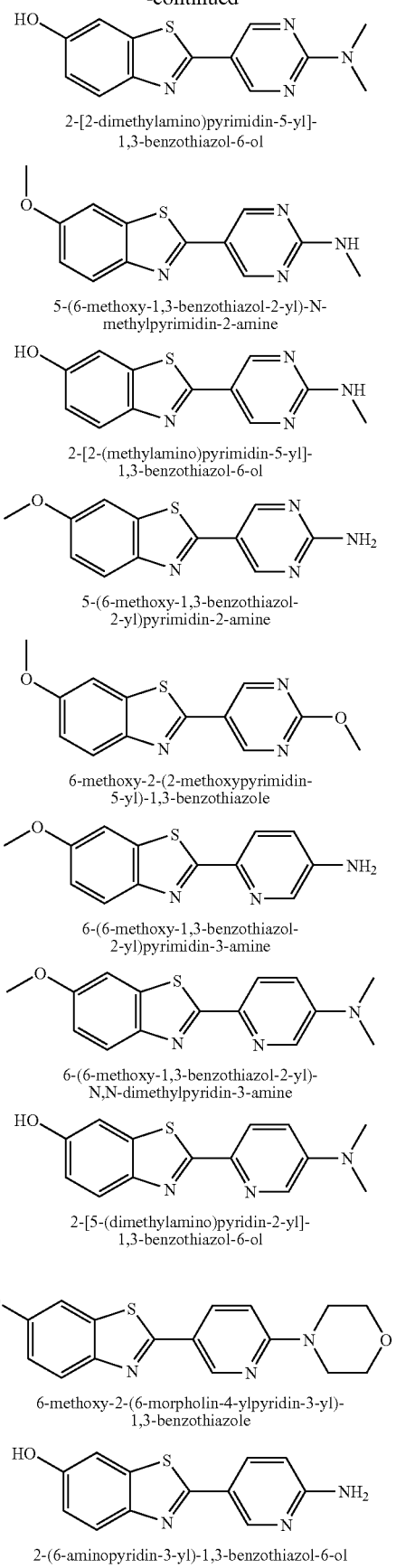

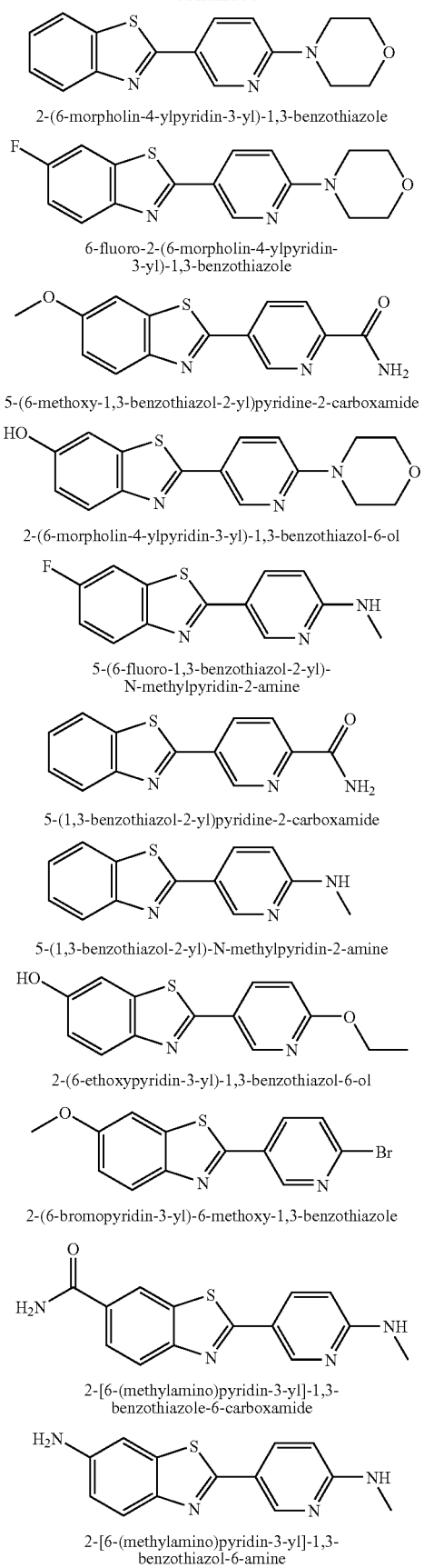

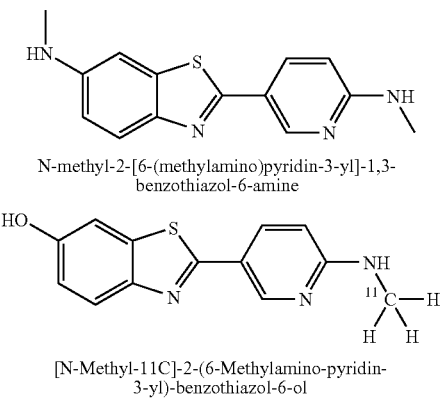

In another aspect of the invention, there is provided a compound according to formula I, wherein $X_4$ of formula I is a carbon atom substituted with fluoro or iodo.

In another aspect of the invention, there is provided a compound according to formula I, wherein R3 of formula I is selected from $SO_2C_{1-6}$ alkyl, $SC_{1-6}$ alkyl, $SC_{1-6}$ fluoroalkyl and $N(C_{4-6}$ alkylene).

In another aspect of the invention, there is provided a compound according to formula I, wherein R1 and R2 together forms a ring;

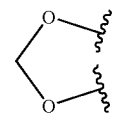

In another aspect of the invention, there is provided a compound according to formula I, said compound being:

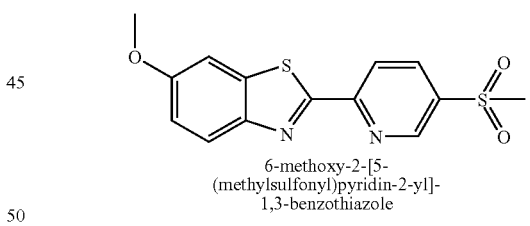

6-methoxy-2-[5-(methylsulfonyl)pyridin-2-yl]-1,3-benzothiazole

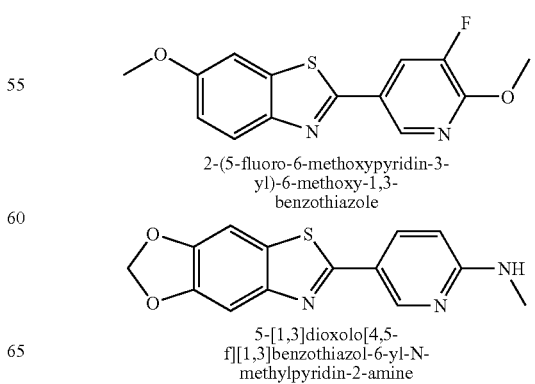

2-(5-fluoro-6-methoxypyridin-3-yl)-6-methoxy-1,3-benzothiazole

5-[1,3]dioxolo[4,5-f][1,3]benzothiazol-6-yl-N-methylpyridin-2-amine

-continued

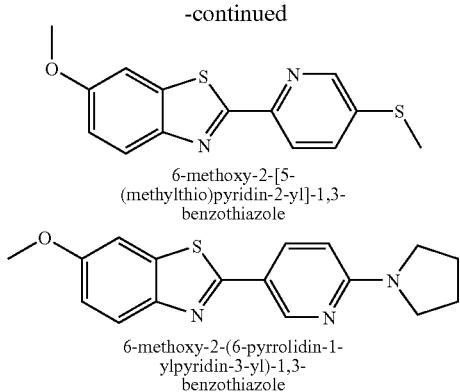

6-methoxy-2-[5-(methylthio)pyridin-2-yl]-1,3-benzothiazole 6-methoxy-2-(6-pyrrolidin-1-ylpyridin-3-yl)-1,3-benzothiazole In another aspect of the invention, there is provided a compound according to formula I, wherein one to three of the atoms represents a detectable isotope selected from $^3$H, $^{19}$F and $^{13}$C, or wherein one of the atoms is a detectable isotope selected from $^{18}$F, $^{11}$C and $^{14}$C.

In another aspect of the invention, there is provided a compound according to formula I, wherein one or more of the, atoms of R1 is a radiolabeled atom.

In another aspect of the invention, there is provided a compound according to formula I, wherein one or more of the atoms of R2 is a radiolabeled atom.

In another aspect of the invention, there is provided a compound according to formula I, wherein one or more of the atoms of R3 is a radiolabeled atom.

In another aspect of the invention, there is provided a compound according to formula I, wherein said radiolabeled atom is selected from $^3$H, $^{18}$F, $^{19}$F, $^{11}$C, $^{13}$C, $^{14}$C, $^{75}$Br, $^{76}$Br, $^{120}$I, $^{123}$I, $^{125}$I and $^{131}$I.

In another aspect of the invention, there is provided a compound according to formula I, wherein said radiolabeled atom is selected from $^3$H, $^{18}$F, $^{19}$F, $^{11}$C, $^{14}$C and $^{123}$I.

In another aspect of the invention, there is provided a compound according to formula I, wherein said radiolabeled atom is selected from $^{18}$F and $^{11}$C.

In another aspect of the invention, there is provided a compound according to formula VII

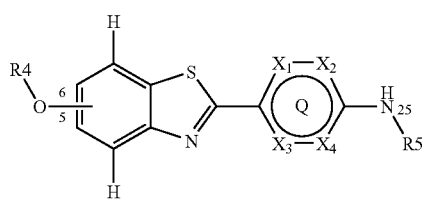

VII wherein
O—R4 residue is attached to position 6, and a hydrogen atom is attached to position 5 of the benzothiazole ring;
R4 is selected from Si(G3)$_3$, CH$_2$G4, tetrahydropyranyl, 1-ethoxyethyl, phenacyl, 4-bromophenacyl, cyclohexyl, t-butyl, t-butoxycarbonyl, 2,2,2-trichloroethylcarbonyl and triphenylmethyl;
G3 is, independently of each other, selected from C$_{1-4}$ alkyl and phenyl;
G4 is selected from 2-(trimethylsilyl)ethoxy, C$_{1-3}$ alkoxy, 2-(C$_{1-3}$ alkoxy)ethoxy, C$_{1-3}$ alkylthio, cyclopropyl, vinyl, phenyl, p-methoxyphenyl, o-nitrophenyl, and 9-anthryl;

Q is a 6-membered aromatic heterocycle containing either one or two N-atoms, wherein $X_1$, $X_2$, $X_3$ and $X_4$ are independently selected from N or C, and wherein one or two of $X_1$, $X_2$, $X_3$ and $X_4$ is N and the remaining is C;
R5 is selected from C$_{1-3}$ alkyl and hydrogen;
as a free base or a salt, solvate or solvate of a salt thereof.

In another aspect of the invention, there is provided a compound according to formula VII, wherein R4 is Si(G3)$_3$.

In another aspect of the invention, there is provided a compound according to formula VII, wherein R4 is selected from t-butyldimethylsilyl, 2-(trimethylsilyl)ethoxymethyl and ethoxymethyl.

In another aspect of the invention, there is provided a compound according to formula VII, wherein R4 is selected from t-butyldimethylsilyl and ethoxymethyl.

In another aspect of the invention, there is provided a compound according to formula VII, wherein R4 is t-butyldimethylsilyl.

In another aspect of the invention, there is provided a compound according to formula VII, Q is a pyrimidine ring, wherein $X_2$ and $X_4$ are N, and $X_1$ and $X_3$ are C.

In another aspect of the invention, there is provided a compound according to formula VII, Q is a pyridine ring, wherein $X_2$ is N, and $X_1$, $X_3$ and $X_4$ are C.

In another aspect of the invention, there is provided a compound according to formula VII, wherein Q is a pyridine ring, wherein $X_4$ is N, and $X_1$, $X_2$ and $X_3$ are C.

In another aspect of the invention, there is provided a compound according to formula VII, wherein R5 is hydrogen.

In another aspect of the invention, there is provided a compound according to formula VII, said compound being:

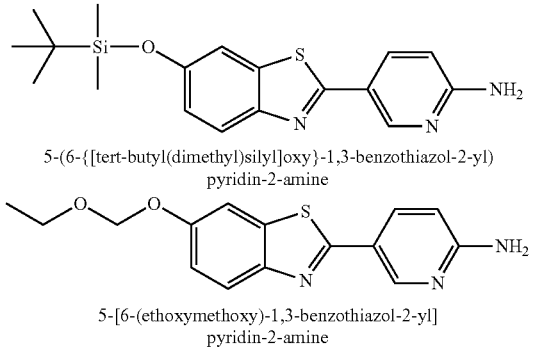

5-(6-{[tert-butyl(dimethyl)silyl]oxy}-1,3-benzothiazol-2-yl)pyridin-2-amine

5-[6-(ethoxymethoxy)-1,3-benzothiazol-2-yl]pyridin-2-amine

In another aspect of the invention, there is provided use of a compound according to formula VII as synthetic precursor in a process of preparation of a labeled compound of formula XIV

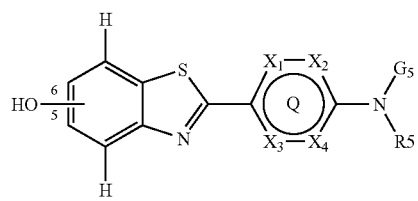

XIV wherein
OH is attached to position 6, and a hydrogen atom is attached to position 5 of the benzothiazole ring;

Q is a 6-membered aromatic heterocycle containing either one or two N-atoms, wherein $X_1$, $X_2$, $X_3$ and $X_4$ are independently selected from N or C, and wherein one or two of $X_1$, $X_2$, $X_3$ and $X_4$ is N and the remaining is C;

R5 is selected from $C_{1-3}$ alkyl and hydrogen;

G5 is selected from $C_{1-3}$ alkyl and $C_{1-3}$ fluoroalkyl, wherein one to three of the atoms of G5 is a detectable isotope selected from $^3H$, $^{19}F$ and $^{13}C$, or wherein one of the atoms of G5 is is detectable isotope selected from $^{18}F$, $^{11}C$ and $^{14}C$.

In another aspect of the invention, there is provided a pharmaceutical composition comprising a compound according to formula I, together with a pharmaceutically acceptable carrier.

In another aspect of the invention, there is provided a pharmaceutical composition for in vivo imaging of amyloid deposits, comprising a radio-labeled compound according to formula I, together with a pharmaceutically acceptable carrier.

In another aspect of the invention, there is provided an in vivo method for measuring amyloid deposits in a subject, comprising the steps of: (a) administering a detectable quantity of a pharmaceutical composition comprising a radio-labeled compound of formula I, and detecting the binding of the compound to amyloid deposit in the subject. Said detection may be carried out by gamma imaging, magnetic resonance imaging or magnetic resonance spectroscopy. Said subject may be suspected of having a disease or syndrome selected from the group consisting of Alzheimer's Disease, familial Alzheimer's Disease, Down's Syndrome and homozygotes for the apolipoprotein E4 allele.

In another aspect of the invention, there is provided a compound of formula I for use in therapy.

In another aspect of the invention, there is provided use of a compound of formula I in the manufacture of a medicament for prevention and/or treatment of Alzheimer's Disease, familial Alzheimer's Disease, Cognitive Deficit in Schizophrenia (CDS), Down's Syndrome and homozygotes for the apolipoprotein E4 allele.

In another aspect of the invention, there is provided use of a compound of formula I in the manufacture of a medicament for prevention and/or treatment of Alzheimer's Disease.

In another aspect of the invention, there is provided use of a compound of formula I in the manufacture of a medicament for prevention and/or treatment of Cognitive Deficit in Schizophrenia (CDS).

In another aspect of the invention, there is provided a method of prevention and/or treatment of Alzheimer's Disease, familial Alzheimer's Disease, Down's Syndrome and homozygotes for the apolipoprotein E4 allele, comprising administering to a mammal, including man in need of such prevention and/or treatment, a therapeutically effective amount of a compound of formula I.

In another aspect of the invention, there is provided a method of prevention and/or treatment of Alzheimer's Disease, comprising administering to a mammal, including man in need of such prevention and/or treatment, a therapeutically effective amount of a compound of formula I.

In another aspect of the invention, there is provided a method of prevention and/or treatment of Cognitive Deficit in Schizophrenia (CDS), comprising administering to a mammal, including man in need of such prevention and/or treatment, a therapeutically effective amount of a compound of formula I.

DEFINITIONS

As used herein, "alkyl", "alkylenyl" or "alkylene" used alone or as a suffix or prefix, is intended to include both branched and straight chain saturated aliphatic hydrocarbon groups having from 1 to 12 carbon atoms or if a specified number of carbon atoms is provided then that specific number would be intended. For example "$C_{1-6}$ alkyl" denotes alkyl having 1, 2, 3, 4, 5 or 6 carbon atoms. When the specific number denoting the alkyl-group is the integer 0 (zero), a hydrogen-atom is intended as the substituent at the position of the alkyl-group. For example, "$N(C_0$ alkyl$)_2$" is equivalent to "$NH_2$" (amino). When the specific number denoting the alkylenyl or alkylene-group is the integer 0 (zero), a bond is intended to link the groups onto which the alkylenyl or alkylene-group is substituted. For example, "$NH(C_0$ alkylene)$NH_2$" is equivalent to "$NHNH_2$" (hydrazino). As used herein, the groups linked by an alkylene or alkylenyl-group are intended to be attached to the first and to the last carbon of the alkylene or alkylenyl-group. In the case of methylene, the first and the last carbon is the same. For example, "$N(C_4$ alkylene)", "$N(C_5$ alkylene)" and "$N(C_2$ alkylene$)_2NH$" is equivalent to pyrrolidinyl, piperidinyl and piperazinyl, respectively.

Examples of alkyl include, but are not limited to, methyl, ethyl, n-propyl, i-propyl, n-butyl, i-butyl, sec-butyl, t-butyl, pentyl, and hexyl.

Examples of alkylene or alkylenyl include, but are not limited to, methylene, ethylene, propylene, and butylene.

As used herein, "alkoxy" or "alkyloxy" represents an alkyl group as defined above with the indicated number of carbon atoms attached through an oxygen bridge. Examples of alkoxy include, but are not limited to, methoxy, ethoxy, n-propoxy, isopropoxy, n-butoxy, isobutoxy, t-butoxy, n-pentoxy, isopentoxy, cyclopropylmethoxy, allyloxy and propargyloxy. Similarly, "alkylthio" or "thioalkoxy" represent an alkyl group as defined above with the indicated number of carbon atoms attached through a sulphur bridge.

As used herein, "fluoroalkyl", "fluoroallklene" and "fluoroalkoxy", used alone or as a suffix or prefix, refers to groups in which one, two, or three of the hydrogen(s) attached to the carbon(s) of the corresponding alkyl, alkylene and alkoxy-groups are replaced by fluoro. Examples of fluoroalkyl include, but are not limited to, trifluoromethyl, difluoromethyl, fluoromethyl, 2,2,2-trifluoroethyl, 2-fluoroethyl and 3-fluoropropyl.

Examples of fluoroalkylene include, but are not limited to, difluoromethylene, fluoromethylene, 2,2-difluorobutylene and 2,2,3-trifluorobutylene.

Examples of fluoroalkoxy include, but are not limited to, trifluoromethoxy, 2,2,2-trifluoroethoxy, 3,3,3-trifluoropropoxy and 2,2-difluoropropoxy.

As used herein, "aromatic" refers to hydrocarbonyl groups having one or more unsaturated carbon ring(s) having aromatic characters, (e.g. 4n+2 delocalized electrons) and comprising up to about 14 carbon atoms. In addition "heteroaromatic" refers to groups having one or more unsaturated rings containing carbon and one or more heteroatoms such as nitrogen, oxygen or sulphur having aromatic character (e.g. 4n+2 delocalized electrons).

As used herein, the term "aryl" refers to an aromatic ring structure made up of from 5 to 14 carbon atoms. Ring structures containing 5, 6, 7 and 8 carbon atoms would be single-ring aromatic groups, for example, phenyl. Ring structures containing 8, 9, 10, 11, 12, 13, or 14 would be polycyclic, for example naphthyl. The aromatic ring can be substituted at one or more ring positions with such substituents as described above. The term "aryl" also includes polycyclic ring systems having two or more cyclic rings in which two or more carbons are common to two adjoining rings (the rings are "fused rings") wherein at least one of the rings is aromatic, for example, the other cyclic rings can be cycloalkyls, cycloalkenyls, cycloalkynyls, aryls and/or heterocyclyls. The terms ortho, meta and para apply to 1,2-, 1,3- and 1,4-disubstituted benzenes, respectively. For example, the names 1,2-dimethylbenzene and ortho-dimethylbenzene are synonymous.

As used herein, the term "cycloalkyl" is intended to include saturated ring groups, having the specified number of carbon atoms. These may include fused or bridged polycyclic systems. Preferred cycloalkyls have from 3 to 10 carbon atoms in their ring structure, and more preferably have 3, 4, 5, and 6 carbons in the ring structure. For example, "$C_{3-6}$ cycloalkyl" denotes such groups as cyclopropyl, cyclobutyl, cyclopentyl, or cyclohexyl.

As used herein, "halo" or "halogen" refers to fluoro, chloro, bromo, and iodo. "Counterion" is used, for example, to represent a small, negatively charged species such as chloride, bromide, hydroxide, acetate, sulfate, tosylate, benezensulfonate, and the like.

As used herein, the term "heterocyclyl" or "heterocyclic" or "heterocycle" refers to a saturated, unsaturated or partially saturated, monocyclic, bicyclic or tricyclic ring (unless otherwise stated) containing 3 to 20 atoms of which 1, 2, 3, 4 or 5 ring atoms are chosen from nitrogen, sulphur or oxygen, which may, unless otherwise specified, be carbon or nitrogen linked, wherein a —$CH_2$— group is optionally be replaced by a —C(O)—; and where unless stated to the contrary a ring nitrogen or sulphur atom is optionally oxidised to form the N-oxide or S-oxide(s) or a ring nitrogen is optionally quarternized; wherein a ring —NH is optionally substituted by acetyl, formyl, methyl or mesyl; and a ring is optionally substituted by one or more halo. It is understood that when the total number of S and O atoms in the heterocyclyl exceeds 1, then these heteroatoms are not adjacent to one another. If the said heterocyclyl group is bi- or tricyclic then at least one of the rings may optionally be a heteroaromatic or aromatic ring provided that at least one of the rings is non-heteroaromatic. If the said heterocyclyl group is monocyclic then it must not be aromatic. Examples of heterocyclyls include, but are not limited to, piperidinyl, N-acetylpiperidinyl, N-methylpiperidinyl, N-formylpiperazinyl, N-mesylpiperazinyl, homopiperazinyl, piperazinyl, azetidinyl, oxetanyl, morpholinyl, tetrahydroisoquinolinyl, tetrahydroquinolinyl, indolinyl, tetrahydropyranyl, dihydro-2H-pyranyl, tetrahydrofuranyl and 2,5-dioxoimidazolidinyl.

As used herein, "heteroaryl" refers to a heteroaromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl (i.e., pyridinyl), pyrimidinyl, pyrazinyl, pyridazinyl, triazinyl, furyl (i.e. furanyl), quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 4 to about 14, 3 to about 7, or 5 to 6 ring-forming atoms. In some embodiments, the heteroaryl group has 1 to about 4, 1 to about 3, or 1 to 2 heteroatoms. In some embodiments, the heteroaryl group has 1 heteroatom.

As used herein, the phrase "protecting group" or "protective group" means temporary substituents which protect a potentially reactive functional group from undesired chemical transformations. Examples of such protecting groups include esters of carboxylic acids, silyl ethers of alcohols, and acetals and ketals of aldehydes and ketones respectively. A sub-group of protecting groups are those which protect a nucleophilic hydroxy group against alkylation and thus permit selective N-alkylation of an amino-group present in the same molecule under basic conditions. Examples of such protecting groups include, but is not limited to, methyl, 2-(trimethylsilyl)ethoxymethyl, alkoxymethyl and t-butyldimethylsilyl.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, phosphoric, and the like; and the salts prepared from organic acids such as lactic, maleic, citric, benzoic, methanesulfonic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are used.

As used herein, "in vivo hydrolysable precursors" means an in vivo hydrolysable (or cleavable) ester of a compound of formula I that contains a carboxy or a hydroxy group. For example amino acid esters, $C_{1-6}$ alkoxymethyl esters like methoxymethyl; $C_{1-6}$alkanoyloxymethyl esters like pivaloyloxymethyl; $C_{3-8}$cycloalkoxycarbonyloxy $C_{1-6}$alkyl esters like 1-cyclohexylcarbonyloxyethyl, acetoxymethoxy, or phosphoramidic cyclic esters.

As used herein, "tautomer" means other structural isomers that exist in equilibrium resulting from the migration of a hydrogen atom. For example, keto-enol tautomerism where the resulting compound has the properties of both a ketone and an unsaturated alcohol.

As used herein "stable compound" and "stable structure" are meant to indicate a compound that is sufficiently robust to survive isolation to a useful degree of purity from a reaction mixture, and formulation into an efficacious therapeutic or diagnostic agent.

Compounds of the invention further include hydrates and solvates.

The present invention includes isotopically labeled compounds of the invention. An "isotopically-labeled", "radiolabeled", "labeled", "detectable" or "detectable amyloid binding" compound, or a "radioligand" is a compound of the invention where one or more atoms are replaced or substituted by an atom having an atomic mass or mass number different from the atomic mass or mass number typically found in nature (i.e., naturally occurring). Suitable radionuclides (i.e. "detectable isotopes") that may be incorporated in compounds of the present invention include but are not limited to $^{2}$H (also written as D for deuterium), $^{3}$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. It is to be understood that an isotopically labeled compound of the invention need only to be enriched with a detectable isotop to, or above, the degree which allows detection with a technique suitable for the particular application, e.g. in a detectable compound of the invention labeled with $^{11}$C, the carbon-atom of the labeled group of the labeled compound may be constituted by $^{12}$C or other carbon-isotopes in a fraction of the molecules. The radionuclide that is incorporated in the instant radiolabeled compounds will depend on the specific application of that radiolabeled compound. For example, for in vitro plaque or receptor labeling and competition assays, compounds that incorporate $^{3}$H, $^{14}$C, or $^{125}$I will generally be most useful. For in vivo imaging applications $^{11}$C, $^{13}$C, $^{18}$F, $^{19}$F, $^{120}$I, $^{123}$I, $^{131}$I, $^{75}$Br, or $^{76}$Br will generally be most useful.

In one embodiment of the invention the radionuclides are represented by $^{3}$H, $^{18}$F, $^{19}$F, $^{11}$C, $^{13}$C, $^{14}$C, $^{75}$Br, $^{76}$Br, $^{120}$I, $^{123}$I, $^{125}$I or $^{131}$I.

Examples of an "effective amount" include amounts that enable imaging of amyloid deposit(s) in vivo, that yield acceptable toxicity and bioavailability levels for pharmaceutical use, and/or prevent cell degeneration and toxicity associated with fibril formation.

This invention provides radiolabeled heteroaryl substituted benzothiazoles as amyloid imaging agents and synthetic precursor compounds from which such are prepared.

It is believed that the compounds of the present invention may be used for the treatment of Alzheimer disease. Hence, compounds of the present invention and their salts are expected to be active against age-related diseases such as Alzheimer, as well as other AD related pathologies such as Downs syndrome and β-amyloid angiopathy. It is expected that the compounds of the present invention would most likely be used as single agents but could also be used in combination with a broad range of cognition deficit enhancement agents.

In one embodiment of the present invention, there is provided a compound of formula (I) or a pharmaceutically acceptable salt, solvate or in vivo hydrolysable ester thereof, or a pharmaceutical composition or formulation comprising a compound of formula (I) is administered concurrently, simultaneously, sequentially or separately with another pharmaceutically active compound or compounds used in Alzheimer's therapies including for example donepezil, memantine, tacrine and equivalents and pharmaceutically active isomer(s) and metabolite(s) thereof.

Methods of Use

The compounds of the present invention may be used to determine the presence, location and/or amount of one or more amyloid deposit(s) in an organ or body area, including the brain, of an animal. Amyloid deposit(s) include, without limitation, deposit(s) of Aβ. In allowing the temporal sequence of amyloid deposition to be followed, the inventive compounds may further be used to correlate amyloid deposition with the onset of clinical symptoms associated with a disease, disorder or condition. The inventive compounds may ultimately be used to treat, and to diagnose a disease, disorder or condition characterized by amyloid deposition, such as AD, familial AD, Down's syndrome, amyloidosis and homozygotes for the apolipoprotein E4 allele.

The method of this invention determines the presence and location of amyloid deposits in an organ or body area, preferably brain, of a patient. The present method comprises administration of a detectable quantity of a pharmaceutical composition containing an amyloid-binding compound of the present invention called a "detectable compound," or a pharmaceutically acceptable water-soluble salt thereof, to a patient. A "detectable quantity" means that the amount of the detectable compound that is administered is sufficient to enable detection of binding of the compound to amyloid. An "imaging effective quantity" means that the amount of the detectable compound that is administered is sufficient to enable imaging of binding of the compound to amyloid.

The invention employs amyloid probes which, in conjunction with non-invasive neuroimaging techniques such as magnetic resonance spectroscopy (MRS) or imaging (MINI), or gamma imaging such as positron emission tomography (PET) or single-photon emission computed tomography (SPECT), are used to quantify amyloid deposition in vivo. The term "in vivo imaging" refers to any method which permits the detection of a labeled heteroaryl substituted benzothiazole derivative as described herein. For gamma imaging, the radiation emitted from the organ or area being examined is measured and expressed either as total binding or as a ratio in which total binding in one tissue is normalized to (for example, divided by) the total binding in another tissue of the same subject during the same in vivo imaging procedure. Total binding in vivo is defined as the entire signal detected in a tissue by an in vivo imaging technique without the need for correction by a second injection of an identical quantity of labeled compound along with a large excess of unlabeled, but otherwise chemically identical compound. A "subject" is a mammal, preferably a human, and most preferably a human suspected of having dementia.

For purposes of in vivo imaging, the type of detection instrument available is a major factor in selecting a given label. For instance, radioactive isotopes and $^{19}$F are particularly suitable for in vivo imaging in the methods of the present invention. The type of instrument used will guide the selection of the radionuclide or stable isotope. For instance, the radionuclide chosen must have a type of decay detectable by a given type of instrument.

Another consideration relates to the half-life of the radionuclide. The half-life should be long enough so that it is still detectable at the time of maximum uptake by the target, but short enough so that the host does not sustain deleterious radiation. The radiolabeled compounds of the invention can be detected using gamma imaging wherein emitted gamma irradiation of the appropriate wavelength is detected. Methods of gamma imaging include, but are not limited to, SPECT and PET. Preferably, for SPECT detection, the chosen radiolabel will lack a particulate emission, but will produce a large number of photons in a 140-200 keV range.

For PET detection, the radiolabel will be a positron-emitting radionuclide such as $^{18}$F which will annihilate to form two 511 keV gamma rays which will be detected by the PET camera.

In the present invention, amyloid binding compounds/probes are made which are useful for in vivo imaging and quantification of amyloid deposition. These compounds are to be used in conjunction with non-invasive neuroimaging techniques such as magnetic resonance spectroscopy (MRS) or imaging (MRI), positron emission tomography (PET), and single-photon emission computed tomography (SPECT). In accordance with this invention, the heteroaryl substituted benzothiazole derivatives may be labeled with $^{19}$F or $^{13}$C for MRS/MRI by general organic chemistry techniques known in the art. The compounds may also be radiolabeled with $^{18}$F, $^{11}$C, $^{75}$Br, $^{76}$Br, or $^{120}$I for PET by techniques well known in the art and are described by Fowler, J. and Wolf, A. in POSITRON EMISSION TOMOGRAPHY AND AUTORADIOGRAPHY 391-450 (Raven Press, 1986). The compounds also may be radiolabeled with $^{123}$I and $^{131}$I for SPECT by any of several techniques known to the art. See, e.g., Kulkarni, Int. J. Rad. Appl. & Inst. (Part B) 18: 647 (1991). The compounds may also be radiolabeled with known metal radiolabels, such as Technetium-99m ($^{99m}$Tc). Modification of the substituents to introduce ligands that bind such metal ions can be effected without undue experimentation by one of ordinary skill in the radiolabeling art. The metal radiolabeled compound can then be used to detect amyloid deposits. Preparing radiolabeled derivatives of Tc-99m is well known in the art. See, for example, Zhuang et al. Nuclear Medicine & Biology 26(2):217-24, (1999); Oya et al. Nuclear Medicine & Biology 25(2):135-40, (1998), and Hom et al. Nuclear Medicine & Biology 24(6):485-98, (1997). In addition, the compounds may be labeled with $^3$H, $^{14}$C and 125, by methods well known to the one skilled in the art, for detection of amyloid plaque in in vitro and post mortem samples.

The methods of the present invention may use isotopes detectable by nuclear magnetic resonance spectroscopy for purposes of in vivo imaging and spectroscopy. Elements particularly useful in magnetic resonance spectroscopy include $^{19}$F and $^{13}$C.

Suitable radioisotopes for purposes of this invention include beta-emitters, gamma-emitters, positron-emitters, and x-ray emitters. These radioisotopes include $^{120}$I, $^{123}$I, $^{131}$I, $^{125}$I, $^{18}$F, $^{11}$C, $^{75}$Br, and $^{76}$Br. Suitable stable isotopes for use in Magnetic Resonance Imaging (MRI) or Spectroscopy (MRS), according to this invention, include $^{19}$F and $^{13}$C. Suitable radioisotopes for in vitro quantification of amyloid in homogenates of biopsy or post-mortem tissue include $^{125}$I, $^{14}$C, and $^3$H. The preferred radiolabels are $^{11}$C or $^{18}$F for use in PET in vivo imaging, $^{123}$I for use in SPECT imaging, $^{19}$F for MRS/MRI, and $^3$H or $^{14}$C for in vitro studies. However, any conventional method for visualizing diagnostic probes can be utilized in accordance with this invention.

The compounds of the present invention may be administered by any means known to one of ordinary skill in the art. For example, administration to the animal may be local or systemic and accomplished orally, parenterally, by inhalation spray, topically, rectally, nasally, buccally, vaginally, or via an implanted reservoir. The term "parenteral" as used herein includes subcutaneous, intravenous, intraarterial, intramuscular, intraperitoneal, intrathecal, intraventricular, intrasternal, intracranial, and intraosseous injection and infusion techniques.

The exact administration protocol will vary depending upon various factors including the age, body weight, general health, sex and diet of the patient; the determination of specific administration procedures would be routine to an one of ordinary skill in the art.

Dose levels on the order of about 0.001 μg/kg/day to about 10,000 mg/kg/day of an is inventive compound are useful for the inventive methods. In one embodiment, the dose level is about 0.001 μg/kg/day to about 10 g/kg/day. In another embodiment, the dose level is about 0.01 μg/kg/day to about 1.0 g/kg/day. In yet another embodiment, the dose level is about 0.1 mg/kg/day to about 100 mg/kg/day.

The specific dose level for any particular patient will vary depending upon various factors, including the activity and the possible toxicity of the specific compound employed; the age, body weight, general health, sex and diet of the patient; the time of administration; the rate of excretion; the drug combination; and the form of administration. Typically, in vitro dosage-effect results provide useful guidance on the proper doses for patient administration. Studies in animal models are also helpful. The considerations for determining the proper dose levels are well known in the art and within the skills of an ordinary physician.

Any known administration regimen for regulating the timing and sequence of drug delivery may be used and repeated as necessary to effect treatment in the inventive methods.

The regimen may include pretreatment and/or co-administration with additional therapeutic agent(s).

In one embodiment, the inventive compounds are administered to a mammal, including man, that is suspected of having or that is at risk of developing a disease, disorder or condition characterized by amyloid deposition. For example, the animal may be an elderly human.

In another embodiment, compounds and methods for their preparation, useful as precursors, are provided. Such precursors may be used as synthetic starting materials for the incorporation of labeled molecular fragments leading to radiolabeled heteroaryl substituted benzothiazoles as amyloid imaging agents.

Method for Detecting Amyloid Deposits In Vitro

This invention further provides a method for detecting amyloid deposit(s) in vitro comprising: (i) contacting a bodily tissue with an effective amount of an inventive compound, wherein the compound would bind any amyloid deposit(s) in the tissue; and (ii) detecting binding of the compound to amyloid deposit(s) in the tissue.

The binding may be detected by any means known in the art. Examples of detection means include, without limitation, microscopic techniques, such as bright-field, fluorescence, laser-confocal and cross-polarization microscopy.

Pharmaceutical Compositions

This invention further provides a pharmaceutical composition comprising: (i) an effective amount of at least one inventive compound; and (ii) a pharmaceutically acceptable carrier.

The composition may comprise one or more additional pharmaceutically acceptable ingredient(s), including without limitation one or more wetting agent(s), buffering agent(s), suspending agent(s), lubricating agent(s), emulsifier(s), disintegrant(s), absorbent(s), preservative(s), surfactant(s), colorant(s), flavorant(s), sweetener(s) and therapeutic agent(s).

The composition may be formulated into solid, liquid, gel or suspension form for: (1) oral administration as, for example, a drench (aqueous or non-aqueous solution or suspension), tablet (for example, targeted for buccal, sublingual or systemic absorption), bolus, powder, granule, paste for application to the tongue, hard gelatin capsule, soft gelatin capsule, mouth spray, emulsion and microemulsion; (2) parenteral administration by subcutaneous, intramuscular, intravenous or epidural injection as, for example, a sterile solution, suspension or sustained-release formulation; (3) topical application as, for example, a cream, ointment, controlled-release patch or spray applied to the skin; (4) intravaginal or intrarectal administration as, for example, a pessary, cream or foam; (5) sublingual administration; (6) ocular administration; (7) transdermal administration; or (8) nasal administration.

In one embodiment, the composition is formulated for intravenous administration and the carrier includes a fluid and/or a nutrient replenisher. In another embodiment, the composition is capable of binding specifically to amyloid in vivo, is capable of crossing the blood-brain barrier, is non-toxic at appropriate dose levels and/or has a satisfactory duration of effect. In yet another embodiment, the composition comprises about 10 mg of human serum albumin and from about 0.0005 to 500 mg of a compound of the present invention per mL of phosphate buffer containing NaCl.

The present invention further provides compositions comprising a compound of formula I, and at least one pharmaceutically acceptable carrier, diluent or excipient.

The present invention further provides methods of treating or preventing an AD-related pathology in a patient, comprising administering to the patient a therapeutically effective amount of a compound of formula I.

The present invention further provides a compound of formula I for use as a medicament.

The present invention further provides a compound of formula I for the manufacture of a medicament.

Some compounds of formula I may have stereogenic centres and/or geometric isomeric centres (E- and Z-isomers), and it is to be understood that the invention encompasses all such optical isomers, enantiomers, diastereoisomers, atropisomers and geometric isomers.

The present invention relates to the use of compounds of formula I as hereinbefore defined as well as to the salts thereof. Salts for use in pharmaceutical compositions will be pharmaceutically acceptable salts, but other salts may be useful in the production of the compounds of formula I.

Compounds of the invention can be used as medicaments. In some embodiments, the present invention provides compounds of formula I, or pharmaceutically acceptable salts, tautomers or in vivo-hydrolysable precursors thereof, for use as medicaments. In some embodiments, the present invention provides compounds described here in for use as medicaments for treating or preventing an AD-related pathology. In some further embodiments, the AD-related pathology is Downs syndrome, a β-amyloid angiopathy, cerebral amyloid angiopathy, hereditary cerebral hemorrhage, a disorder associated with cognitive impairment, MCI ("mild cognitive impairment"), Alzheimer Disease, memory loss, attention deficit symptoms associated with Alzheimer disease, neurodegeneration associated with Alzheimer disease, dementia of mixed vascular origin, dementia of degenerative origin, presenile dementia, senile dementia, dementia associated with Parkinson's disease, progressive supranuclear palsy or cortical basal degeneration.

The invention further relates to therapies for the treatment of:

Neurodegenerative Disorder(s) including but not limited to Dementia, Cognitive Deficit in Schizophrenia (CDS), Mild Cognitive Impairment (MCI), Age-Associated Memory Impairment (AAMI), Age-Related Cognitive Decline (ARCD), Cognitive Impairment No Dementia (CIND), Multiple Sclerosis, Parkinson's Disease (PD), postencephalitic parkinsonism, Huntington's Disease, amyotrophic lateral sclerosis (ALS), motor neuron diseases (MND), Multiple System Atrophy (MSA), Corticobasal Degeneration, Progressive Supranuclear Paresis, Guillain-Barré Syndrome (GBS), and Chronic Inflammatory Demyelinating Polyneuropathy (CIDP). Dementia includes, but is not limited to, Down syndrome, vascular dementia, dementia with Lewy bodies, HIV dementia, Frontotemporal dementia Parkinson's Type (FTDP), Pick's Disease, Niemann-Pick's Disease, traumatic brain injury (TBI), dementia pugilistica, Creutzfeld-Jacob Disease and prion diseases.

Methods of Preparation

The present invention also relates to processes for preparing the compound of formula I as a free base, acid, or pharmaceutically acceptable salts thereof. Throughout the following description of such processes it is to be understood that, where appropriate, suitable protecting groups will be added to, and subsequently removed from, the various reactants and intermediates in a manner that will be readily understood by one skilled in the art of organic synthesis. Conventional procedures for using such protecting groups as well as is examples of suitable protecting groups are described, for example, in "Protective Groups in Organic Synthesis", T. W. Green, P. G. M. Wuts, Wiley-Interscience, New York, (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to the one skilled in the art of organic synthesis. Examples of transformations are given below, and it is to be understood that the described transformations are not limited only to the generic groups or substituents for which the transformations are exemplified. References and descriptions on other suitable transformations are given in "Comprehensive Organic Transformations—A Guide to Functional Group Preparations" R. C. Larock, VHC Publishers, Inc. (1989). References and descriptions of other suitable reactions are described in textbooks of organic chemistry, for example, "Advanced Organic Chemistry", March 4th ed. McGraw Hill (1992) or, "Organic Synthesis", Smith, McGraw Hill, (1994). Techniques for purification of intermediates and final products include for example, straight and reversed phase chromatography on column or rotating plate, recrystallisation, distillation and liquid-liquid or solid-liquid extraction, which will be readily understood by the one skilled in the art. The definitions of substituents and groups are as in formula I except where defined differently. The terms "room temperature" and "ambient temperature" shall mean, unless otherwise specified, a temperature between 16 and 25° C. The term "reflux" shall mean, unless otherwise stated, in reference to an employed solvent using a temperature at or slightly above the boiling point of the named solvent. It is understood that microwaves can be used for the heating of reaction mixtures. The terms "flash chromatography" or "flash column chromatography" shall mean preparative chromatography on silica using an organic solvent, or mixtures thereof, as mobile phase.

| Abbreviations | |
|---|---|
| atm | atmosphere; |
| aq. | aqueous; |
| BINAP | 2,2'-bis(diphenylphosphino)-1,1'-binaphtyl |
| DBA | dibenzylideneacetone; |
| DCM | dichloromethane; |
| DME | 1,2-dimethoxyethane; |
| DMF | dimethylformamide; |
| DMSO | dimethyl sulfoxide; |
| dppf | 1,1'-bis(diphenylphosphino)ferrocene; |
| EA | ethyl acetate; |
| EtOAc | ethyl acetate; |
| EtOH | ethanol; |
| h | hour; |
| hep | heptane; |
| hex | hexane(s); |
| LAH | lithium aluminumhydride; |
| MeCN | acetonitrile; |
| MeOH | methanol; |
| min | minutes; |
| NaHMDS | sodium hexamethyl disilazide; |
| o.n. or on | over night; |
| Pd(dppf)Cl$_2$ * DCM or Pd(dppf)Cl$_2$ * CH$_2$Cl$_2$: | (1,1'-bis(diphenylphosphino)ferrocene)palladium (II) chloride dichloromethane adduct; |
| prep. HPLC | preparative HPLC; |
| r.t. or rt | room temperature; |
| r.m. | reaction mixture; |
| sat. | saturated; |
| TBAF | tetra-N-butylammonium fluoride |
| TBDMS | tert-butyldimethylsilyl; |

| Abbreviations | |
|---|---|
| TFA | trifluoroacetic acid; |
| THF | tetrahydrofurane; |
| NEt$_3$ | triethylamine; |
| Otf | thiomethyl. |

Preparation of Intermediates

Compounds of formula II, III, IV V and VI are useful intermediates in the preparation of compound of formula I. R1, R2, R3, and X1 to X4 are defined as in formula I. Compounds of formula II-VI are either commercially available, or can be prepared from either commercially available, or in the literature described compounds. For example, compounds in which one or more of Y1, Y2, Y3, Y4, R1, R2 and R3 does not correspond to the definitions of formula II-VI, can be used for the preparation of compounds of formula II-VI by transformations or introduction of substituents or groups. Such examples are given below:

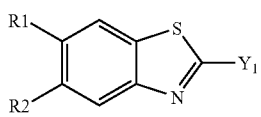

(II)

$Y_1$ = H, F, Cl, Br, I, OTf, SMe, B(OH)$_2$, B(Oalkyl)$_2$, Sn(n-Bu)$_3$, MgX, ZnX

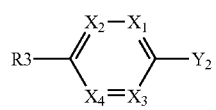

(III)

$Y_2$ = F, Cl, Br, I, OTf, SMe, B(OH)$_2$, B(Oalkyl)$_2$, Sn(n-Bu)$_3$, MgX, ZnX

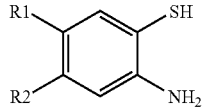

(IV)

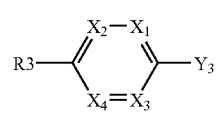

(V)

$Y_3$ = I, CHO, COOH, COCl, CN, COOalkyl, CONH2, CSNH2, beta-chlorocinnamaldehyde or equivalent carboxylic acid derivatives

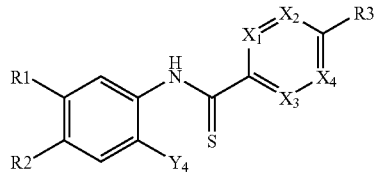

(VI)

$Y_4$ = H, Br

1) Preparation of Compounds of Formula II or III in which Y1 and Y2, Respectively is B(Oalkyl)$_2$, B(OH)$_2$, MgX or ZnX:

a) From the corresponding chlorides, bromides, iodides or triflates through palladium catalysed borylation with for example bis(pinacolato)diboran using for example PdCl$_2$ (dppf), or Pd(dba)$_2$ with added tricyclohexylphosphine, as catalysts, together with stoichiometric amounts of a base such as KOAc and NEt$_3$ in solvents such as DMSO, DMF, DMA or dioxan at a temperature from r.t. to 80° C., alternatively subsequently followed by acidic hydrolysis (Ishiyama et al. Tetrahedron 2001, 57, 9813; Murata et al. J. Org. Chem. 2000, 65, 164).

b) From the corresponding chlorides, bromides or iodides by initial conversion into an arylmagnesium ($Y_1$ or $Y_2$=MgX) or lithium reagent by treatment with for example nBuLi, nBu$_3$MgLi or Mg, followed by trapping with for example triisopropyl borate or the like and alternatively subsequent acidic hydrolysis to give the corresponding borylated compounds, or with zinc dust to give the corresponding organic Zn-compounds.

2) Preparation of Compounds of Formula II in which $Y_1$ is a Halide:

a) From the corresponding unsubstituted benzothiazole ($Y_1$=H) via metallation with a lithium reagent such as nBuLi, followed by a metal-halogen exchange using halogen sources such as CCl$_4$, CBr$_4$ or I$_2$ (Boga et al. J. Organometallic Chem 2000, 601, 233)

b) From the corresponding amine via a Sandmeyer reaction initiated by converting the amine to a diazonium salt followed by treatment with cuprous chloride or cuprous bromide (Das et al. Bioorg. & Med. Chem. Lett. 2003, 13, 2587).

3) Preparation of Compounds of Formula II or III in which $Y_1$ and $Y_2$ Respectively is a Triflate:

From the corresponding alcohol by conversion into the triflate using O(SO$_2$CF$_3$)$_2$ and an base such as triethylamine and pyridine.

4) Preparation of Compounds of Formula II or III in which $Y_1$ and $Y_2$ Respectively is a Thioether, such as Thiomethyl:

From the corresponding thiol by treatment with methyl iodide in a solvent such as DMF MeCN or DCM under basic conditions (Karlsson et al. Bioorg. & Med. Chem. 2004, 12, 2369).

5) Preparation of Compounds of Formula II or III in which $Y_1$ and $Y_2$ Respectively is Sn(nBu)$_3$ or Sn(Me)$_3$, Sn(Ph)$_3$ or ZnX:

From the corresponding unsubstitutes benzothiazole ($Y_1$=H) via metallation with a lithium reagent, such as MeLi or nBuLi, followed by transmetallation using organotin chlorides such as Me$_3$SnCl or nBu$_3$SnCl, or a zinc salt olloy et al. J. Organometallic Chem 1989, 365, 61)

6) Preparation of Intermediate IV a) From the corresponding 2-amino-benzothiazoles by base hydrolysis using a base such as aq. KOH, NaOH in a solvent such as ethylene glycol, ethanol and water under elevated temperatures. (Mathis et al. J. Med. Chem. 2003, 46, 2740; Inoue et al. Chem. Pharm. Bull. 1997, 45, 1008).

b) From the corresponding benzothiazole via hydrazinolysis using hydrazine in a solvent such as ethanol at elevated temperatures. (Tsuruoka et al Chem. Pharm. Bull. 1998, 46, 623)

7) Preparation of Intermediate VI

A suitably substituted aniline is transformed into a benzoylamide by coupling with an appropriate acid chloride. The benzoylamide is subsequently converted into the corresponding benzoylthioamide using Lawesson's reagent in a solvent such as HMPA or chlorobenzene. (Shi et al. J. Med. Chem. 1996, 39, 3375; Mathis et al. J. Med. Chem. 2003, 46, 2740; Hutchinson et al. J. Med. Chem. 2001, 44, 1446).

Methods of Preparation of Non-Labeled Compounds of Formula I

Non-limiting examples of methods for the preparation of compounds of formula I are given below:

1) Preparation by Pd or Ni Catalysed Cross-Coupling Reactions of Intermediates II and III.

a) Palladium catalysed Suzuki coupling of aryl halides, or pseudo-halides, of intermediates of formula II and III (e.g. $Y_1$,$Y_2$=chloride, bromide, iodide or triflates) with boronic acids or esters of formula III or II ($Y_1,Y_2$=B(OH)$_2$, B(Oalkyl)$_2$), respectively. A palladium catalyst, such as Pd(dppf)Cl$_2$*DCM, PdCl$_2$(PPh$_3$)$_2$, Pd(PPh$_3$)$_4$ or Pd$_2$(dba)$_3$, are used in combination with stoichiometric amount of a base, such as K$_2$CO$_3$ (aq.), K$_3$PO$_4$, NaOH (aq.) or NaHCO$_3$ (aq.), in solvents, such as DME, DMF, THF, toluene or dioxane, at a temperature from r.t. to 120° C. (Kumar et al. J. Label Compd. Radiopharm. 2003, 46, 1055; Majo et al. Tetrahedron Lett. 2003, 44, 8535; Arterburn et al. Chem. Commun. 2003, 1890).

b) Palladium catalysed and copper(I) mediated cross coupling of thioethers of intermediates of formula II and III (eg. $Y_1,Y_2$=SMe) with boronic acids or esters or stannanes of formula III or II (e.g. $Y_1,Y_2$=B(OH)$_2$, B(Oalkyl)$_2$, Sn(n-Bu)$_3$), respectively. A palladium catalyst such as Pd(dba)$_2$, together with additives, such as tris(2-furyl)phosphine and ZnOAc, may be used in a solvent, such as THF, in the case of coupling of boronic acids or esters (Liebeskind et al. Org. Lett. 2002, 4, 979). In the case of coupling of stannanes, a palladium catalyst such as Pd(PPh$_3$)$_4$ or PdCl(PPh$_3$)$_2$ (CH$_2$Ph), may be used in a solvent, such as THF (Liebeskind et al. Org. Lett. 2003, 5, 801).

c) Palladium catalysed Stille coupling of aryl halides, or pseudo-halides, of intermediates of formula II and III (e.g. $Y_1,Y_2$=chloride, bromide, iodide or triflates) with aryl stannanes of formula III or II (e.g. $Y_1,Y_2$=Sn(n-Bu)$_3$), respectively. A palladium catalyst such as Pd(PPh$_3$)Cl$_2$, Pd(PPh$_3$)$_4$, or Pd$_2$(dba)$_3$ together with additives, such as CuI, tri-phenylarsine, tri-2-furylphosphine, may be used in solvents, such as DMF, THF, toluene or xylene, at a temperature from r.t. to 120° C. (Benhida et al. Tetrahedron Lett. 1999, 40, 5701).

d) Nickel catalysed cross coupling of halides of intermediates of formula II and III (e.g. $Y_1,Y_2$=Cl, Br, I) with Grignard reagents of formula III or II (e.g. $Y_1,Y_2$=MgBr), respectively. A Nickel catalyst, such as NiCl$_2$(PEt$_3$)$_2$, NiCl$_2$(PPh$_3$)$_2$ or NiCl$_2$(Ph$_2$PCH$_2$CH$_2$CH$_2$PPh$_2$), may be used in solvents, such as THF, at elevated temp. (Babudri et al. Tetrahedron 1983, 39, 1515).

e) Palladium catalysed and copper(I) mediated cross coupling of benzothiazoles II ($Y_1$=H) with bromides of formula III ($Y_2$=Br). A palladium catalyst, such as Pd(OAc)$_2$, together with a co-catalyst, such as CuBr, and additives, such as the ligand P(t-Bu)$_3$, and the base Cs$_2$CO$_3$, may be used in a solvent, such as DMF, at an elevated temperature (Yokooji et al. Tetrahedron 2003, 59, 5685 and Alagille et al. Tetrahedron Lett. 2005, 46, 1349).

2) Preparation by Employment of Compounds IV and V as Starting Materials:

(a) Condensation of the ortho-amino thiophenol IV with intermediate V in which $Y_3$ is aldehyde, carboxylic acid, acid chloride, nitrile, phenolic ester, anhydride, amide, is thioamide or equivalent carboxylic acid derivatives in solvents, such as DMSO, EtOH, toluene, CHCl$_3$, pyridine or in ionic liquids, at a temperature from r.t. to 220° C. by conventional heating, or with microwave irradiation. An additive, such as polyphosphoric acid, scandium triflate, ceric ammonium nitrate or silica, is used to facilitate the reaction (Mathis et al. J. Med. Chem. 2003, 46, 2740; Kodomari et al. Synth. Commun. 2004, 34, 3029; Hein et al. J. Am. Chem. Soc. 1957, 79, 427; Karlsson et al. Bioorg. & Med. Chem. 2004, 12, 2369; Tale Org. Lett. 2002, 4, 1641; Chakraborti et al. Synlett 2004, 1533; Matsushita et al. Tetrahedron Lett. 2004, 45, 313; Dyes and Pigments 1990, 12, 243-8; Archiv der Pharmazie 1991, 324, 185).

(b) Reacting ortho-amino thiophenols IV with intermediates V in which $Y_3$ is a halide through palladium-catalyzed carbonylation under high pressure in the presence of 2,6-lutidine in solvents such as dimethyl acetamide. (Perry et al Organometallics 1994, 13, 3346).

(c) Microwave mediated reaction of o-amino thiophenols IV with intermediate V in which $Y_3$ is a β-chlorocinnamaldehyde in the presence of p-TsOH (Paul et al. Synth. Commun 2002, 32, 3541).

3. The Following Other Routes May Be Used for the Synthesis of Compounds of Formula I Starting from Intermediates of Formula VI:

a) By the Jacobson method through oxidative radical cyclization of thioanilides VI ($Y_3$=H) by treatment with excess of potassium ferricyanide at elevated temperature under basic conditions (Mathis et al. J. Med. Chem. 2003, 46, 2740; Hutchinson et al. J. Med. Chem. 2001, 44, 1446; Shi et al. J. Med. Chem. 1996, 39, 3375; Zeitschrift fuer Chemie 1985, 25, 23).

b) Through intramolecular cyclization of o-bromo substituted thioanilides VI ($Y_4$=Br) under basic conditions, e.g. with NaH as base in NMP as solvent (Hutchinson et al. Tetrahedron Lett 2000, 41, 425; Hutchinson et al. J. Med. Chem. 2001, 44, 1446), or via palladium catalysis (Benedi et al. Tetrahedron Lett 2003, 44, 6073).

Methods of Preparation of Precursors of Formula VII

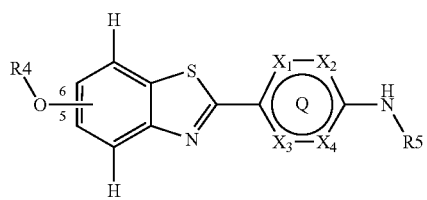

VII

Non-limiting examples of methods for preparation of precursors of formula VII are given below. Compounds of formula VII are useful precursors for preparation of [$^{11}$C]methyl labeled compounds of formula I.

Preparation of Intermediates Useful for the Preparation of Precursors VII

Compounds of formula VIII, IX, X, XI, XII and XIII are useful intermediates in the preparation of precursors of formula VII. R4, R5 and $X_1$ to $X_4$ are defined as in formula VII. Compounds of formula VIII-XIII are either commercially available, or can be prepared from commercially available samples, or non-limiting methods for their preparation are described herein, or in the literature. For example, compounds in which one or more of $Y_3, Y_4, Y_5, Y_6$, R4 or R5 does not correspond to the definitions of formula VIII-XIII, can be used for the preparation of compounds of formula VIII-XIII by transformations or introduction of substituents or groups. Such examples are given below:

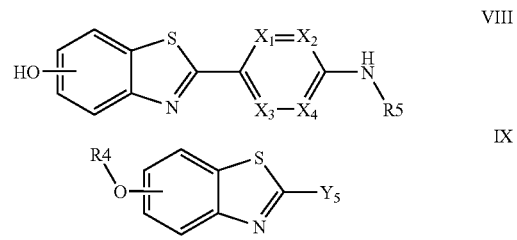

$Y_5$ = Cl, Br, I, OTf, B(OH)$_2$, B(Oalkyl)$_2$, Sn(n-Bu)$_3$, MgX

X

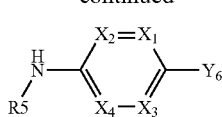

$Y_6$ = Cl, Br, I, OTf, B(OH)2, B(Oalkyl)2, Sn(n-Bu)3, MgX

XI

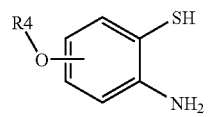

XII

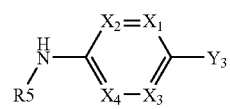

$Y_3$ = I, CHO, COOH, COCl, CN, COOalkyl, CONH2, CSNH2, beta-chlorocinnamaldehyde or equivalent carboxylic acid derivatives

XIII

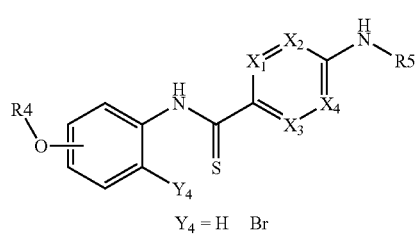

$Y_4$ = H   Br

1) Preparation of compounds of formula VIII:

a) Palladium-catalyzed Suzuki coupling of aryl halides, or pseudo-halides, of intermediates of formula II (R1 or R2=OH) and X (e.g. $Y_5$, $Y_6$=chloride, bromide, iodide or triflates) with boronic acids or esters of formula X or II (R1 or R2=OH, $Y_5$, $Y_6$=B(OH)$_2$ or B(Oalkyl)$_2$), respectively, according to the procedure described for the preparation of compounds I. When R1 or R2 of formula II is a protected hydroxy-group, and the protective group employed is not stable under standard aqueous basic Suzuki conditions, as in the case of for example t-butyldimethylsilyl protected hydroxy-groups, it will normally be cleaved of during the reaction to generate a product in which the former protected hydroxy-group is found as the free hydroxy.

b) Palladium-catalyzed Stille coupling of aryl halides, or pseudo-halides, of intermediates of formula II (R1 or R2=OH) and X (e.g. $Y_5$, $Y_6$=chloride, bromide, iodide or triflates) with aryl stannanes of formula X or II (R1 or R2=OH, $Y_5$, $Y_6$=e.g. Sn(n-Bu)$_3$), respectively, according to the procedure described in the preparation of compounds I.

c) By employment of compounds $X_1$ and XII as starting materials in analogy to the methods described for the preparation of compounds I starting from IV and V.

d) Starting from intermediates XIII in analogy to the synthesis of I from VI.

2) Preparation of IX and X, in which $Y_5$ and $Y_6$ is an halide, a triflate, B(Oalkyl)$_2$, B(OH)$_2$, Sn(n-Bu)$_3$ or MgX, may be done by the same procedures as described for the preparation of the corresponding compounds II, in which R1 or R2 is O—R4, where R4 is a suitable protective group compatible with the respective reaction conditions employed as well known to the one skilled in the art.

3) Compounds XI and XIII may be prepared according to the synthesis of intermediates IV and VI.

Methods of Preparation of Precursors of Formula VII

In the synthesis of precursors VII, the protective group R4 may be introduced either on a benzothiazole derivative before coupling of the hence produced intermediates IX with intermediates X, or after the fusion of benzothiazole derivatives with heterocycles X, i.e. on structures VIII. All protective groups that represent R4 may be introduced by conventional procedures. Non-limiting examples of methods for the preparation of precursors of formula VII are given below:

1) Reacting intermediates VIII with a silylating agent, such as t-butyldimethylsilylchloride, in the presence of a base, such as imidazole or triethylamine, in a solvent, such as DMF or DCM, at a temperature from 0° C. to rt.

2) Intermediates VIII may be treated with 2-(trimethylsilyl)ethoxymethylchloride and a base, for example (i-Pr)$_2$NEt, NaH or Et$_3$N in the presence of DMAP, in a solvent, such as DCM, DMF or benzene, at rt or elevated temperature.

3) By treatment of VIII with p-methoxybenzylbromide and a base such as (i-Pr)$_2$NEt in DCM at ambient temperature.

4) Transition metal-catalyzed cross couplings of intermediates IX and X:

Precursors VII may be prepared from intermediates IX and X by the metal-catalyzed cross coupling reactions described for the preparation of compounds I by coupling II (R1 or R2=OH) and III provided that the R4-moiety is stable under the conditions employed.

5) Preparation of precursors of formula VII may be done through intermolecular reactions between intermediates XI and XII, or alternatively, through intramolecular reactions of XIII, in accordance to methods 1c and 1d, respectively, as described for the syntheses of VIII.

Methods of Preparation of Labeled Compounds of Formula I

In general, the same synthetic reactions used for the assembly of non-labeled compounds of formula I from non-labeled reagents or intermediates, can be employed for the analogous incorporation of a detectable isotope by use of the corresponding labeled reagents or intermediates.

It is preferred to introduce the label at a late stage of the synthesis toward compounds of formula I, especially if the label is an isotope with relatively short half-life, such as $^{11}$C. Most preferred is to do this introduction as the last synthetic step.

Several useful reagents, synthons or intermediates labeled with long-lived or non-radioactive isotopes, including for example [$^{2/3}$H]H$_2$, [$^{2/3}$H]CH$_3$I, [$^{13/14}$C]CH$_3$I, [$^{13/14}$C]CN$^-$, [$^{13/14}$C]CO$_2$ are commercially available and can, if needed, be further synthetically transformed by conventional synthetic methods. Reagents labeled with more short-lived isotopes, such as $^{11}$C and $^{18}$F, are generated by a cyclotron, followed by suitable trapping and optionally further synthetic manipulations to provide the desired reagent. The generation and the synthetic manipulations of labeled reagents and intermediates, and the use and chemistries of these precursors for the synthesis of more complex labeled is molecules, is well known to the one skilled in the art of radio-synthesis and labeling and reviewed in the literature (Långström et al. Acta Chem. Scand. 1999, 53, 651). For additional references see for example: Ali et al. Synthesis 1996, 423 for labeling with halogens; Antoni G., Kihlberg T., and Långström B. (2003) Handbook of nuclear chemistry, edited by Vertes A., Nagy S., and Klenscar Z., Vol. 4, 119-165 for labeling for PET-applications; Saljoughian et al. Synthesis 2002, 1781 for labeling with $^3$H; McCarthy et al. Curr. Pharm. Des. 2000, 6, 1057 for labeling with $^{14}$C.

Detectable isotopes, useful for the labeling of compounds of formula I as defined herein include, for use in PET: $^{11}$C, $^{18}$F, $^{75}$Br, $^{76}$Br and $^{120}$I, for use in SPECT: 123I and $^{131}$I, for MRI-applications: $^{19}$F and $^{13}$C, for detection in in-vitro and post-mortem samples: $^3$H, $^{14}$C and $^{125}$I. The most useful isotopes for labeling are $^{11}$C, $^{18}$F, $^{123}$I, $^{19}$F, $^3$H and $^{14}$C.

Below follow non-limiting descriptions on processes for the preparation of labeled compounds of formula I:

Compounds of formula I, in which either R1, R2, or R3 is hydroxy, amino or aminoalkyl are useful precursors for O- and N-alkylation, respectively, with a labeled alkylating agent, such as [$^{11}$C]methyl iodide or triflate, as described in for example Solbach et al. Applied Radiation and Isotopes 2005, 62, 591 and Mathis et al. J. Med. Chem. 2003, 46, 2740, [$^{3}$H]-methyl iodide, or [$^{14}$C]-methyl iodide.

For example, the compounds of formula I in which R1 or R2 is hydroxy (the other is hydrogen), X1 or X2 is nitrogen (the other is carbon), X3 and X4 is carbon, and R3 is amino or aminoalkyl, constitute suitable precursors for labeling. Treatment of an excess of either of these precursors with $^{11}$C-methyl triflate, in a solvent such as acetone without added base, results in selective N-alkylation and thus in the formation of the corresponding $^{11}$C labelled compounds of formula I in which R3 is transformed into NH[$^{11}$C]CH$_3$ (from amino) and NCH$_3$[$^{11}$C]CH$_3$ (from aminomethyl), respectively. When the same before mentioned precursors, however, is treated with [$^{11}$C]methyl iodide under basic condition, such as in the presence of potassium carbonate, in a solvent such as DMSO, selective O-alkylation occurs because of relatively higher reactivity of the oxygen-atom after deprotonation, and thus in the formation of compounds of formula I in which the OH-group (R1 or R2) is transformed into the O[$^{11}$C]CH$_3$-group.

The most suitable and preferred precursors for labeling by selective introduction of a $^{11}$C-methyl group by N-alkylation, are compounds in which the reactivity to alkylation, of a present competing nucleophilic functional group, such as hydroxy, is lowered or blocked by a suitable protective group. The function of the protective group is in this context to protect the nucleophilic functional group against alkylation and should preferably be stable under non-aqueous basic conditions, under which the desired N-alkylation is facilitated, but readily removed by other means after fulfillment of its duty. Such protective groups, and methods for their introduction and removal, are well known to the one skilled in the art. Examples of protective groups useful for protection of aromatic hydroxy-groups against competing alkylation include, but is not limited to, methyl, 2-(trimethylsilyl)ethoxymethyl, alkoxymethyl and t-butyldimethylsilyl. Removal of such a protective group after the alkylation is well known to the one skilled in the art and include, in the case of silyl-based protective groups such as t-butyldimethylsilyl, for example treatment with a fluoride ion source, such as TBAF, or treatment with water under basic conditions in a suitable solvent, such as DMSO in the presence of KOH at rt.

Compounds of formula I, in which either R1, R2, or R3 is amino, are useful precursor for labeling by initial diazotation, when appropriate followed by conversion into the corresponding triazine derivative, before subsequent treatment with labeled nucleophilic reagents according to standard reactions. Detectable isotopes that may be introduced this way include, but is not limited to $^{18}$F, $^{75}$Br, $^{123}$I, $^{125}$I and $^{131}$I as described in for example Zhu et al. J. Org. Chem. 2002, 67, 943; Maeda et al. J. Label Compd Radiopharm 1985, 22, 487; Berridge et al. J. Label Compd Radiopharm 1985, 22, 687; Suchiro et al. J. Label Compd Radiopharm 1987, 24, 1143; Strouphauer et al. Int. J. Appl. Radiat. Isot. 1984, 35, 787; Kortylevicz et al. J. Label Compd Radiopharm 1994, 34, 1129; Khalaj et al. J. Label Compd Radiopharm 2001, 44, 235 and Rzeczotarski et al. J. Med. Chem. 1984, 27, 156. In compounds of formula I, where R1, R2, or R3 is a trialkyltin-group, halogenation with labeled reagents results in displacement of the trialkyltin-group as described in for example Staelens et al. J. Label Compd Radiopharm 2005, 48, 101; Hocke et al. Bioorg. Med. Chem. Lett. 2004, 14, 3963; Zhuang et al. J. Med. Chem. 2003, 46, 237; Füchtner et al. Appl. Rad. Isot. 2003, 58, 575 and Kao et al. J. Label Compd Radiopharm 2001, 44, 889. The same precursors are also useful for palladium-catalyzed conversion into the corresponding $^{11}$C-labeled ketones and methyl-derivatives as described in for example Lidström et al. J. Chem. Soc. Perkin Trans. 1 1997, 2701 and Tarkiainen et al. J. Label Compd Radiopharm 2001, 44, 1013. The trialkyltin substituted compounds, in turn, are preferably prepared from the corresponding halides or pseudo-halides, such as the triflates, by well known methods employing palladium as catalyst in reaction with the corresponding distannane. When this methodology is used, the trialkyltin-group is preferably trimethyltin or tributyltin.

When R1, R2, or R3, in a compound of formula I, is a leaving group suitable for nucleophilic aromatic substitution, a labeled nucleophile, such as a halogenide or cyanide, can be introduced by such a displacement, resulting in a labeled compound of formula I as described in for example Zhang et al. Appl. Rad. Isot. 2002, 57, 145. The aromatic ring on which the displacement takes place is preferably relatively electron-poor for a facile reaction, and might therefore need to be substituted with an electron-withdrawing activating group such as cyano, carbaldehyde or nitro. Useful reactions, closely related to nucleophilic aromatic substitutions and well known to the one skilled in the art, include the employment of stoichiometric amounts of copper-salts for the introduction of a labeled iodo-atom, and the use of palladium-catalysis for the introduction of a $^{11}$C-labelled cyano-group, as described in for example Musacio et al. J. Label Compd Radiopharm 1997, 34, 39 and Andersson et al. J. Label Compd Radiopharm 1998, 41, 567 respectively.

If the aromatic ring onto which the leaving group is positioned is more electron-deficient as compared to benzene, such as Q of formula I as defined herein, it is generally not needed to employ activating groups for electrophilic aromatic substitution to take place. Compounds of formula I, where R3 is either of the leaving-groups fluoro, chloro, bromo, iodo, or a sulphonate ester, and either or both of X2 and X4 is nitrogen, are suitable precursors for labeling via nucleophilic aromatic substitution of R3. It is furthermore generally preferable to use a leaving group that is chemically diverse from the group introduced by the reaction with the labeled nucleophile, in order to facilitate chromatographic separation of the labeled reaction product from the unconsumed precursor.

Additional useful methods, well known to the one skilled in the art, for preparation of labeled compounds of formula I by functional group transformations of suitable precursors include N-acylation of amines with [$^{11}$C], [$^{14}$C], or [$^{3}$H]acyl chlorides, palladium-catalyzed [$^{11}$C] or [$^{14}$C] cyanation of aromatic chlorides, bromides or iodides, transition-metal catalyzed substitution of suitable halides for $^{3}$H in the presence of [$^{3}$H]H$_2$, and palladium-catalyzed carbonylations with [$^{11/14}$C]CO (Perry et al. Organometallics 1994, 13, 3346).

COMPOUND EXAMPLES

Below follows a number of non-limiting examples of compounds of the invention. All of the below examplified compounds under the paragraph "compound examples", or their corresponding non-labeled analogs, display an IC$_{50}$ of less than 20 μM in the competition binding assay described herein.

General Methods

All solvents used were analytical grade and commercially available anhydrous solvents were routinely used for reactions. Reactions were typically run under an inert atmosphere of nitrogen or argon.

$^1$H spectra were recorded on a Bruker av400 NMR spectrometer, operating at 400 MHz for proton, equipped with a 3 mm flow injection SEI $^1$H/D-$^{13}$C probehead with Z-gradients, using a BEST 215 liquid handler for sample injection, or on a Bruker DPX400 NMR spectrometer, operating at 400 MHz for proton, equipped with a 5 mm 4-nucleus probehead equipped with Z-gradients.

Unless specifically noted in the examples, $^1$H spectra were recorded at 400 MHz in DMSO-$d_6$ as solvent. The residual solvent signal was used as reference. The following reference signals were used: the middle line of DMSO-$d_6$ δ 2.50; the middle line of $CD_3OD$ δ 3.31; $CDCl_3$ δ 7.26. In those instances where spectra were run in a mixture of $CDCl_3$ and $CD_3OD$, the reference was set to 3.31 ppm. All chemical shifts are in ppm on the delta-scale (δ) and the fine splitting of the signals as appearing in the recordings (s: singlet, br. s: broad singlet, d: doublet, t: triplet, q: quartet, m: multiplet).

$^3$H spectra were recorded on a Bruker DRX 600 NMR Spectrometer, operating at 640 MHz for tritium and at 600 MHz for proton, equipped with a 5 mm $^3$H/$^1$H SEX probehead with Z-gradients. $^1$H decoupled $^3$H spectra were recorded on samples dissolved in $CD_3OD$. For $^3$H NMR spectra referencing, a ghost reference frequency was used, as calculated by multiplying the frequency of internal TMS in a $^1$H spectrum with the Larmor frequency ratio between $^3$H and $^1$H (1.06663975), according to the description in Al-Rawi et al J. Chem. Soc. Perkin Trans. II 1974, 1635.

Mass spectra were recorded on a Waters LCMS consisting of an Alliance 2795 (LC), Waters PDA 2996, and ELS detector (Sedex 75) and a ZMD single quadrupole mass spectrometer. The mass spectrometer was equipped with an electrospray ion source (ES) operated in a positive or negative ion mode. The capillary voltage was 3 kV and cone voltage was 30 V. The mass spectrometer was scanned between m/z 100-600 with a scan time of 0.7 s. The column temperature was set to 40° C. A linear gradient was applied starting at 100% A (A: 10 mM $NH_4OAc$ in 5% MeCN) and ending at 100% B (B: MeCN). The column used was a X-Terra MS C8, 3.0×50; 3.5 μm (Waters) run at 1.0 mL/min.

Preparative chromatography (prep. HPLC) was run on a Waters autopurification HPLC with a diode array detector. Column: XTerra MS C8, 19×300 mm, 10 μm. Narrow gradients with MeCN/(95:5 0.1M $NH_4OAc$:MeCN) were used at a flow rate of 20 ml/min.

Microwave heating was performed in a Creator, Initiator or Smith Synthesizer Single-mode microwave cavity producing continuous irradiation at 2450 MHz.

Example 1

Ethyl 2-(6-piperazin-1-ylpyridin-3-yl)-1,3-benzothiazole-6-carboxylate Trifluoroacetate

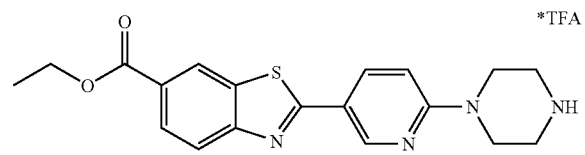

(a) 2-[6-[4-[(1,1-Dimethylethoxy)carbonyl]-1-piperazinyl]-3-pyridinyl]-6-benzothiazolecarboxylic Acid Ethyl Ester

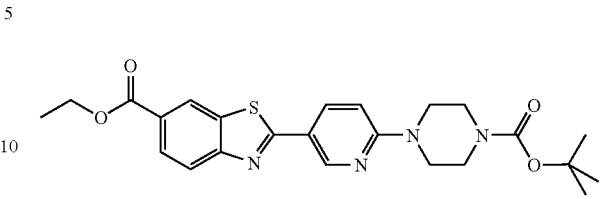

A mixture of 2-bromo-1,3-benzothiazole-6-carboxylic acid ethyl ester (See WO 95/25108) (0.74 g, 2.57 mmol), 4-[5-(4,4,5,5-tetramethyl-[1,3,2]dioxaborolan-2-yl-piperazine-1-carboxylic acid tert-butyl ester (1.0 g, 2.57 mmol), sodium carbonate (0.820 g, 7.71 mmol) and Pd(dppf)Cl₂*DCM (0.094 g, 0.13 mmol) in THF/water (9:1, 15 mL) was stirred at reflux o.n. Additional Pd(dppf)Cl₂*DCM (20 mg) was added and the reaction was refluxed for one more day. The r.m. was concentrated in vacuo and to the residue was added DCM and water. The aqueous layer was extracted three times with DCM, dried (MgSO₄), filtered and evaporated in vacuo. The product was purified by flash column chromatography (35% ethyl acetate in hexane), giving the title compound (0.85 g) as a solid. $^1$H NMR δ 8.83 (d, 1H) 8.73 (s, 1H) 8.19 (dd, 1H) 8.04 (s, 2H) 7.00 (d, 1H) 4.36 (q, 2H) 3.65-3.72 (m, 4H) 3.42-3.50 (m, 4H) 1.43 (s, 9H) 1.36 (t, 3H); MS m/z (M+H) 469.

(b) Ethyl 2-(6-piperazin-1-ylpyridin-3-yl)-1,3-benzothiazole-6-carboxylate Trifluoroacetate (title compound)

2-[6-[4-[(1,1-Dimethylethoxy)carbonyl]-1-piperazinyl]-3-pyridinyl]-6-benzothiazolecarboxylic acid ethyl ester (0.42 g, 0.90 mmol) was dissolved in DCM (35 mL) and TFA (2 mL) was added. The reaction was stirred at r.t. for 3 days. Sat. sodium hydrogencarbonate was added to the mixture. The precipitate was collected, followed by washing with DCM and water, before drying in vacuo over $P_2O_5$ to give the title compound (0.34 g) as a yellow solid. $^1$H NMR δ 8.82-8.93 (m, 3H) 8.76 (s, 1H) 8.27 (dd, 1H) 8.07 (d, 2H) 7.11 (d, 1H) 4.37 (q, 2H) 3.84-3.95 (m, 4H) 3.23 (br. s., 4H) 1.36 (t, 3H); MS m/z (M+H) 369.

Example 2

Ethyl 2-[6-(4-Methylpiperazin-1-yl)pyridin-3-yl]-1,3-benzothiazole-6-carboxylate Formaldehyde (37% aq., 0.212 mL, 2.61 mmol) was added to a suspension of ethyl 2-(6-piperazin-1-ylpyridin-3-yl)-1,3-benzothiazole-6-carboxylate trifluoroacetate (0.315 g, 0.65 mmol) in methanol (10 mL). Sodium cyanoborohydride (74 mg, 1.17 mmol) was added and the resulting mixture was stirred at r.t. for 1 h. The r.m. was then kept at −10° C. o.n. The formed solid was collected, washed with cold methanol and dried to give the title compound. The mother liquor was evaporated in vacuo and the residue was partitioned between DCM and sat. sodium hydrogencarbonate. The aqueous layer was extracted twice with DCM, dried ($Na_2SO_4$), filtered, and evaporated in vacuo, giving together with the filtrated solid the title compound (0.20 g) as a yellow solid. $^1$H NMR δ ppm 8.83 (d, 1H) 8.73 (s, 1H) 8.17 (dd, 1H) 8.05 (s, 2H) 7.01 (d, 1H) 4.36 (q, 2H) 3.70 (br. s., 4H) 3.32 (s, 4H) 2.29 (s, 3H) 1.36 (t, 3H); MS m/z (M+H) 383.

Example 3

2-[6-(4-Methylpiperazin-1-yl)pyridin-3-yl]-1,3-benzothiazole-6-carboxamide Acetate

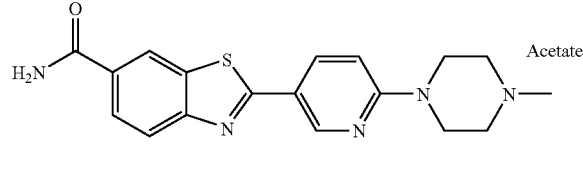

(a) 2-[6-(4-Methylpiperazin-1-yl)pyridin-3-yl]-1,3-benzothiazole-6-carboxylic Acid Hydrochloride

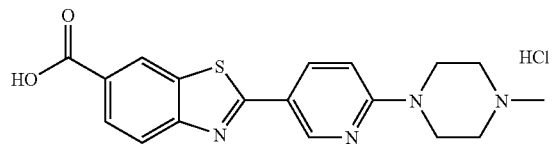

Ethyl 2-[6-(4-methylpiperazin-1-yl)pyridin-3-yl]-1,3-benzothiazole-6-carboxylate (46 mg, 0.12 mmol) was heated at 110° C. in 6 M HCl (2 mL) for 3 h. The solvent was evaporated in vacuo, before co-evaporation with toluene three times, to give the title compound (46 mg) as a yellow solid. $^1$H NMR δ 10.90 (br. s., 1H) 8.88 (d, 1H) 8.73 (s, 1H) 8.28 (dd, 1H) 8.05 (s, 2H) 6.97-7.40 (m, 2H) 4.59 (d, 2H) 3.51 (d, 2H) 3.33-3.45 (m, 2H) 3.02-3.16 (m, 2H) 2.80 (d, 3H); MS m/z (M+H) 355, (M−H) 353.

(b) 2-[6-(4-Methylpiperazin-1-yl)pyridin-3-yl]-1,3-benzothiazole-6-carboxamide Acetate (title compound)

2-[6-(4-Methylpiperazin-1-yl)pyridin-3-yl]-1,3-benzothiazole-6-carboxylic acid hydrochloride acid (46 mg, 0.12 mmol) was added to thionyl chloride (3 mL), followed by 3 drops DMF, before heating at 70° C. o.n. The solvent was thereafter evaporated in vacuo and once with toluene to give crude 2-[6-(4-methylpiperazin-1-yl)pyridin-3-yl]-1,3-benzothiazole-6-carbonyl chloride. Ammonium hydroxide (conc., 3 mL) was added dropwise to this crude product and the mixture was thereafter stirred for 1 h at r.t. The r.m. was extracted twice with DCM, dried ($Na_2SO_4$), and evaporated in vacuo. The obtained residue was purified by prep. HPLC to give the title compound (7 mg) as a light yellow solid. $^1$H NMR δ 8.81 (d, 1H) 8.58 (s, 1H) 8.16 (dd, 1H) 8.07 (br. s., 1H) 7.99 (s, 2H) 7.45 (br. s., 1H) 7.00 (d, 1H) 3.61-3.71 (m, 4H) 2.37-2.46 (m, 4H) 2.23 (s, 3H) 1.89 (s, 3H); MS m/z (M+H) 354.

Example 4

6-Methoxy-2-(6-piperazin-1-ylpyridin-3-yl)-1,3-benzothiazole

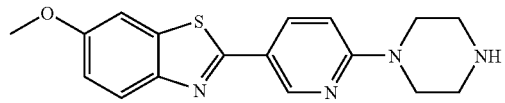

(a) Tert-butyl 4-[5-(6-Methoxy-1,3-benzothiazol-2-yl)pyridin-2-yl]piperazine-1-carboxylate

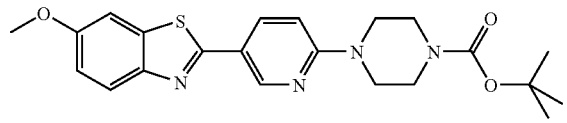

Tert-butyl 4-[5-(6-Methoxy-1,3-benzothiazol-2-yl)pyridin-2-yl]piperazine-1-carboxylate was prepared according to the method used for the preparation of 2-[6-[4-[(1,1-dimethylethoxy)carbonyl]-1-piperazinyl]-3-pyridinyl]-6-benzothiazolecarboxylic acid ethyl ester, from 2-bromo-6-methoxybenzothiazole (Yang et al. J. Biological Chem. 1989, 2, 891-898) (0.20 g), and obtained as a solid (0.23 g). $^1$H NMR δ 8.74 (s, 1H) 8.12 (d, 1H) 7.87 (d, 1H) 7.67 (s, 1H) 7.09 (dd, 1H) 6.98 (d, 1H) 3.84 (s, 3H) 3.64 (br. s., 4H) 3.45 (br. s., 4H) 1.43 (s, 9H); MS m/z M+H 427.

(b) 6-Methoxy-2-(6-piperazin-1-ylpyridin-3-yl)-1,3-benzothiazole (title compound)

6-Methoxy-2-(6-piperazin-1-ylpyridin-3-yl)-1,3-benzothiazole was prepared according to the method used for the preparation of ethyl 2-(6-piperazin-1-ylpyridin-3-yl)-1,3-benzothiazole-6-carboxylate trifluoroacetate, from tert-butyl 4-[5-(6-methoxy-1,3-benzothiazol-2-yl)pyridin-2-yl]piperazine-1-carboxylate (0.22 g), with the exception that sodium hydroxide was used instead of sat. sodium hydrogencarbonate after completion of the reaction, and that the product was taken up in DCM thereafter. The title compound was obtained as a solid (0.15 g) after drying and concentration. $^1$H NMR δ 8.71 (d, 1H) 8.07 (dd, 1H) 7.85 (d, 1H) 7.66 (d, 1H) 7.09 (dd, 1H) 6.93 (d, 1H) 3.84 (s, 3H) 3.47-3.64 (m, 4H) 2.65-2.89 (m, 4H); MS m/z (M+H) 327.

Example 5

6-Methoxy-2-[6-(4-methylpiperazin-1-yl)pyridin-3-yl]-1,3-benzothiazole

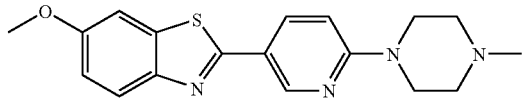

The title compound was obtained as a solid (70 mg) after preparation in accordance with the method used for the preparation of ethyl 2-[6-(4-methylpiperazin-1-yl)pyridin-3-yl]-1,3-benzothiazole-6-carboxylate, from 6-methoxy-2-(6-piperazin-1-ylpyridin-3-yl)-1,3-benzothiazole (0.13 g), with the following exceptions: Three drops of acetic acid was added to the reaction mixture and the reaction was stirred at r.t. o.n. The product was filtered and washed with methanol. $^1$H NMR δ 8.72 (d, 1H) 8.08 (dd, 1H) 7.86 (d, 1H) 7.67 (d, 1H) 7.09 (dd, 1H) 6.97 (d, 1H) 3.84 (s, 3H) 3.53-3.69 (m, 4H) 2.36-2.45 (m, 4H) 2.22 (s, 3H); MS m/z (M+H) 341.

Example 6

2-[6-(4-Methylpiperazin-1-yl)pyridin-3-yl]-1,3-benzothiazol-6-ol Acetate

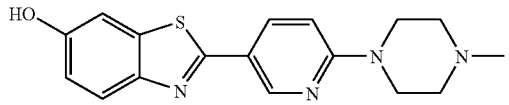

6-Methoxy-2-[6-(4-methylpiperazin-1-yl)pyridin-3-yl]-1,3-benzothiazole (0.050 g, 0.15 mmol) was dissolved in DCM (20 mL). The mixture was made acidic by addition of HCl in diethyl ether. The solvent was removed by concentration in vacuo and the residue was suspended in DCM (5 mL). Boron tribromide (0.05 mL, 0.54 mmol) in DCM (1 mL) was thereafter added dropwise at 0° C., followed by stirring at r.t. o.n. Additional DCM (5 mL) and boron tribromide (0.05 mL) was added and the reaction was continued stirring at r.t. for 3 days. The r.m. was then partitioned between DCM and sat. sodium hydrogencarbonate. The aqueous layer was extracted twice with DCM, and the combined organics dried (Na$_2$SO$_4$), filtered and evaporated in vacuo. The crude product was purified by prep. HPLC to give the title compound (11 mg) as a white solid. $^1$H NMR δ 9.94 (br. s., 1H) 8.69 (d, 1H) 8.06 (dd, 1H) 7.76 (d, 1H) 7.37 (d, 1H) 6.84-7.06 (m, 2H) 3.50-3.73 (m, 4H) 2.35-2.45 (m, 4H) 2.22 (s, 3H) 1.90 (s, 3H); MS m/z (M+H) 327, (M−H) 325.

Example 7

Ethyl 2-(6-Methoxypyridin-3-yl)-1,3-benzothiazole-6-carboxylate

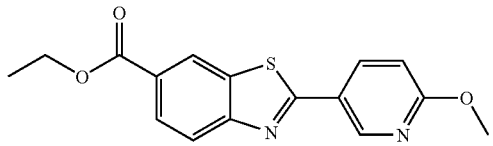

The title compound was prepared according to the method used for the preparation of 2-[6-[4-[(1,1-dimethylethoxy)carbonyl]-1-piperazinyl]-3-pyridinyl]-6-benzothiazolecarboxylic acid ethyl ester, from 2-methoxy-5-pyridineboronic acid (0.48 g, 3.14 mmol), and obtained as a solid (0.29 g) after purification by flash column chromatography using 15% ethyl acetate in hexane. $^1$H NMR δ 8.94 (d, 1H) 8.81 (s, 1H) 8.40 (dd, 1H) 8.00-8.19 (m, 2H) 7.04 (d, 1H) 4.37 (q, 2H) 3.97 (s, 3H) 1.36 (t, 3H); MS m/z (M+H) 315.

Example 8

2-(6-Methoxypyridin-3-yl)-1,3-benzothiazole-6-carboxylic Acid

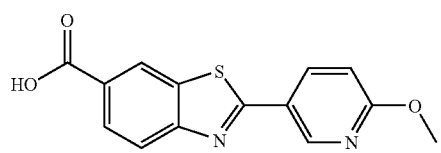

Ethyl 2-(6-methoxypyridin-3-yl)-1,3-benzothiazole-6-carboxylate (0.28 g, 0.89 mmol) was suspended in a mixture of ethanol (6 mL) and THF (2 mL). 2M NaOH (1.3 mL) was thereafter added and the reaction was stirred at r.t. for 6 h, before heating for 5 minutes with a heating gun to give a clear solution. The solution was evaporated in vacuo, water was added and the mixture was filtrated. The filtrate was made acidic with 3M HCl. The precipitated solid was collected, washed with water, dried (in vacuo over P$_2$O$_5$) to give the title compound (0.23 g) as a white solid. $^1$H NMR δ 13.13 (s, 1H) 8.93 (d, 1H) 8.77 (s, 1H) 8.40 (dd, 1H) 7.95-8.21 (m, 2H) 7.04 (d, 1H) 3.97 (s, 3H); MS m/z (M+H) 287, (M−H) 285.

Example 9

2-(6-Methoxypyridin-3-yl)-1,3-benzothiazole-6-carboxamide

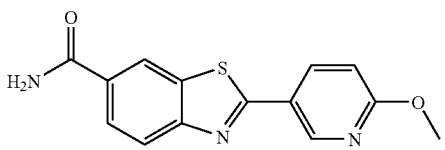

2-(6-Methoxypyridin-3-yl)-1,3-benzothiazole-6-carboxylic acid (30 mg, 0.10 mmol) was mixed with thionyl chloride (0.8 mL) and stirred at r.t. for 3 h, then heated to 50° C. for 1 h. The solvent was evaporated in vacuo to give the intermediate 2-(6-methoxypyridin-3-yl)-1,3-benzothiazole-6-carbonyl chloride as a crude product. This acid chloride was dissolved in DCM (3 mL) and added to ammonium hydroxide (conc., 2 mL). The reaction was stirred at r.t. without stopper overnight. The formed solid was collected by filtration, washed with water and dried (in vacuo over P$_2$O$_5$) to give the title compound (23 mg) as a yellow solid. $^1$H NMR δ 8.93 (d, 1H) 8.64 (s, 1H) 8.39 (dd, 1H) 7.95-8.19 (m, 3H) 7.50 (s, 1H) 7.04 (d, 1H) 3.97 (s, 3H); MS m/z (M+H) 286, (M−H) 284.

Example 10

2-(6-Methoxypyridin-3-yl)-N-methyl-1,3-benzothiazole-6-carboxamide

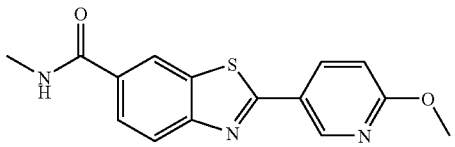

2-(6-Methoxypyridin-3-yl)-1,3-benzothiazole-6-carboxylic acid (40 mg, 0.14 mmol) was mixed with thionyl chloride (1 mL) and stirred at r.t. for 3 h, then heated to 50° C. for 1 h. The solvent was evaporated in vacuo to give the intermediate 2-(6-methoxypyridin-3-yl)-1,3-benzothiazole-6-carbonyl chloride as a crude product. This acid chloride was dissolved in DCM (3 mL) and added to methylamine (40% in methanol, 2 mL). The reaction was stirred at r.t. without stopper overnight. The formed solid was collected by filtration, washed with water and dried (in vacuo over $P_2O_5$) to give the title compound (35 mg) as a light yellow solid. $^1$H NMR δ 8.92 (d, 1H) 8.51-8.68 (m, 2H) 8.39 (dd, 1H) 8.09 (d, 1H) 7.98 (d, 1H) 7.04 (d, 1H) 3.97 (s, 3H) 2.83 (d, 3H); MS m/z (M+H) 300, (M−H) 298.

Example 11

2-(6-Methoxypyridin-3-yl)-6-(pyrrolidin-1-ylcarbonyl)-1,3-benzothiazole

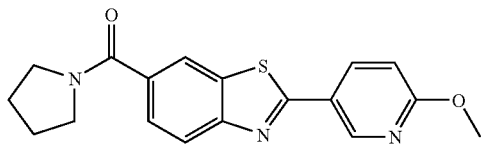

2-(6-Methoxypyridin-3-yl)-1,3-benzothiazole-6-carboxylic acid (40 mg, 0.14 mmol) was mixed with thionyl chloride (1 mL) and stirred at r.t. for 3 h, then heated to 50° C. for 1 h. The solvent was evaporated in vacuo to give the intermediate, 2-(6-methoxypyridin-3-yl)-1,3-benzothiazole-6-carbonyl chloride as a crude product. This acid chloride was dissolved in DCM (3 mL) and added to pyrrolidine (0.5 mL) in $CH_2Cl_2$ (1.5 mL). The reaction was stirred at r.t. for 1 h. Water was added and the reaction mixture was extracted, twice, with DCM, dried ($MgSO_4$), filtered and the solvent was evaporated. The solid was dried (in vacuo over $P_2O_5$) to give the title compound (45 mg) as an off-white solid. $^1$H NMR δ 8.92 (d, 1H) 8.39 (dd, 1H) 8.35 (s, 1H) 8.07 (d, 1H) 7.67 (d, 1H) 7.04 (d, 1H) 3.97 (s, 3H) 3.51 (t, 2H) 3.45 (t, 2H) 1.78-1.95 (m, 4H); MS m/z (M+H) 340.

Example 12

2-(6-piperazin-1-ylpyridin-3-yl)-1,3-benzothiazol-6-amine

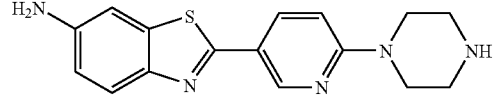

(a) tert-Butyl 4-[5-(6-nitro-1,3-benzothiazol-2-yl)pyridin-2-yl]piperazine-1-carboxylate

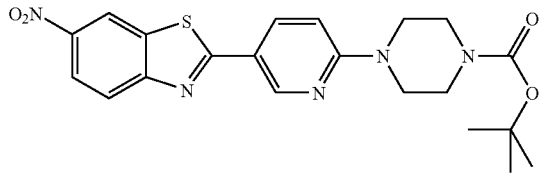

The compound tert-butyl 4-[5-(6-nitro-1,3-benzothiazol-2-yl)pyridin-2-yl]piperazine-1-carboxylate was prepared in accordance with the method used for preparation of 2-[6-[4-[(1,1-dimethylethoxy)carbonyl]-1-piperazinyl]-3-pyridinyl]-6-benzothiazolecarboxylic acid ethyl ester, from 2-bromo-6-nitrobenzothiazole (0.55 g, 2.14 mmol), with the following modifications: In the workup the solid was filtered off and washed with THF/water (9:1), followed by water. The solid product was dried (in vacuo over $P_2O_5$). The filtrate was extracted three times with DCM. The combined organic phases was washed with brine, dried ($Na_2SO_4$), filtrated and evaporated in vacuo. The combined crude solid was purified by flash column chromatography (heptane:ethyl acetate; 80:20 to 60:40) to give the title compound (0.47 g) as a solid. MS m/z (M+H) 442.

(b) 4-[5-(6-Amino-benzothiazol-2-yl)-pyridin-2-yl]-piperazine-1-carboxylic acid tert-butyl ester

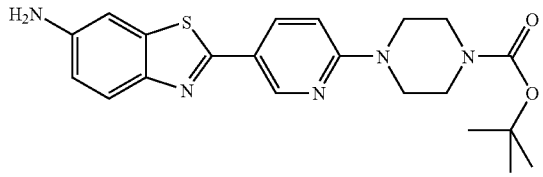

tert-Butyl 4-[5-(6-nitro-1,3-benzothiazol-2-yl)pyridin-2-yl]piperazine-1-carboxylate (90 mg, 0.2 mmol) was dissolved in methanol (8 mL). After addition of 7M $NH_3$ in methanol (2 mL), palladium on carbon (10%, 10 mg) was added and the flask was evacuated and filled with hydrogen gas. The reaction mixture was shaken under an atmosphere of hydrogen overnight. The mixture was thereafter filtered through diatomaceous earth and evaporated in vacuo. The crude product was purified by flash column chromatography (heptane:ethyl acetate; 70:30 to 35:65), to give the title compound (38 mg) as a solid. MS m/z (M+H) 412.

(c) 2-(6-piperazin-1-ylpyridin-3-yl)-1,3-benzothiazol-6-amine (title compound)

4-[5-(6-Amino-benzothiazol-2-yl)-pyridin-2-yl]-piperazine-1-carboxylic acid tert-butyl ester (13 mg, 0.032 mmol) was dissolved in DCM (1 mL), followed by addition of TFA (70 µL). The r.m. was thereafter stirred for 4 hrs at r.t. After addition of HCl (1 M; 1 mL), the two layers were separated. The organic layer was extracted with HCl (1M). The combined aqueous layers were made basic (pH 9-10) with NaOH (2 M) and extracted with DCM. The combined organic layers were washed with brine, dried ($Na_2SO_4$), filtered and the solvent was evaporated to give the title compound (10 mg) as an opac colored solid. $^1$H NMR δ 8.70 (d, 1H) 8.07 (dd, 1H) 7.67 (d, 1H) 7.13 (d, 1H) 6.97 (d, 1H) 6.81 (dd, 1H) 5.45 (s, 2H) 3.53-3.66 (m, 4H) 2.77-2.92 (m, 4H); MS m/z (M+H) 311.

Example 13

N-[2-(6-piperazin-1-ylpyridin-3-yl)-1,3-benzothiazol-6-yl]methanesulfonamide

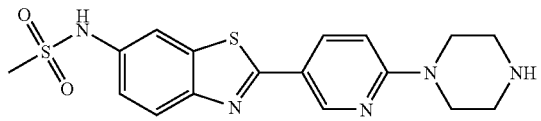

To 4-[5-(6-amino-benzothiazol-2-yl)-pyridin-2-yl]-piperazine-1-carboxylic acid tert-butyl ester (12.7 mg, 0.031 mmol) in DCM (1 mL) was added methanesulfonyl chloride (3 µL, 0.034 mmol) followed by pyridine (3 µL, 0.034 mmol). The r.m. was stirred o.n. at r.t. The crude mixture was purified by flash column chromatography (heptane:ethyl acetate; 50:50 to 40:60), to give intermediate tert-butyl 4-(5-{6-[(methylsulfonyl)amino]-1,3-benzothiazol-2-yl}pyridin-2-yl)piperazine-1-carboxylate (7.4 mg) as a solid. MS m/z (M+H) 490, (M−H) 488. This intermediate was dissolved in DCM (1 mL) and TFA (300 µL) was added. The reaction mixture was thereafter stirred for three hours at r.t. The solvent was removed in a stream of nitrogen and the residue was dissolved in DMF (400 µL) and purified by prep. HPLC, to give the title compound (3 mg) as a white solid. $^1$H NMR δ 8.71 (d, 1H) 8.09 (dd, 1H) 7.72-7.86 (m, 2H) 7.27 (dd, 1H) 6.88 (d, 1H) 3.63-3.77 (m, 4H) 2.95-3.08 (m, 4H) 2.90 (s, 3H); MS m/z M+H 390, M−H 388.

Example 14

2-[6-(4-Methylpiperazin-1-yl)pyridin-3-yl]-1,3-benzothiazol-6-amine Trifluoroacetate

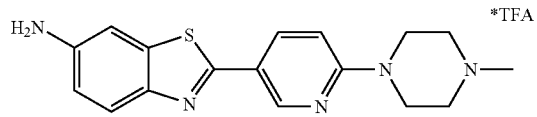

To tert-butyl 4-[5-(6-nitro-1,3-benzothiazol-2-yl)pyridin-2-yl]piperazine-1-carboxylate (0.29 g) in DCM (15 mL) was added TFA (1.5 mL) before stirring o.n. at r.t. The solvent was thereafter removed by blowing with nitrogen and the residue, crude 6-nitro-2-(6-piperazin-1-ylpyridin-3-yl)-1,3-benzothiazole (MS m/z [M+H] 342.), was used directly in the next step. To this residue in methanol (3 mL), was added formaldehyde (37% aq., 0.25 mL) and sodium cyanoborohydride (74 mg), followed by heating at 70° C. for 5 minutes. A thick solid formed and additional methanol (3 mL) was added. The mixture was stirred at r.t. for 1 h, then filtered. The solid was washed with ice-cold methanol and was then dried under vacuum over $P_2O_5$, to give intermediate 2-[6-(4-methylpiperazin-1-yl)pyridin-3-yl]-6-nitro-1,3-benzothiazole trifluoroacetate (0.26 g) as a solid. MS m/z (M+H) 356. This intermediate (0.26 g) was dissolved in methanol (8 mL) and ammonia (7M in methanol, 2 mL) was added. The flask was evacuated and flushed with argon. Palladium (10% on carbon, 30 mg) was added and the flask was evacuated and filled with hydrogen gas. The reaction mixture was shaken under an atmosphere of hydrogen o.n. at r.t. The mixture was thereafter filtered through diatomaceous earth and evaporated in vacuo, to give the title compound (0.22 g) as a white solid. $^1$H NMR (CHLOROFORM-d) δ 8.67 (d, 1H) 8.05 (dd, 1H) 7.70 (d, 1H) 7.04 (d, 1H) 6.74 (dd, 1H) 6.63 (d, 1H) 3.33-4.01 (m, 6H) 2.42-2.55 (m, 4H) 2.30 (s, 3H); MS m/z (M+H) 326.

Example 15

N-{2-[6-(4-Methylpiperazin-1-yl)pyridin-3-yl]-1,3-benzothiazol-6-yl}acetamide

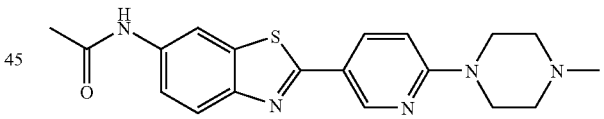

2-[6-(4-Methylpiperazin-1-yl)pyridin-3-yl]-1,3-benzothiazol-6-amine trifluoroacetate (40 mg, 0.09 mmol) was partitioned between DCM and sat. sodium hydrogencarbonate and the aqueous layer was extracted twice with DCM. The combined organic layers were dried ($Na_2SO_4$), filtered and evaporated in vacuo, giving the free amine. To the free amine in DCM (2 mL) was added acetyl chloride (0.01 mL) and pyridine (0.01 mL) and the mixture was stirred at r.t. for 1 h. The solvent was evaporated in vacuo and the residue was purified by prep. HPLC, giving the title compound (20 mg) as a pale yellow solid. $^1$H NMR (CHLOROFORM-d) δ 8.72 (d, 1H) 8.34 (s, 1H) 8.07 (dd, 1H) 7.82 (d, 1H) 7.27 (s, 1H)

7.13-7.23 (m, 1H) 6.63 (d, 1H) 3.57-3.71 (m, 4H) 2.43-2.54 (m, 4H) 2.30 (s, 3H) 2.16 (s, 3H); MS m/z (M+H) 368, (M−H) 366.

Example 16

2-[6-(4-Methylpiperazin-1-yl)pyridin-3-yl]-N-(2,2,2-trifluoroethyl)-1,3-benzothiazol-6-amine

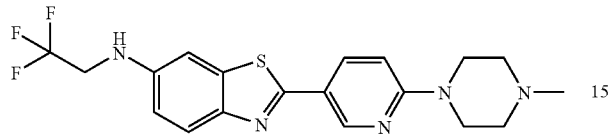

A mixture of 2-[6-(4-methylpiperazin-1-yl)pyridin-3-yl]-1,3-benzothiazol-6-amine trifluoroacetate (0.12 g, 0.27 mmol), ethyl chloroformate (36 µL, 0.38 mmol) and diisopropylethylamine (0.238 mL, 1.44 mmol) in DCM/THF (1:1, 7 mL) was stirred at r.t. overnight. Additional DCM was added before washing the sol. with sat. sodium hydrogencarbonate and then brine. The sol. was then dried ($Na_2SO_4$), filtered and evaporated in vacuo. The residue was purified by prep. HPLC, to give intermediate 2,2,2-trifluoro-N-{2-[6-(4-methylpiperazin-1-yl)pyridin-3-yl]-1,3-benzothiazol-6-yl}acetamide (43 mg). MS m/z (M+H) 422, (M−H) 420. To this intermediate (43 mg) in THF (5 mL) was added lithium aluminium hydride (12 mg, 0.3 mmol). The r.m. was refluxed for 1.5 h then allowed to come to r.t. Two drops of sat. $Na_2SO_4$, followed by ethyl acetate was added and the mixture was stirred for a few minutes. The organic layer was washed with brine, dried ($Na_2SO_4$), filtered and evaporated in vacuo. The residue was purified by prep. HPLC to yield the title compound (25 mg) as a pale yellow solid. $^1H$ NMR (MeOH-D4) δ 8.59 (d, 1H) 7.97 (dd, 1H) 7.60 (d, 1H) 7.11 (d, 1H) 6.75-6.87 (m, 2H) 3.80 (q, 2H) 3.55-3.70 (m, 4H) 2.50-2.61 (m, 4H) 2.33 (s, 3H); MS m/z (M+H) 408, (M−H) 406.

Example 17

Ethyl{2-[6-(4-Methylpiperazin-1-yl)pyridin-3-yl]-1,3-benzothiazol-6-yl}carbamate

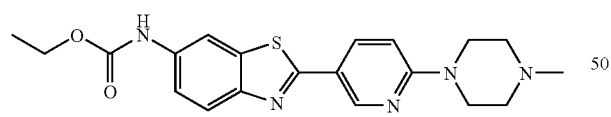

2-[6-(4-Methylpiperazin-1-yl)pyridin-3-yl]-1,3-benzothiazol-6-amine trifluoroacetate (40 mg, 0.09 mmol) was partitioned between DCM and sat. sodium hydrogencarbonate and the aqueous layer was extracted twice with DCM. The combined organic layers were dried ($Na_2SO_4$), filtered and evaporated in vacuo, giving the free amine. To the free aminen in $CH_2Cl_2$/THF (1:1, 4 mL) was added ethyl chloroformiate (15 µL, 0.15 mmol) and diisopropylethylamine (97 µL, 0.59 mmol) before stirring the r.m. at r.t. overnight. Additional DCM was then added and the organic layer was washed with sat. sodium hydrogencarbonate and brine, then dried ($Na_2SO_4$), filtered and evaporated in vacuo, to give the title compound (37 mg) as an off-white solid. $^1H$ NMR δ 9.81 (s, 1H) 8.67 (d, 1H) 8.15 (d, 1H) 8.02 (dd, 1H) 7.80 (d, 1H) 7.42 (dd, 1H) 6.91 (d, 1H) 4.09 (q, 2H) 3.50-3.64 (m, 4H) 2.30-2.38 (m, 4H) 2.16 (s, 3H) 1.20 (t, 3H); MS m/z (M+H) 398, (M−H) 396.

Example 18

N-Methyl-2-[6-(4-methylpiperazin-1-yl)pyridin-3-yl]-1,3-benzothiazol-6-amine

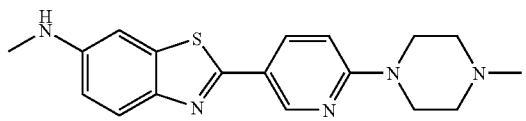

The title compound (11 mg, 38%) was prepared by reduction according to the method described for the preparation of 2-[6-(4-methylpiperazin-1-yl)pyridin-3-yl]-N-(2,2,2-trifluoroethyl)-1,3-benzothiazol-6-amine by the use of ethyl {2-[6-(4-methylpiperazin-1-yl)pyridin-3-yl]-1,3-benzothiazol-6-yl}carbamate (37 mg, 0.088 mmol) as starting material, and lithium aluminiumhydride (10 mg, 0.26 mmol) as reagent, with the following modification: The reaction mixture was stirred at reflux for 1 h then at r.t. o.n. The crude was purified by prep. HPLC, to give the title compound (11 mg) as a pale yellow solid. $^1H$ NMR (MeOH-D4) δ 8.59 (d, 1H) 7.98 (dd, 1H) 7.56 (d, 1H) 6.93 (d, 1H) 6.82 (d, 1H) 6.73 (dd, 1H) 3.55-3.69 (m, 4H) 2.74 (s, 3H) 2.48-2.60 (m, 4H) 2.32 (s, 3H); MS m/z (M+H) 340.

Example 19

2-(6-Methoxypyridin-3-yl)-1,3-benzothiazol-6-amine

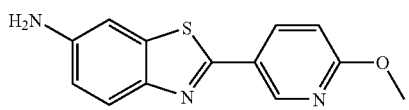

(a) 2-Bromo-1,3-benzothiazol-6-amine

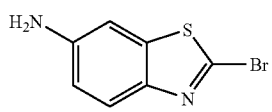

Iron (0.53 g, 9.45 mmol) was added to a sol. of 2-bromo-6-nitrobenzothiazole (0.5 g, 1.93 mmol) in acetic acid (10 mL) at r.t. After vigorous stirring for 1.5 h, additional iron (0.3 g) and acetic acid (6 mL) was added. After 5 h, the mixture was filtered and washed with ethyl acetate. The organic layer was washed with water, brine, dried ($Na_2SO_4$), filtered and concentrated. The crude product was purified by flash column chromatography (20 to 50% ethyl acetate in heptane), to give the title compound (0.12 g) as a pale pink solid. $^1H$ NMR (CHLOROFORM-d) δ 7.74 (d, 1H) 7.02 (d, 1H) 6.80 (dd, 1H) 3.85 (s, 2H); MS m/z (M+H) 229, 231.

(b) 2-(6-Methoxypyridin-3-yl)-1,3-benzothiazol-6-amine (title compound)

A mixture of 2-bromo-1,3-benzothiazol-6-amine (53 mg, 0.23 mmol), 2-methoxy-5-pyridineboronic acid (50 mg, 0.327 mmol), Pd(dppf)Cl$_2$*DCM (8 mg, 0.01 mmol) and sodium carbonate (0.1 g, 1 mmol) in THF/water (9:1, 3 mL) was heated at 140° C. for 10 minutes in a microwave reactor under argon atmosphere. The mixture was filtered and washed with THF/water (9:1). After having added DCM to the filtrate, the organic layer was washed with brine, dried (Na$_2$SO$_4$), filtered and concentrated. The crude product was purified by flash column chromatography (20 to 70% ethyl acetate in heptane), to yield the title compound (57 mg) as an off-white solid. $^1$H NMR (CHLOROFORM-d) δ 8.68 (d, 1H) 8.16 (dd, 1H) 7.74 (d, 1H) 7.06 (d, 1H) 6.70-6.81 (m, 2H) 3.94 (s, 3H) 3.77 (s, 2H); MS m/z (M+H) 258.

Example 20

N-[2-(6-Methoxypyridin-3-yl)-1,3-benzothiazol-6-yl]acetamide

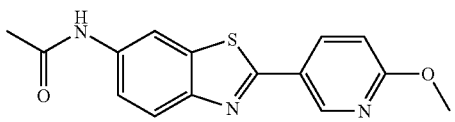

Acetylchloride (3 μL, 0.037 mmol) and pyridine (3 μL, 0.037 mmol) was added to a sol. of 2-(6-methoxypyridin-3-yl)-1,3-benzothiazol-6-amine (9 mg, 0.034 mmol) in DCM (1 mL). The r.m. was stirred at r.t. o.n. Half of the solvent was distilled of in vacuo and a few drops of hexane were added. The precipitated solid was collected and dried in vacuo, to give the title compound (4 mg) as a white solid. $^1$H NMR δ 10.30 (s, 1H) 8.91 (d, 1H) 8.57 (d, 1H) 8.39 (dd, 1H) 8.03 (d, 1H) 7.63 (dd, 1H) 7.08 (d, 1H) 4.02 (s, 3H) 2.16 (s, 3H); MS m/z (M+H) 300, (M−H) 298.

Example 21

N-[2-(6-Methoxypyridin-3-yl)-1,3-benzothiazol-6-yl]methanesulfonamide

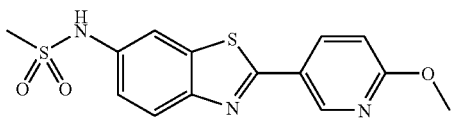

Mesylchloride (3 μL, 0.037 mmol) and pyridine (3 μL, 0.037 mmol) was added to a sol. 2-(6-methoxypyridin-3-yl)-1,3-benzothiazol-6-amine (9 mg, 0.034 mmol) in DCM (1 mL). The r.m. was stirred at r.t. for 6 days. A few drops of hexane was added and the precipitated solid was collected and dried in vacuo. The crude product was purified by flash column chromatography (20 to 100% ethyl acetate in heptane), to give the title compound (8 mg) as an off-white solid. $^1$H NMR δ 9.84 (s, 1H) 8.63 (d, 1H) 8.11 (dd, 1H) 7.77 (d, 1H) 7.71 (d, 1H) 7.14 (dd, 1H) 6.79 (d, 1H) 3.73 (s, 3H) 2.82 (s, 3H); MS m/z (M+H) 336, (M−H) 334.

Example 22

2-(6-Methoxypyridin-3-yl)-N-methyl-1,3-benzothiazol-6-amine

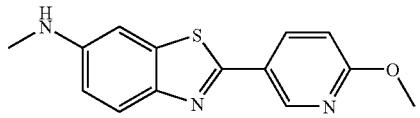

To 2-(6-methoxypyridin-3-yl)-1,3-benzothiazol-6-amine (57 mg, 0.22 mmol) in DCM/THF (1:1, 5 mL), was added ethyl chloroformate (22.5 μL, 0.24 mmol) and diisopropylethylamine (0.147 mL, 0.89 mmol), before stirring the r.m. at r.t. o.n. Additional DCM was then added and the organic layer was washed with sat. sodium hydrogencarbonate and brine, then dried (Na$_2$SO$_4$), filtered and evaporated in vacuo, to give intermediate ethyl[2-(6-methoxypyridin-3-yl)-1,3-benzothiazol-6-yl]carbamate (70 mg) as a solid. MS m/z (M+H) 330, (M−H) 328. This intermediate (70 mg) was reacted with lithium aluminiumhydride (24 mg, 0.63 mmol) according to the procedure described for the preparation of 2-[6-(4-methylpiperazin-1-yl)pyridin-3-yl]-N-(2,2,2-trifluoroethyl)-1,3-benzothiazol-6-amine. The crude product obtained was purified by prep. HPLC to give the title compound (2 mg) as a pale yellow solid. $^1$H NMR (CHLOROFORM-d) δ 8.60 (d, 1H) 8.08 (dd, 1H) 7.66 (d, 1H) 6.85 (d, 1H) 6.69 (d, 1H) 6.63 (dd, 1H) 3.86 (s, 3H) 2.77 (s, 3H); MS m/z (M+H) 272.

Example 23

6-Bromo-2-(6-methoxypyridin-3-yl)-1,3-benzothiazole

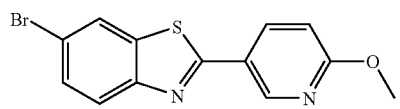

A mixture of 2,6-dibromo-benzothiazole (0.29 g, 1.0 mmol), 2-methoxy-5-pyridineboronic acid (0.17 g, 1.1 mmol), Pd(dppf)Cl$_2$*DCM (41 mg, 0.05 mmol) and sodium carbonate (0.382 g, 3.6 mmol) in THF/water (9:1, 4 mL) was heated at 140° C. for 10 minutes in a microwave reactor. The reaction mixture was thereafter filtered through a plug of silica using DCM as eluent. The filtrate was concentrated and the crude product was purified by flash column chromatography (10% ethyl acetate in heptane), followed by recrystallization from ethyl acetate, to give the title compound (61 mg) as a solid. $^1$H NMR (CHLOROFORM-d) δ 8.83 (d, 2H) 8.27

(dd, 1H) 8.03 (d, 1H) 7.90 (d, 1H) 7.60 (dd, 1H) 6.87 (d, 1H) 4.03 (s, 3H); MS m/z (M+H) 321.

Example 24

2-(6-Fluoropyridin-3-yl)-6-methoxy-1,3-benzothiazole

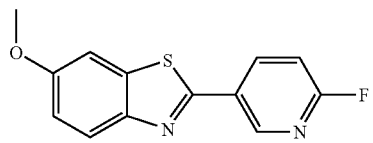

The title compound was prepared according the method described for the preparation of 6-bromo-2-(6-methoxypyridin-3-yl)-1,3-benzothiazole, by reacting 2-bromo-6-methoxy-benzothiazole (1.09 g, 4.46 mmol) with 2-fluoropyridine-5-boronic acid (0.692 g, 4.9 mmol). The crude product was purified by flash column chromatography (0 to 2% methanol in DCM), to give the title compound (0.57 g). ¹H NMR δ 8.88 (d, 1H) 8.58 (td, 1H) 7.98 (d, 1H) 7.76 (d, 1H) 7.38 (dd, 1H) 7.16 (dd, 1H) 3.86 (s, 3H); MS m/z (M+H) 261.

Example 25

5-(6-Methoxy-1,3-benzothiazol-2-yl)-N-methylpyridin-2-amine

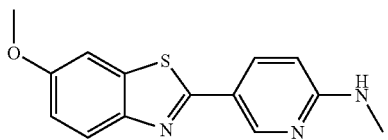

A mixture of 2-(6-fluoropyridin-3-yl)-6-methoxy-1,3-benzothiazole (0.20 g, 0.77 mmol) in methylamine (8M in ethanol, 5 mL) was heated at 100° C. for 5 minutes in a microwave reactor. The mixture was diluted with water and the solid product was collected by filtration and dried in vacuo, to yield the title compound (0.17 g) as a solid. ¹H NMR δ 8.64 (d, 1H) 7.97 (dd, 1H) 7.83 (d, 1H) 7.64 (d, 1H) 7.21 (d, 1H) 7.07 (dd, 1H) 6.58 (d, 1H) 3.83 (s, 3H) 2.85 (d, 3H); MS m/z (M+H) 271.9.

Example 26

5-(6-Methoxy-1,3-benzothiazol-2-yl)-N-(pyridin-3-ylmethyl)pyridin-2-amine

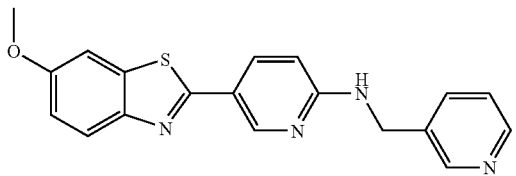

A mixture of 2-(6-fluoropyridin-3-yl)-6-methoxy-1,3-benzothiazole (0.10 g, 0.38 mmol) and 3-(aminomethyl)pyridine (1.0 mL, 9.5 mmol) in ethanol (4 mL) was heated at 100° C. for 9 minutes in a microwave reactor. The mixture was diluted with water, then cooled to r.t. and the formed precipitate was collected by filtration and dried. The crude product was purified by prep. HPLC to give the title compound (71 mg) as a solid. ¹H NMR (CHLOROFORM-d) δ 8.75 (d, 1H) 8.66 (d, 1H) 8.56 (dd, 1H) 8.11 (dd, 1H) 7.89 (d, 1H) 7.66-7.76 (m, 1H) 7.34 (d, 1H) 7.26-7.31 (m, 2H) 7.07 (dd, 1H) 6.50 (d, 1H) 5.18 (t, 1H) 4.67 (d, 2H) 3.90 (s, 3H); MS m/z (M+H) 348.9.

Example 27

2-[6-(Methylamino)pyridin-3-yl]-1,3-benzothiazol-6-ol

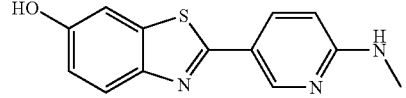

A mixture of 5-(6-methoxy-1,3-benzothiazol-2-yl)-N-methylpyridin-2-amine (50 mg, 0.18 mmol) and tetrabutylammonium bromide (catalytical amount) in hydrogen bromide (48% aq., 2 mL) was heated at 120° C. for 10 minutes in a microwave reactor. The solution was neutralized with sodium hydrogencarbonate and the aqueous layer was extracted twice with chloroform. The combined organic layers were evaporated in vacuo, and the crude product was purified by prep. HPLC to give the title compound (22 mg) as a solid. ¹H NMR 9.78 (s, 1H) 8.60 (d, 1H) 7.94 (dd, 1H) 7.73 (d, 1H) 7.35 (d, 1H) 7.17 (q, 1H) 6.93 (dd, 1H) 6.57 (d, 1H) 2.85 (d, 3H); MS m/z (M+H) 357.9.

Example 28

5-(6-Methoxy-1,3-benzothiazol-2-yl)pyridin-2-amine

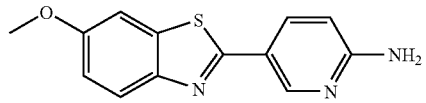

A mixture of 2-bromo-6-methoxy-benzothiazole (1.14 g), 5-(4,4,5,5-tetramethyl-1,3,2-dioxaborolan-2-yl)pyridin-2-amine (1.23 g, 1.2 eq.), Pd(dppf)Cl₂*DCM (170 mg, 0.05 eq.) and 2.0 M aq. K₂CO₃ (10 ml, 4 eq.) in DMF (20 ml) was heated at 80° C. for 2 h under argon while stirring. Ethyl acetate (200 ml) was subsequently added before concentrating the sol. onto diatomaceous earth in vacuo. Purification by flash chromatography (DCM:methanol, 99:1 to 95:5) provided the title compound (730 mg) as a yellow solid. ¹H NMR δ 8.56 (d, 1H) 7.96 (dd, 1H) 7.82 (d, 1H) 7.64 (d, 1H) 7.07 (dd, 1H) 6.67 (br. s, 2H) 6.55 (d, 1H) 3.83 (s, 3H); MS m/z (M+H) 258.1.

Example 29

[N-Dimethyl-3H$_6$]-[5-(6-Methoxy-benzothiazol-2-yl)-pyridin-2-yl]-dimethyl-amine

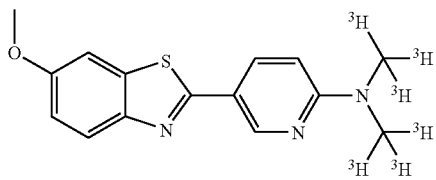

5-(6-Methoxy-benzothiazol-2-yl)-pyridin-2-ylamine (0.7 mg, 2.7 µmol) was mixed with [$^3$H]methyl iodide (100 mCi, 1.2 µmol) in DMF (0.4 mL) with sodium hydride (4 mg) as base and heated to 50° C. for 1 h. The reaction mixture was purified by reversed phase HPLC to afford the title compound (8.4 mCi, 8%). MS m/z (M+H) 298.

Example 30

[N-Dimethyl-$^3$H$_6$]-2-(6-Dimethylamino-pyridin-3-yl)-benzothiazol-6-ol

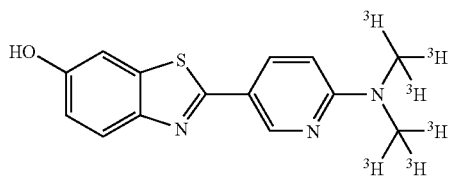

[N-Dimethyl-3H$_6$]-[5-(6-Methoxy-benzothiazol-2-yl)-pyridin-2-yl]-dimethyl-amine (5 mCi, 0.06 µmol) was mixed with sodium thiophenoxide (4 mg) in N-methylpyrrolidinone (0.4 mL) and heated to 25° C. for 10 min by means of a microwave reactor. The reaction mixture was purified by reversed phase HPLC to afford the title compound (4.6 mCi, 92%). MS m/z M+H 284; $^3$H NMR (proton decoupled in CD$_3$OD) δ 2.90 (s, CHT$_2$) 2.88 (s, CT$_3$) with the relative intensities 1:9.1.

Example 31

[N-Methyl-3H$_3$]-[5-(6-Methoxy-benzothiazol-2-yl)-pyridin-2-yl]-methyl-amine

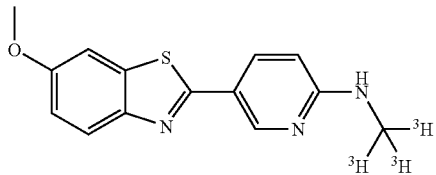

5-(6-Methoxy-benzothiazol-2-yl)-pyridin-2-ylamine (3.6 mg, 14 µmol) was mixed with [$^3$H]methyl iodide (30 mCi, 0.35 µmol) in dimethylformamide (0.4 mL) with sodium hydride (24 mg) as base and heated to 60° C. for 30 min. The reaction mixture was purified by reversed phase HPLC to afford the title compound (17 mCi, 57%). MS m/z M+H 278.

Example 32

[N-Methyl-3H$_3$]-2-(6-Methylamino-pyridin-3-yl)-benzothiazol-6-ol

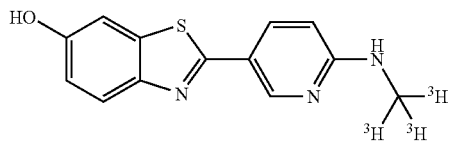

[N-Methyl-3H$_3$]-[5-(6-Methoxy-benzothiazol-2-yl)-pyridin-2-yl]-methyl-amine (12.7 mCi, 0.15 µmol) was mixed with sodium thiophenoxide (4.4 mg) in N-methylpyrrolidinone (0.4 mL) and heated to 250° C. for 20 min by means of a microwave reactor. The reaction mixture was purified by reversed phase HPLC to afford the title compound (11 mCi, 87%). MS m/z M+H 264; $^3$H NMR (proton decoupled in CD$_3$OD) δ 3.14 (s, CHT$_2$) 3.11 (s, CT$_3$) with the relative intensities 1:9.6.

Example 33

5-(6-Methoxy-1,3-benzothiazol-2-yl)-N,N-dimethylpyridin-2-amine

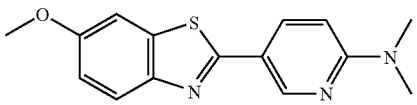

2-(6-Fluoropyridin-3-yl)-6-methoxy-1,3-benzothiazole (0.201 g) and 2 M dimethylamine in THF (5 mL) were heated in a microwave oven at 100° C. for 5 min. Water was added and the precipitated product was filtered off, washed with water and dried in a desicator over P$_2$O$_5$ to yield 0.193 g of the product as a pale beige solid. $^1$H NMR δ ppm 8.71 (d, 1H) 8.07 (dd, 1H) 7.84 (d, 1H) 7.65 (d, 1H) 7.08 (dd, 1H) 6.77 (d, 1H) 3.84 (s, 3H) 3.12 (s, 6H); MS m/z (M+H) 286.

Example 34

2-[6-(Dimethylamino)pyridin-3-yl]-1,3-benzothiazol-6-ol

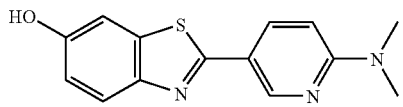

5-(6-Methoxy-1,3-benzothiazol-2-yl)-N,N-dimethylpyridin-2-amine (131 mg) was subjected to the procedure used for the preparation of 2-[6-(methylamino)pyridin-3-yl]-1,3-benzothiazol-6-ol. After neutralization, the aq. phase was extracted with dichloromethane (3×), dried (MgSO₄), filtered and the solvent removed in vacuo. Recrystallization from methanol gave the title compound (75 mg) as a pale beige solid. ¹H NMR δ ppm 9.75 (s, 1H) 8.68 (d, 1H) 8.04 (dd, 1H) 7.75 (d, 1H) 7.36 (d, 1H) 6.93 (dd, 1H) 6.77 (d, 1H) 3.12 (s, 6H); MS m/z (M+H) 272.

Example 35

2-(2-Methoxypyrimidin-5-yl)-1,3-benzothiazole

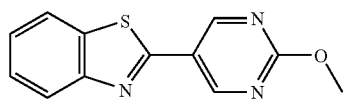

To 1,3-benzothiazole (0.100 g, 0.74 mmol) in dry DMF (3.5 mL) were added 5-bromo-2-methoxypyrimidine (0.168 g, 0.89 mmol), Cu(I)Br (23 mg, 0.16 mmol), cesium carbonate (0.242 g, 0.74 mmol) and bis(tri-t-butylphosphine) palladium (0) (38 mg, 0.075 mmol) and the reaction was heated in a sealed tube under argon at 150° C. for 1 h. Water and dichloromethane were added and the layers separated. The aqueous layer was extracted with dichloromethane (3×). The combined organic phases were washed with water and brine, dried (MgSO₄), filtered and the solvent was removed in vacuo. The crude material was purified by flash chromatography (Heptane/EtOAc 1:1) to give the title compound (71 mg) as a pale brown solid. ¹H NMR δ ppm 9.26 (s, 2H) 8.20 (d, 1H) 8.09 (d, 1H) 7.55-7.61 (m, 1H) 7.46-7.53 (m, 1H) 4.04 (s, 3H); MS m/z (M+H) 244.

Example 36

5-(5-Methoxy-1,3-benzothiazol-2-yl)-N-methylpyridin-2-amine

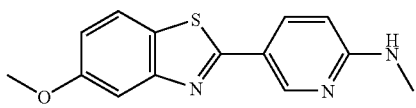

(a) 6-Fluoro-N-(3-methoxyphenyl)nicotinamide

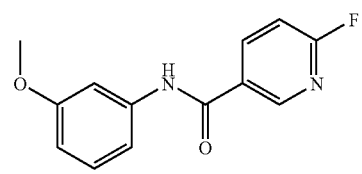

To a solution of 3-methoxyaniline (3.00 g, 24.4 mmol), 6-fluoronicotinic acid (4.41 g, 31.3 mmol) and 4-dimethylaminopyridine (DMAP) (0.298 g, 2.44 mmol) in dichloromethane (210 mL) was added, under an atmosphere of nitrogen, a solution of N,N'-dicyclohexylcarbodiimide (6.48 g, 31.4 mmol) in DCM (60 mL) dropwise at 0° C. The solution was then allowed to warm to rt and stirred for 1 h. The reaction mixture was filtered and the organic phase was washed with sat. aq. NaHCO₃, water and brine. The organic phase was dried (MgSO₄), filtered and the solvent removed in vacuo to give the title compound (quant.) as an orange solid that was taken to the next step without further purification. MS m/z (M+H) 247.

(b) 6-Fluoro-N-(3-methoxyphenyl)pyridine-3-carbothioamide

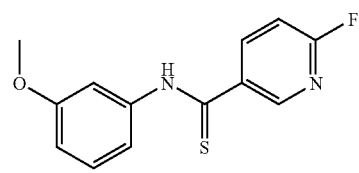

6-Fluoro-N-(3-methoxyphenyl)nicotinamide (1.00 g, 4.07 mmol) was dispersed in toluene (20 mL), and hexamethyldisiloxane (1.65 mL, 7.73 mmol) was added with stirring under argon. The reaction mixture was heated to 60° C. and phosphorus pentasulfide (2.23 g) was added with further toluene (7 mL) and the reaction mixture was heated at 100° C. for 3.5 h. After cooling to rt, toluene was removed in vacuo and water and DCM were added and the layers separated. The aqueous phase was extracted with DCM (3×). The combined organic phases were washed with water, dried (MgSO₄), filtered and the solvent removed in vacuo. The crude material was purified by column chromatography (heptane/EtOAc 60:40) to give the title compound (0.337 g) as a yellow oil. ¹H NMR δ ppm 11.98 (s, 1H) 8.64 (d, 1H) 8.31-8.46 (m, 1H) 7.58 (t, 1H) 7.23-7.49 (m, 3H) 6.89 (dd, 1H) 3.78 (s, 3H); MS m/z (M+H) 263.

(c) 2-(6-Fluoropyridin-3-yl)-5-methoxy-1,3-benzothiazole

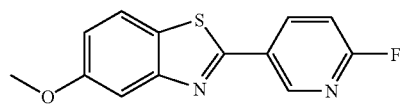

6-Fluoro-N-(3-methoxyphenyl)pyridine-3-carbothioamide (0.317 g, 1.21 mmol) was first wetted with ethanol, and NaOH (30% aq, 0.30 mL) was added. The mixture was diluted with water to provide a final suspension of 10% NaOH. Aliquots of this mixture were added at 1 min intervals to a stirred solution of potassium hexacyanoferrate(III) (1.59 g, 4.84 mmol) in water (3.2 mL) at 85° C. The reaction mixture was then heated at 85° C. for another 45 minutes. After cooled to rt, water and DCM were added and the layers separated. The aqueous phase was extracted with DCM (3×). The combined organic phases were dried (MgSO₄), filtered and the solvent removed in vacuo. The crude material was purified by column chromatography (DCM) to give the title compound (61 mg) as a pale yellow solid. ¹H NMR (400 MHz, CHLOROFORM-d) δ ppm 8.89 (d, 1H) 8.44-8.52 (m, 1H) 7.77 (d, 1H) 7.57 (d, 1H) 7.04-7.12 (m, 2H) 3.92 (s, 3H); MS m/z (M+H) 261.

(d) 5-(5-Methoxy-1,3-benzothiazol-2-yl)-N-methylpyridin-2-amine (title compound)

To 2-(6-fluoropyridin-3-yl)-5-methoxy-1,3-benzothiazole (59.2 mg, 0.227 mmol) was added methylamine in ethanol (8

M, 2 mL) and the reaction mixture was heated in a microwave oven at 100° C. for 5 min. Water and dichloromethane were added and the layers separated. The aqueous phase was extracted with dichloromethane (3×). The combined organic phases were washed with water, dried (MgSO$_4$), filtered and the solvent removed in vacuo. The crude material was purified by column chromatography (heptane/EtOAc 60:40 to 50:50) to give the title compound (39 mg) as a pale yellow solid. $^1$H NMR δ ppm 8.68 (d, 1H) 7.98 (dd, 1H) 7.91 (d, 1H) 7.50 (d, 1H) 7.27 (q, 1H) 7.01 (dd, 1H) 6.59 (d, 1H) 3.85 (s, 3H) 2.86 (d, 3H); MS m/z (M+H) 272.

Example 37

2-[6-(Methylamino)pyridin-3-yl]-1,3-benzothiazol-5-ol

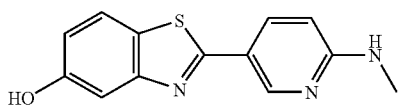

5-(5-Methoxy-1,3-benzothiazol-2-yl)-N-methylpyridin-2-amine (29.6 mg, 0.109 mmol) was subjected to the procedure used for the preparation of 2-[6-(methylamino)pyridin-3-yl]-1,3-benzothiazol-6-ol. After neutralization, the precipitated product was filtered off, washed with water and EtOAc and dried under vacuum to afford the title compound (23 mg) as a yellow solid. $^1$H NMR δ ppm 9.57 (br s, 1H) 8.45 (d, 1H) 7.78 (dd, 1H) 7.59 (d, 1H) 6.98-7.16 (m, 2H) 6.67 (dd, 1H) 6.38 (d, 1H) 2.66 (d, 3H); MS m/z (M+H) 258.

Example 38

2-[6-(Methylamino)pyridin-3-yl]-1,3-benzothiazol-5-amine

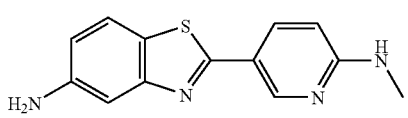

The title compound was prepared according to the method used for the preparation of 2-(2-methoxypyrimidin-5-yl)-1,3-benzothiazole, now starting from 1,3-benzothiazol-5-amine (50 mg, 0.33 mmol) and 5-bromo-N-methylpyridin-2-amine (75 mg, 0.40 mmol). The is crude material was purified on a preparative HPLC to give the title compound (12 mg) as a pale beige solid. $^1$H NMR δ ppm 8.62 (d, 1H) 7.95 (dd, 1H) 7.61 (d, 1H) 7.19 (q, 1H) 7.07 (d, 1H) 6.69 (dd, 1H) 6.56 (d, 1H) 5.24 (s, 2H) 2.85 (d, 3H); MS m/z (M+H) 257.

Example 39

N-Ethyl-5-(6-methoxy-1,3-benzothiazol-2-yl)pyridin-2-amine

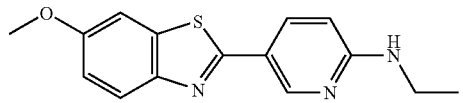

In a microwave vial were added 2-(6-fluoropyridin-3-yl)-6-methoxy-1,3-benzothiazole (75 mg, 0.289 mmol), water (1.2 mL) and ethylamine in water (70%, 1.2 mL) and the reaction was heated in a microwave oven at 100° C. for 5 min. The precipitated product was filtered off, washed with water and dried in a desicator over P$_2$O$_5$ to yield the product (67 mg) as a white solid. $^1$H NMR δ ppm 8.62 (d, 1H) 7.95 (dd, 1H) 7.82 (d, 1H) 7.64 (d, 1H) 7.23 (t, 1H) 7.07 (dd, 1H) 6.57 (d, 1H) 3.83 (s, 3H) 3.33-3.40 (m, 2H) 1.16 (t, 3H); MS m/z (M+H) 286.

Example 40

2-[6-(Ethylamino)pyridin-3-yl]-1,3-benzothiazol-6-ol

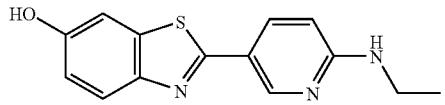

To N-ethyl-5-(6-methoxy-1,3-benzothiazol-2-yl)pyridin-2-amine (52.8 mg, 0.185 mmol) in dichloromethane (2 mL) was added BBr$_3$ in dichloromethane (1 M, 925 μL) at 0° C. under an argon atmosphere. The reaction was then stirred at 0° C. for 3 h before it was neutralized with NaHCO$_3$ (sat aq). The precipitated product was filtered off, washed with water and DCM and dried. Recrystallization from (MeOH/toluene) gave the title compound (11 mg) as a white solid. $^1$H NMR δ ppm 9.75 (br s, 1H) 8.58 (d, 1H) 7.93 (dd, 1H) 7.73 (d, 1H) 7.34 (d, 1H) 7.19 (t, 1H) 6.92 (dd, 1H) 6.56 (d, 1H) 3.32-3.38 (m, 2H) 1.16 (t, 3H); MS m/z (M+H) 272.

Example 41

N-Ethyl-5-(6-methoxy-1,3-benzothiazol-2-yl)-N-methylpyridin-2-amine

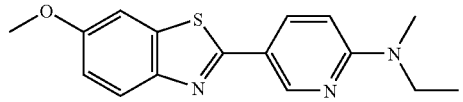

In a microwave vial were added 2-(6-fluoropyridin-3-yl)-6-methoxy-1,3-benzothiazole (75 mg, 0.289 mmol), water (2.0 ml-L) and ethylmethylamine (0.50 mL) and the reaction was heated in a microwave oven at 100° C. for 5 min. The precipitated product was filtered off, washed with water and dried in a desicator over P₂O₅ to yield the product (70 mg) as a beige solid. ¹H NMR δ ppm 8.71 (d, 1H) 8.06 (dd, 2.53 Hz, 1H) 7.85 (d, 1H) 7.66 (d, 1H) 7.08 (dd, 1H) 6.76 (d, 1H) 3.84 (s, 3H) 3.64 (q, 2H) 3.08 (s, 3H) 1.12 (t, 3H); MS m/z (M+H) 300.

Example 42

2-{6-[Ethyl(methyl)amino]pyridin-3-yl}-1,3-benzothiazol-6-ol

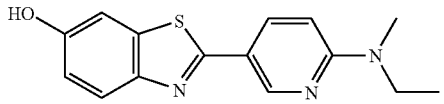

N-Ethyl-5-(6-methoxy-1,3-benzothiazol-2-yl)-N-methylpyridin-2-amine (55.4 mg, 0.185 mmol) was subjected to the procedure described for 2-[6-(ethylamino)pyridin-3-yl]-1,3-benzothiazol-6-ol. Recrystallization from methanol gave 23.7 mg of the title compound as a pale yellow solid. ¹H NMR δ ppm 9.75 (s, 1H) 8.67 (d, 1H) 8.03 (dd, 1H) 7.75 (d, 1H) 7.35 (d, 1H) 6.93 (dd, 1H) 6.75 (d, 1H) 3.63 (q, 2H) 3.07 (s, 3H) 1.11 (t, 3H); MS m/z (M+H) 286.

Example 43

6-Methoxy-2-[5-(trifluoromethyl)pyridin-2-yl]-1,3-benzothiazole

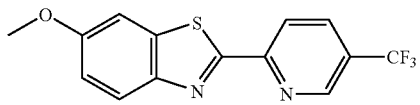

6-Methoxy-1,3-benzothiazole (35 mg, 0.21 mmol) and 2-bromo-5-(trifluoromethyl)pyridine (1.1 equiv) were dissolved in dry, degassed DMF (1.5 mL). Cesium carbonate (72.5 mg, 0.22 mmol) and bis(tri-t-butylphosphine) palladium (0) (5.5 mg, 0.0111 mmol) were added and the reaction was heated under argon at 150° C. for 3 h. After cooling to about 40° C., the reaction mixture was filtered, and the filter was washed with DMF. The filtrate was concentrated in a centrifuge, and the residue was taken up in DMSO and purified by preparative HPLC to give the title compound (11 mg) as a yellow solid. ¹H NMR (400 MHz, CHLOROFORM-d) δ ppm 8.88-8.95 (m, 1H) 8.44 (d, 1H) 8.06 (dd, 1H) 8.00 (d, 1H) 7.42 (d, 1H) 7.15 (dd, 1H) 3.93 (s, 3H); MS m/z (M+H) 311.

Example 44

2-(5-Fluoropyridin-2-yl)-6-methoxy-1,3-benzothiazole

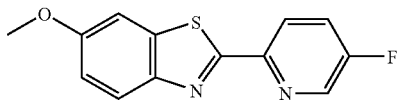

6-Methoxy-1,3-benzothiazole (35 mg, 0.21 mmol) and 2-bromo-5-fluoropyridine (1.1 equiv) were reacted according to the procedure used for the preparation of 6-methoxy-2-[5-(trifluoromethyl)pyridin-2-yl]-1,3-benzothiazole. This gave the title compound (6 mg) as a yellow solid. ¹H NMR (400 MHz, CHLOROFORM-d) δ ppm 8.52 (d, 1H) 8.35 (dd, 1H) 7.96 (d, 1H) 7.51-7.59 (m, 1H) 7.40 (d, 1H) 7.12 (dd, 1H) 3.92 (s, 3H); MS m/z (M+H) 261.

Example 45

6-Methoxy-2-[5-(methylsulfonyl)pyridin-2-yl]-1,3-benzothiazole

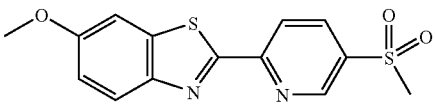

6-Methoxy-1,3-benzothiazole (35 mg, 0.21 mmol) and 2-bromo-5-(methylsulfonyl)pyridine (1.1 equiv) were reacted according to the procedure used for the preparation of 6-methoxy-2-[5-(trifluoromethyl)pyridin-2-yl]-1,3-benzothiazole. This gave the title compound (3 mg) as a brown solid. ¹H NMR (400 MHz, MeOH) δ ppm 9.11 (d, 1H) 8.46 (d, 1H) 8.34 (dd, 1H) 7.96 (d, 1H) 7.41 (d, 1H) 7.13 (dd, 1H) 3.89 (s, 3H) 3.17 (s, 3H); MS m/z (M+H) 321.

Example 46

2-(6-Ethoxypyridin-3-yl)-6-methoxy-1,3-benzothiazole

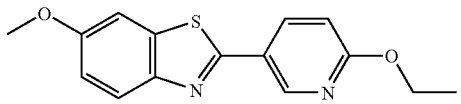

6-Methoxy-1,3-benzothiazole (35 mg, 0.21 mmol) and 2-bromo-5-ethoxypyridine (1.1 equiv) were reacted according to the procedure used for the preparation of 6-methoxy-2-[5-(trifluoromethyl)pyridin-2-yl]-1,3-benzothiazole. This gave the title compound (17 mg) as a pale beige solid. ¹H NMR δ ppm 8.81 (d, 1H) 8.30 (dd, 1H) 7.93 (d, 1H) 7.72 (d, 1H) 7.13 (dd, 1H) 6.97 (d, 1H) 4.40 (q, 2H) 3.85 (s, 3H) 1.36 (t, 3H); MS m/z (M+H) 287.

Example 47

6-Methoxy-2-(2-piperazin-1-ylpyrimidin-5-yl)-1,3-benzothiazole

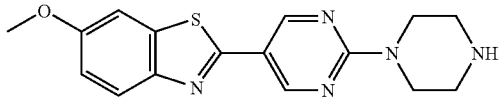

6-Methoxy-1,3-benzothiazole (35 mg, 0.21 mmol) and 5-bromo-2-piperazin-1-ylpyrimidine (1.1 equiv) were reacted according to the procedure used for the preparation of 6-methoxy-2-[5-(trifluoromethyl)pyridin-2-yl]-1,3-benzothiazole. This gave the title compound (3 mg) as a yellow solid. ¹H NMR (400 MHz, MeOH) δ ppm 8.84 (s, 2H) 7.83 (d, 1H) 7.30 (d, 1H) 7.04 (dd, 1H) 3.87-3.94 (m, 4H) 3.84 (s, 3H) 2.90-2.99 (m, 4H); MS m/z (M+H) 328.

Example 48

5-(6-Methoxy-1,3-benzothiazol-2-yl)-N,N-dimethylpyrimidin-2-amine

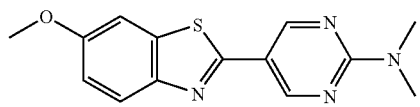

6-Methoxy-1,3-benzothiazole (0.165 g, 1.00 mmol) and 5-bromo-N,N-dimethylpyrimidin-2-amine (0.242 g, 1.20 mmol) were reacted according to the procedure used for the preparation of 2-(2-methoxypyrimidin-5-yl)-1,3-benzothiazole with the exception that the reaction was heated at 170° C. in a microwave reactor for 3 h. Purification by flash chromatography (Heptane/EtOAc gradient) followed by recrystallization from acetonitrile gave the title compound (10 mg) as colorless needle crystals. ¹H NMR (CHLOROFORM-d) δ 8.92 (s, 2H) 7.90 (d, 1H) 7.34 (d, 1H) 7.08 (dd, 1H) 3.90 (s, 3H) 3.29 (s, 6H); MS m/z (M+H) 287.

Example 49

2-[2-(Dimethylamino)pyrimidin-5-yl]-1,3-benzothiazol-6-ol

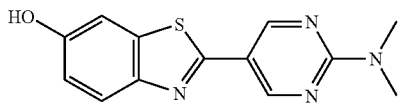

To a stirred slurry of 5-(6-methoxy-1,3-benzothiazol-2-yl)-N,N-dimethylpyrimidin-2-amine (0.196 mg, 0.68 mmol) in DCM (2 mL) at 0° C. under argon, was added BBr₃ (1 M in DCM, 4.1 mL) from a syringe. After 5 min of stirring, the reaction mixture was allowed to reach rt over 6.5 h, while being stirred under a drying tube (CaCl₂). Then sat. aq. NaHCO₃ was carefully added and the mixture was vigorously stirred at rt on before it was concentrated under vacuum. The residue was dissolved in MeOH, concentrated on and filtered through silica (EtOAc/MeOH 10:1). Purification by HPLC gave the title compound (12 mg) as yellow solid. ¹H NMR δ 8.89 (s, 2H) 7.79 (d, 1H) 7.39 (d, 1H) 6.96 (dd, 1H) 3.22 (s, 6H); MS m/z (M+H) 273.

Example 50

5-(6-Methoxy-1,3-benzothiazol-2-yl)-N-methylpyrimidin-2-amine

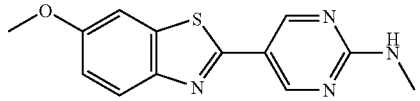

6-Methoxy-1,3-benzothiazole (0.100 g, 0.61 mmol) and 5-bromo-N-methylpyrimidin-2-amine (0.171 g, 0.91 mmol) were reacted according to the procedure used for the preparation of 2-(2-methoxypyrimidin-5-yl)-1,3-benzothiazole with the exception that the reaction was heated at 170° C. in a microwave reactor for 1.5 h. The reaction mixture was diluted with EtOAc and water and the mixture was filtered. The phases were separated and the aqueous layer was extracted with EtOAc (3×). The organic phase was washed with brine (2×), dried (MgSO₄) and concentrated under vacuum. Flash chromatography (Heptane/EtOAc gradient) gave the title compound (54 mg) as a yellow solid. ¹H NMR (CHLOROFORM-d) δ 8.93 (s, 2H) 7.91 (d, 1H) 7.35 (d, 1H) 7.10 (dd, 1H) 5.53 (br s, 1H) 3.90 (s, 3H) 3.11 (d, 3H); MS m/z (M+H) 273.

Example 51

2-[2-(Methylamino)pyrimidin-5-yl]-1,3-benzothiazol-6-ol

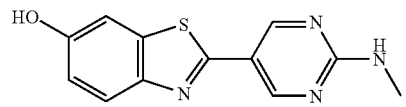

5-(6-Methoxy-1,3-benzothiazol-2-yl)-N-methylpyrimidin-2-amine (0.146 g, 0.54 mmol) was reacted according to the procedure used for the preparation of 2-[2-(dimethylamino)pyrimidin-5-yl]-1,3-benzothiazol-6-ol. The residue obtained after evaporation was purified by HPLC to afford the title compound (11 mg). ¹H NMR δ 8.96 (br s, 1H) 8.86 (s, 1H) 8.82 (s, 1H) 7.81-7.76 (m, 2H) 7.39 (d, 1H) 6.95 (dd, 1H) 2.88 (d, 3H); MS m/z (M+H) 259.

Example 52

5-(6-Methoxy-1,3-benzothiazol-2-yl)pyrimidin-2-amine

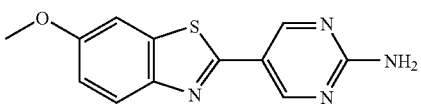

A mixture of 2-bromo-6-methoxy-1,3-benzothiazole (0.300 g, 1.23 mmol), 5-(4,4,5-trimethyl-1,3,2-dioxaborolan-2-yl)pyrimidin-2-amine (0.326 g, 1.47 mmol), Pd(dppf)Cl₂*DCM (50 mg, 0.061 mmol) and 2 M aq. K₂CO₃ (3 mL) in DMF (7 mL) was stirred under argon at 80° C. for 1 h. The reaction mixture was allowed to reach rt and was filtered through silica. The filter cake was washed with DCM and DMF. The filtrate was concentrated under vacuum. Flash chromatography (Heptane/EtOAc gradient) of the residue gave the title compound (0.171 g) as a yellow solid. ¹H NMR δ ppm 8.83 (s, 2H) 7.87 (d, 1H) 7.70 (d, 1H) 7.35 (br s, 2H) 7.11 (dd, 1H) 3.84 (s, 3H); MS m/z (M+H) 259.

Example 53

6-Methoxy-2-(2-methoxypyrimidin-5-yl)-1,3-benzothiazole

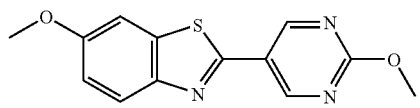

6-Methoxy-1,3-benzothiazole (30 mg, 0.18 mmol) and 5-bromo-2-methoxypyrimidine (41 mg, 0.22 mmol) were reacted according to the procedure used for the preparation of 2-(2-methoxypyrimidin-5-yl)-1,3-benzothiazole with the exception that the reaction was heated at 150° C. in a microwave reactor for 15 min. Purification by flash chromatography (Heptane/EtOAc 3:1) gave the title compound (13 mg) as a white solid. ¹H NMR (CHLOROFORM-d) δ 9.13 (s, 2H) 7.97 (d, 1H) 7.38 (d, 1H) 7.13 (dd, 1H) 4.12 (s, 3H) 3.92 (s, 3H); MS m/z (M+H) 274.

Example 54

6-(6-Methoxy-1,3-benzothiazol-2-yl)pyridin-3-amine

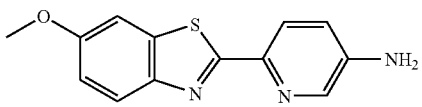

6-Methoxy-1,3-benzothiazole (60 mg, 0.36 mmol) and 6-bromopyridin-3-amine (76 mg, 0.44 mmol) were reacted according to the procedure used for the preparation of 2-(2-methoxypyrimidin-5-yl)-1,3-benzothiazole with the exception that the reaction was heated at 170° C. in a microwave reactor for 1.5 h. Water and EtOAc were added and the mixture was filtered. The phases of the filtrate were separated and the aqueous layer was extracted with EtOAc (3×). The organic phase was washed with brine, dried (MgSO₄) and concentrated under vacuum. Purification by flash chromatography (Heptan/EtOAc) followed by preparative HPLC gave the title compound (22 mg) as an off-white solid. ¹H NMR (CHLOROFORM-d) δ 8.16-8.11 (m, 2H) 7.91 (d, 1H) 7.38 (d, 1H) 7.11-7.05 (m, 2H) 4.01 (br s, 2H) 3.91 (s, 3H); MS m/z (M+H) 258.

Example 55

6-(6-Methoxy-1,3-benzothiazol-2-yl)-N,N-dimethylpyridin-3-amine

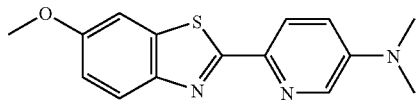

6-Methoxy-1,3-benzothiazole (0.136 g, 0.82 mmol; M. A. Matulenko et al. *Bioorg. Med. Chem.* 2005, 13, 3705.) and 6-bromo-N,N-dimethylpyridin-3-amine (0.199 g, 0.99 mmol) were reacted according to the procedure used for the preparation of 6-methoxy-2-[5-(trifluoromethyl)pyridin-2-yl]-1,3-benzothiazole, with the following exceptions: 10 mol % bis(tri-t-butylphosphine) palladium (0) was used, the amount of DMF was reduced (2 mL) and the reaction mixture was heated at 150° C. for 4.5 h before it was filtered through a short plug of silica that was rinsed by DCM and DMF. The solvents were evaporated under reduced pressure and the residue was subjected to flash chromatography (Heptane/EtOAc gradient). The title compound (0.100 g) was isolated as a yellow solid. ¹H NMR (CHLOROFORM-d) δ 8.19-8.15 (m, 2H) 7.90 (d, 1H) 7.38 (d, 1H) 7.09-7.04 (m, 2H) 3.90 (s, 3H) 3.10 (s, 6H); MS m/z (M+H) 286.

Example 56

2-[5-(Dimethylamino)pyridin-2-yl]-1,3-benzothiazol-6-ol

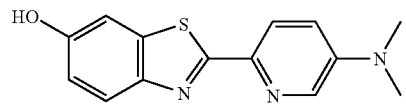

To a stirred solution of 6-(6-methoxy-1,3-benzothiazol-2-yl)-N,N-dimethylpyridin-3-amine (61 mg, 0.21 mmol) in DCM (1 mL) at 0° C. under argon, was added BBr₃ (1 M in DCM, 1.1 mL) from a syringe. After 5 min of stirring, the reaction mixture was allowed to reach rt on while being stirred under a drying tube (CaCl₂). Then sat. aq. NaHCO₃ was carefully added and the mixture was vigorously stirred for another 4 h at rt. DCM was evaporated under reduced pressure and the aqueous phase was continuously extracted with EtOAc on. The organic layer was concentrated to give the title compound (15 mg) as a yellow solid. ¹H NMR δ ppm 9.74 (s, 1H) 8.16 (d, 1H) 8.01 (d, 1H) 7.76 (d, 1H) 7.33 (d, 1H) 7.21 (dd, 1H) 6.93 (dd, 1H) 3.04 (s, 6H); MS m/z (M+H) 272.

Example 57

6-Methoxy-2-(6-morpholin-4-ylpyridin-3-yl)-1,3-benzothiazole

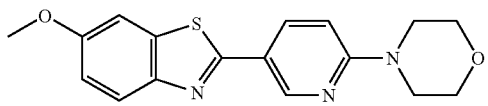

2-Bromo-6-methoxy-1,3-benzothiazole (49 mg, 0.20 mmol), 4-[5-(4,4,5,5-tetramethyl-1,3,2-dioxaborolan-2-yl)pyridin-2-yl]morpholine (70 mg, 0.24 mmol) were reacted according to the procedure used for the preparation of 5-(6-methoxy-1,3-benzothiazol-2-yl)pyrimidin-2-amine, with the following exceptions: The reaction was heated for 4 h before the solvent was evaporated under reduced pressure. The residue was dissolved in MeOH/DCM 1:1 and filtered through silica. The filtrate was concentrated and the crude product was purified by preparative HPLC to give the title compound (0.6 mg). $^1$H NMR (CHLOROFORM-d) δ 8.79 (d, 1H) 8.18 (dd, 1H) 7.90 (d, 1H) 7.35 (d, 1H) 7.08 (dd, 1H) 6.71 (d, 1H) 3.90 (s, 3H) 3.87-3.83 (m, 4H) 3.67-3.63 (m, 4H); MS m/z (M+H) 328.

Example 58

2-(6-Aminopyridin-3-yl)-1,3-benzothiazol-6-ol

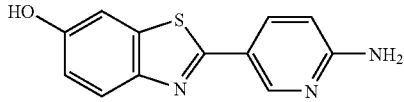

5-(6-Methoxy-1,3-benzothiazol-2-yl)pyridin-2-amine (190 mg, 0.74 mmol) was exposed to the procedure used for the preparation of 2-[6-(methylamino)pyridin-3-yl]-1,3-benzothiazol-6-ol. After neutralization, the precipitate was filtered off and washed with water. The crude solid was slurred in hot EtOAc/MeOH 95:5 and filtered. The filtrate was concentrated under reduced pressure and the residue was subjected to flash chromatography (EtOAc/MeOH 95:5) to give a product that was chromatographed once more (DCM/MeOH 95:5) to yield the title compound (65 mg). $^1$H NMR δ 9.74 (s, 1H) 8.53 (d, 1H) 7.93 (dd, 1H) 7.73 (d, 1H) 7.35 (d, 1H) 6.93 (dd, 1H) 6.61 (br s, 2H) 6.55 (d, 1H); MS m/z (M+H) 244.

Example 59

2-(6-Morpholin-4-ylpyridin-3-yl)-1,3-benzothiazole

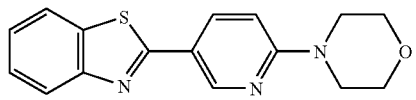

2-Bromo-1,3-benzothiazole (100 mg, 0.47 mmol) and 4-[5-(4,4,5,5-tetramethyl-1,3,2-dioxaborolan-2-yl)pyridin-2-yl]morpholine (163 mg, 0.56 mmol) were reacted according to the procedure used for the preparation of 5-(6-methoxy-1,3-benzothiazol-2-yl)pyrimidin-2-amine. Flash chromatography (Heptane/EtOAc 1:1) furnished the title compound (73 mg) as an off-white solid. $^1$H NMR δ 8.81 (d, 1H) 8.18 (dd, 1H) 8.10 (d, 1H) 7.98 (d, 1H) 7.54-7.48 (m, 1H) 7.44-7.38 (m, 1H) 7.00 (d, 1H) 3.74-3.70 (m, 4H) 3.65-3.60 (m, 4H); MS m/z (M+H) 298.

Example 60

6-Fluoro-2-(6-morpholin-4-ylpyridin-3-yl)-1,3-benzothiazole

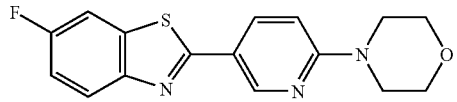

2-Bromo-6-fluoro-1,3-benzothiazole (100 mg, 0.43 mmol) and 4-[5-(4,4,5,5-tetramethyl-1,3,2-dioxaborolan-2-yl)pyridin-2-yl]morpholine (150 mg, 0.52 mmol) were reacted according to the procedure used for the preparation of 5-(6-methoxy-1,3-benzothiazol-2-yl)pyrimidin-2-amine. Flash chromatography (Heptane/EtOAc 1:1) furnished the title compound (126 mg) as an off-white solid. $^1$H NMR δ 8.79 (d, 1H) 8.15 (dd, 1H) 8.05-7.97 (m, 2H) 7.40-7.34 (m, 1H) 6.99 (d, 1H) 3.73-3.69 (m, 4H) 3.64-3.60 (m, 4H); MS m/z (M+H) 316.

Example 61

5-(6-Methoxy-1,3-benzothiazol-2-yl)pyridine-2-carboxamide

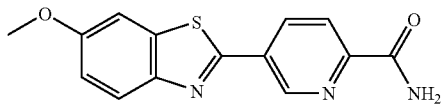

6-Methoxy-1,3-benzothiazole (0.100 g, 0.61 mmol) and 5-bromopyridine-2-carboxamide (0.146 g, 0.73 mmol) were reacted according to the procedure used for the preparation of 6-methoxy-2-[5-(trifluoromethyl)pyridin-2-yl]-1,3-benzothiazole, with the following exceptions: 10 mol % bis(tri-t-butylphosphine) palladium (0) was used and the amount of DMF was reduced (3 mL). The reaction mixture was concentrated and flash chromatography of the residue gave the title compound (10 mg) as an off-white solid. $^1$H NMR δ 9.25 (dd, 1H) 8.56 (dd, 1H) 8.23 (br s, 1H) 8.19 (dd, 1H) 8.04 (d, 1H) 7.81 (d, 1H) 7.78 (br s, 1H) 7.20 (dd, 1H) 3.88 (s, 3H); MS m/z (M+H) 286.

Example 62

2-(6-Morpholin-4-ylpyridin-3-yl)-1,3-benzothiazol-6-ol

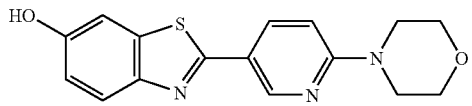

(a) 2-Bromo-1,3-benzothiazol-6-ol

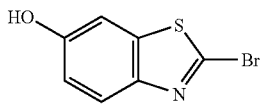

2-Bromo-6-methoxy-1,3-benzothiazole (0.832 g, 3.41 mmol) was subjected to the procedure used for the preparation of 2-[2-(dimethylamino)pyrimidin-5-yl]-1,3-benzothiazol-6-ol, with the following exceptions: 4.4 equiv BBr$_3$-solution was used, and after being stirred on, the mixture was poured into MeOH and then concentrated under reduced pressure. A slurry of this residue in EtOAc was filtered through silica and eluted with EtOAc/DCM/MeOH 10:10:1 and DCM/MeOH 9:1. The crude product was recrystallized from EtOAc to give 2-bromo-1,3-benzothiazol-6-ol (0.602 g). $^1$H NMR δ 10.00 (br s, 1H) 7.77 (d, 1H) 7.39 (d, 1H) 6.97 (dd, 1H).

(b) 2-(6-Morpholin-4-ylpyridin-3-yl)-1,3-benzothiazol-6-ol (title compound)

2-Bromo-1,3-benzothiazol-6-ol (40 mg, 0.17 mmol) and 4-[5-(4,4,5,5-tetramethyl-1,3,2-dioxaborolan-2-yl)pyridin-2-yl]morpholine (61 mg, 0.21 mmol) were reacted according to the procedure used for the preparation of 5-(6-methoxy-1,3-benzothiazol-2-yl)pyrimidin-2-amine. The reaction mixture was cooled to rt and concentrated. Flash chromatography (Heptane/EtOAc 1:1) gave the title compound (21 mg) as an off-white solid. $^1$H NMR δ 9.80 (br s, 1H) 8.71 (d, 1H) 8.09 (dd, 1H) 7.77 (d, 1H) 7.37 (d, 1H) 6.98-6.93 (m, 2H) 3.73-3.69 (m, 4H) 3.61-3.56 (m, 4H); MS m/z (M+H) 314.

Example 63

5-(6-Fluoro-1,3-benzothiazol-2-yl)-N-methylpyridin-2-amine

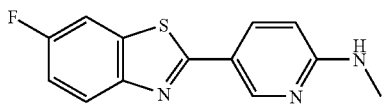

A mixture of 5-bromo-N-methylpyridin-2-amine (50 mg, 0.27 mmol), bis(pinacolato)diboron (75 mg, 0.30 mmol), Pd(dppf)Cl$_2$*DCM (6.5 mg, 0.008 mmol) and KOAc (79 mg, 0.80 mmol) in DMF (2 mL) was heated at 150° C. for 10 minutes in a microwave reactor. Then 2-bromo-6-fluoro-1,3-benzothiazole (93 mg, 0.40 mmol), another batch of Pd(dppf)Cl$_2$*DCM (6.5 mg, 0.008 mmol) and 2 M aq. K$_2$CO$_3$ (0.5 mL) were added and the reaction mixture was heated at 100° C. for 5 minutes in a microwave reactor. The mixture was allowed to cool and was partitioned between EtOAc and H$_2$O. The organic phase was washed with water and brine and was dried (Na$_2$SO$_4$). Concentration under vacuum and purification by HPLC gave the title compound (8 mg). $^1$H NMR (CHLOROFORM-d: CD$_3$OD) δ 8.61 (d, 1H) 8.02 (dd, 1H) 7.87 (dd, 1H) 7.57 (dd, 1H) 7.22-7.15 (m, 1H) 6.55 (d, 1H) 2.94 (s, 3H); MS m/z (M+H) 260, (M−H) 258.

Example 64

5-(1,3-Benzothiazol-2-yl)pyridine-2-carboxamide

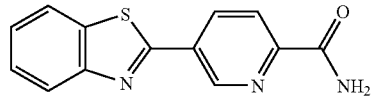

(a) 5-(Trimethylstannyl)pyridine-2-carboxamide

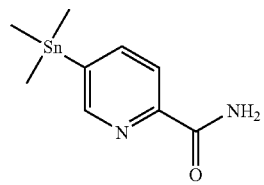

A mixture of 5-bromo-2-pyridinecarboxamide (0.100 g, 0.50 mmol), hexamethylditin (0.21 mL, 1.0 mmol) and tetrakis(triphenylphosphine)palladium (0) (57 mg, 0.05 mmol) in dioxane (2 mL) was heated in a microwave reactor at a power of 300 W for 10 min. The reaction mixture was filtered and concentrated under reduced pressure. Flash chromatography (Heptane/EtOAc gradient) gave 5-(trimethylstannyl)pyridine-2-carboxamide (98 mg) as a white solid. MS m/z (M+H) 287.

(b) 5-(1,3-Benzothiazol-2-yl)pyridine-2-carboxamide (title compound)

A mixture of 2-chloro-1,3-benzothiazole (38 μL, 0.31 mmol), 5-(trimethylstannyl)pyridine-2-carboxamide (97 mg, 0.34 mmol) and Pd(PPh$_3$)$_4$ (35 mg, 0.03 mmol) in dry dioxane (2 mL) was heated under argon to 160° C. for 30 min in a microwave reactor. The precipitate was filtered off. Flash chromatography (DCM/MeOH 99:1→DCM/Acetone 1:1) gave the title compound (23 mg) as a white solid. $^1$H NMR δ

9.31 (dd, 1H) 8.63 (dd, 1H) 8.27 (br s, 1H) 8.26-8.19 (m, 2H) 8.16 (d, 1H) 7.83 (br s, 1H) 7.64-7.59 (m, 1H) 7.57-7.52 (m, 1H); MS m/z (M+H) 256.

Example 65

5-(1,3-Benzothiazol-2-yl)-N-methylpyridin-2-amine

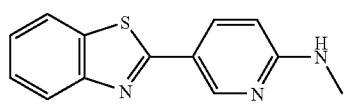

(a) tert-Butyl (5-bromopyridin-2-yl)methylcarbamate

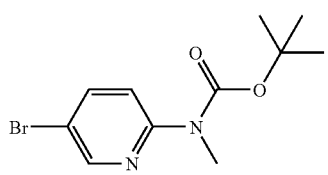

NaHMDS (88 mL, 1 M in THF) was added dropwise to 5-bromo-N-methylpyridin-2-amine (15.0 g, 80.2 mmol) and di-tert-butyl dicarbonate (21.0 g, 96.2 mmol) in THF (50 mL) at ° C. The reaction mixture was allowed to reach rt and was stirred for 3 h before it was concentrated under reduced pressure. The residue was partitioned between EtOAc and sat. aq. NaHCO$_3$. The layers were separated and the aqueous phase was extracted with EtOAc. The combined organic layers were dried (Na$_2$SO$_4$) and concentrated. Filtration through silica, eluting with Heptane/EtOAc 9:1, gave tert-butyl (5-bromopyridin-2-yl)methylcarbamate (22.7 g) as a pale yellow oil. $^1$H NMR δ 8.48 (d, 1H) 7.96 (dd, 1H) 7.64 (d, 1H) 3.27 (s, 3H) 1.46 (s, 9H).

(b) tert-Butyl[5-(5,5-dimethyl-1,3,2-dioxaborinan-2-yl)pyridin-2-yl]methylcarbamate

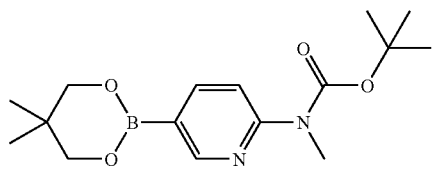

n-BuLi (27 mL, 2.5 M) was slowly added to a stirred solution of tert-butyl (5-bromopyridin-2-yl)methylcarbamate (17.7 g, 61.6 mmol) in THF (280 mL) at −78° C. under an argon atmosphere. After 5 min at −78° C., triisopropylborate (28.5 mL, 123 mmol) was added and the mixture was stirred at −78° C. for 1 h. Neopentyl glycol (6.4 g, 61.4 mmol) was added and the reaction mixture was allowed to reach rt and was stirred for 2.5 d. The reaction was quenched with water (300 mL). The phases were separated and the aqueous phase was extracted with DCM. The organic layer was concentrated and the residue was purified by two successive flash chromatographies (Heptane/EtOAc 9:1→1:4 and DCM/MeOH 24:1 respectively) to give the product (2.23 g) as a white solid.

$^1$H NMR δ 8.57 (dd, 1H) 7.94 (dd, 1H) 7.65 (dd, 1H) 3.76 (s, 4H) 3.30 (s, 3H) 1.47 (s, 9H) 0.96 (s, 6H).

(c) tert-Butyl[5-(1,3-benzothiazol-2-yl)pyridin-2-yl]methylcarbamate

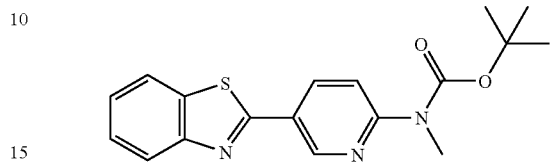

2-Chlorobenzothiazole (31 μL, 0.25 mmol) and tert-butyl [5-(5,5-dimethyl-1,3,2-dioxaborinan-2-yl)pyridin-2-yl]methylcarbamate (80 mg, 0.25 mmol) were reacted according to the procedure used for the preparation of 5-(6-methoxy-1,3-benzothiazol-2-yl)pyrimidin-2-amine. After 1 h at 80° C., the mixture was concentrated under reduced pressure and the residue was partitioned between DCM and H$_2$O. The organic phase was concentrated. Flash chromatography (Heptane/EtOAc gradient) gave the product (53 mg) as a white solid. MS m/z (M+H) 342.

(d) 5-(1,3-Benzothiazol-2-yl)-N-methylpyridin-2-amine (title compound)

tert-Butyl[5-(1,3-benzothiazol-2-yl)pyridin-2-yl]methylcarbamate (40 mg, 0.12 mmol) was dissolved in DCM (5 mL). TFA (0.5 mL) was added and the reaction mixture was stirred at rt for 4 h. The mixture was concentrated and the residue was partitioned between EtOAc and sat. aq. NaHCO$_3$. The organic phase was washed with brine, dried (Na$_2$SO$_4$) and concentrated under reduced pressure. Purification by HPLC gave the title compound (18 mg) as a white solid. $^1$H NMR δ 8.70 (d, 1H) 8.06 (m, 1H) 8.02 (dd, 1H) 7.94 (dd, 1H) 7.46-7.51 (m, 1H) 7.40-7.35 (m, 1H) 7.29 (br q, 1H) 6.59 (d, 1H) 2.86 (d, 3H); MS m/z (M+H) 242, (M−H) 240.

Example 66

2-(6-Ethoxypyridin-3-yl)-1,3-benzothiazol-6-ol

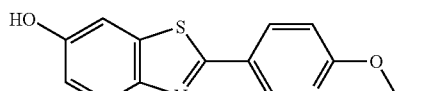

2-(6-Ethoxypyridin-3-yl)-6-methoxy-1,3-benzothiazole (23 mg, 80 μmol) was reacted according to the procedure used for the preparation of 2-[2-(dimethylamino)pyrimidin-5-yl]-1,3-benzothiazol-6-ol, with the following exceptions: The reaction mixture was allowed to reach rt on. sat. aq. NaHCO$_3$ was added and the mixture was extracted with EtOAc. The organic phase was dried and concentrated under reduced pressure. Preparative HPLC of the residue gave the title compound (4 mg). $^1$H NMR (CHLOROFORM-d: CD$_3$OD) δ 8.69

(d, 1H) 8.20 (dd, 1H) 7.79 (d, 1H) 7.29 (d, 1H) 6.99 (dd, 1H) 6.86 (d, 1H) 4.39 (q, 2H) 1.41 (t, 3H); MS m/z (M+H) 273.

Example 67

2-(6-Bromopyridin-3-yl)-6-methoxy-1,3-benzothiazole

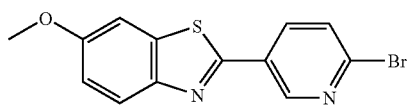

2-Bromo-6-methoxy-1,3-benzothiazole (49 mg, 0.20 mmol) and 2-bromo-5-(4,4,5,5-tetramethyl-1,3,2-dioxaborolan-2-yl)pyridine (68 mg, 0.24 mmol) were reacted according to the procedure used for the preparation of 5-(6-methoxy-1,3-benzothiazol-2-yl)pyrimidin-2-amine, with the following exceptions: The reaction was stirred for 2 h and was then allowed to reach rt on. The mixture was filtered through a plug of silica and $Na_2SO_4$, eluting with DCM. The volume of the filtrate was reduced in a centrifuge and the remainder was purified by HPLC to give the title compound (4.2 mg). $^1$H NMR (CHLOROFORM-d: $CD_3OD$) δ 8.93 (d, 1H) 8.21 (dd, 1H) 7.92 (d, 1H) 7.68 (d, 1H) 7.43 (d, 1H) 7.12 (dd, 1H) 3.89 (s, 3H).

Example 68

2-(5-Fluoro-6-methoxy-pyridin-3-yl)-6-methoxybenzothiazole

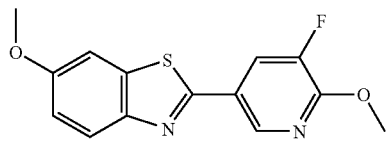

2-Bromo-6-methoxy-1,3-benzothiazole (49 mg, 0.20 mmol) and (5-chloro-6-methoxypyridin-3-yl)boronic acid (45 mg, 0.24 mmol) were reacted according to the procedure used for the preparation of 2-(6-bromopyridin-3-yl)-6-methoxy-1,3-benzothiazole to give the title compound (0.2 mg). $^1$H NMR (CHLOROFORM-d: $CD_3OD$) δ 8.51 (d, 1H) 8.03 (dd, 1H) 7.87 (d, 1H) 7.43 (d, 1H) 7.10 (dd, 1H) 4.08 (s, 3H) 3.88 (s, 3H); MS m/z (M+H) 291.

Example 69

5-[1,3]Dioxolo[4,5-f][1,3]benzothiazol-6-yl-N-methylpyridin-2-amine

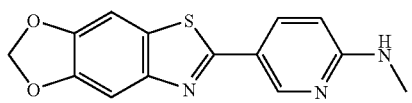

To [1,3]Dioxolo[4,5-f][1,3]benzothiazole (98 mg, 0.55 mmol) and 5-bromo-N-methylpyridin-2-amine (112 mg, 0.60 mmol) were subjected to the procedure used for the preparation of 2-(2-methoxypyrimidin-5-yl)-1,3-benzothiazole, with the following exceptions: 5 mol % bis(tri-t-butylphosphine) palladium (0) was used and the reaction was heated under argon at 170° C. in a microwave oven for 30 min. The crude material was purified by flash chromatography (Heptane/EtOAc 1:1) to give the title compound (56 mg) as a yellow solid. $^1$H NMR δ 8.62 (d, 1H) 7.94 (dd, 1H) 7.61 (s, 1H) 7.47 (s, 1H) 7.19 (q, 1H) 6.57 (d, 1H) 6.13 (s, 2H) 2.85 (d, 3H); MS m/z (M+H) 286.

Example 70

6-Methoxy-2-[5-(methylthio)pyridin-2-yl]-1,3-benzothiazole

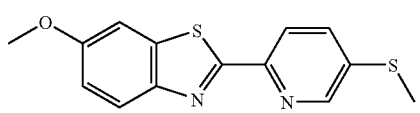

6-Methoxy-1,3-benzothiazole (35 mg, 0.21 mmol) and 2-bromo-5-(methylthio)pyridine (1.1 equiv) were reacted according to the procedure used for the preparation of 6-methoxy-2-[5-(trifluoromethyl)pyridin-2-yl]-1,3-benzothiazole. This gave the title compound (1 mg) as a pale yellow solid. $^1$H NMR (CHLOROFORM-d) δ 8.52 (d, 1H) 8.22 (d, 1H) 7.95 (d, 1H) 7.67 (dd, 1H) 7.40 (d, 1H) 7.11 (dd, 1H) 3.92 (s, 3H) 2.58 (s, 3H); MS m/z (M+H) 289.

Example 71

6-Methoxy-2-(6-pyrrolidin-1-ylpyridin-3-yl)-1,3-benzothiazole

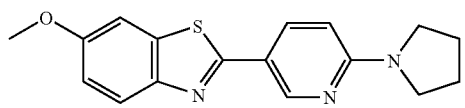

In a microwave vial were added 2-(6-fluoropyridin-3-yl)-6-methoxy-1,3-benzothiazole (75 mg, 0.29 mmol), water (2.5 mL) and pyrrolidine (0.50 mL) and the reaction was heated in a microwave oven at 100° C. for 5 min. The precipitated product was filtered off, washed with water and methanol and dried in a desicator over $P_2O_5$ to give the title compound (76 mg) as a white solid. $^1$H NMR (CHLOROFORM-d) δ 8.77 (d, 1H) 8.13 (dd, 1H) 7.87 (d, 1H) 7.33 (d, 1H) 7.05 (dd, 1H) 6.44 (d, 1H) 3.89 (s, 3H) 3.63-3.46 (m, 4H) 2.11-1.98 (m, 4H); MS m/z (M+H) 312.

Example 72

2-(6-Methylaminopyridin-3-yl)benzothiazole-6-carboxamide

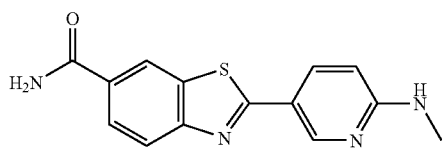

a) 2-Chloro-1,3-benzothiazole-6-carboxamide

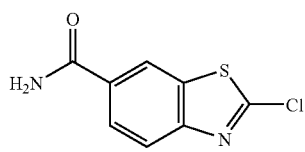

2-Bromo-1,3-benzothiazole-6-carboxylic acid (100 mg, 0.39 mmol) and thionyl chloride (2 mL) were mixed and stirred at rt for 1 h then at 60° C. for 30 min. The mixture was concentrated under reduced pressure and the residue was dissolved in CHCl$_3$ (3 mL). This solution was added dropwise to NH$_3$ (ca. 7 N in MeOH, 5 mL) at 0° C. The mixture was stirred at rt for 1 h before it was concentrated under reduced pressure. The crude product was partitioned between EtOAc and H$_2$O. The aqueous layer was extracted with EtOAc and the organic phase was dried (Na$_2$SO$_4$) and concentrated to give the product (77 mg) as a white solid. MS m/z (M+H) 213, (M−H) 211.

b) tert-Butyl[5-(6-carbamoyl-1,3-benzothiazol-2-yl)pyridin-2-yl]methylcarbamate

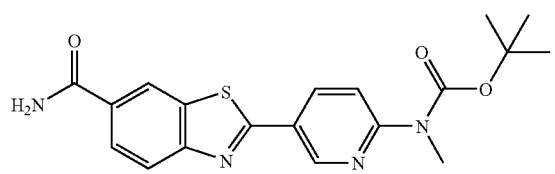

A mixture of 2-chloro-1,3-benzothiazole-6-carboxamide (77 mg, 0.36 mmol), tert-butyl[5-(5,5-dimethyl-1,3,2-dioxaborinan-2-yl)pyridin-2-yl]methylcarbamate (0.174 g, 0.54 mmol), Pd(dppf)Cl$_2$*DCM (30 mg, 0.036 mmol) and 2 M aq. K$_2$CO$_3$ (0.8 mL) in DMF (2 mL) was stirred under argon at 80° C. for 2 h. The reaction mixture was filtered and the filtrate was partitioned between EtOAc and H$_2$O. The layers were separated and the aqueous phase was extracted with EtOAc. The combined organic phases were dried (MgSO$_4$) and concentrated. Flash chromatography (Heptane/EtOAc gradient) gave the product (66 mg) as a white solid. MS m/z (M−H) 383.

c) 2-(6-Methylaminopyridin-3-yl)benzothiazole-6-carboxamide (title compound)

To a stirred slurry of tert-butyl[5-(6-carbamoyl-1,3-benzothiazol-2-yl)pyridin-2-yl]methylcarbamate (10 mg, 0.026 mmol) in DCM (1 mL) was added TFA (1 mL) dropwise at 0° C., and the reaction mixture was stirred at rt on. The solvent was evaporated under reduced pressure. Preparative HPLC of the residue gave the title compound (6 mg) as a white solid. $^1$H NMR δ 8.74 (d, 1H) 8.56 (s, 1H) 8.11-7.94 (m, 4H) 7.50-7.36 (m, 2H) 6.60 (d, 1H) 2.87 (d, 3H); MS m/z (M+H) 285.

Example 73

2-(6-Methylaminopyridin-3-yl)benzothiazol-6-amine

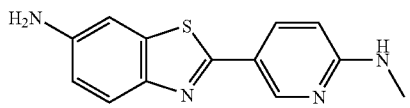

a) tert-Butyl (2-bromo-1,3-benzothiazol-6-yl)carbamate

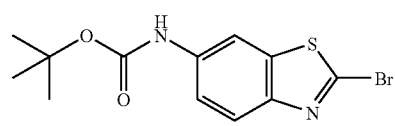

Triethylamine (1.94 mL, 13.9 mmol) and diphenylphosphoryl azide (2.76 mL, 12.8 mmol) were added to a solution of 2-bromo-1,3-benzothiazole-6-carboxylic acid (3.0 g, 11.6 mmol) in tert-butanol (100 mL) and the reaction mixture was stirred at 80° C. for 4 h. The solvent was evaporated under reduced pressure and the residue was subjected to flash chromatography (Heptane/EtOAc gradient) to give tert-butyl (2-bromo-1,3-benzothiazol-6-yl)carbamate (1.1 g) as a white solid. MS m/z (M+H) 329, 331.

b) tert-butyl (5-{6-[(tert-butoxycarbonyl)amino]-1,3-benzothiazol-2-yl}pyridin-2-yl)methylcarbamate

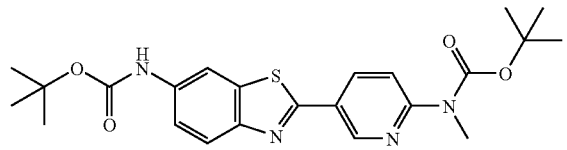

tert-Butyl (2-bromo-1,3-benzothiazol-6-yl)carbamate (100 mg, 0.30 mmol) and tert-butyl [5-(5,5-dimethyl-1,3,2-dioxaborinan-2-yl)pyridin-2-yl]methylcarbamate (0.146 g, 0.46 mmol) were subjected to the procedure used for the preparation of tert-butyl[5-(6-carbamoyl-1,3-benzothiazol-2-yl)pyridin-2-yl]methylcarbamate. This gave the product (110 mg) as a white solid. MS m/z (M−H) 455.

c) 2-(6-Methylaminopyridin-3-yl)benzothiazol-6-amine (title compound)

TFA (1.5 mL) was added to a solution of tert-butyl (5-{6-[(tert-butoxycarbonyl)amino]-1,3-benzothiazol-2-yl}pyridin-2-yl)methylcarbamate (40 mg, 0.088 mmol) in DCM (1.5 mL) at 0° C. and the reaction mixture was stirred at rt on. The solvent was evaporated under reduced pressure. Preparative HPLC of the residue gave the title compound (12 mg) as a white solid. ¹H NMR δ 8.55 (d, 1H) 7.90 (dd, 1H) 7.59 (d, 1H) 7.12 (br q, 1H) 7.05 (s, 1H) 6.74 (dd, 1H) 6.55 (d, 1H) 5.37 (br s, 2H) 2.83 (d, 3H); MS m/z (M+H) 257, (M−H) 255.

Example 74

N-Methyl-2-(6-methylaminopyridin-3-yl)benzothiazol-6-amine

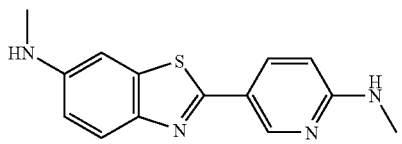

(a) tert-Butyl (5-{6-[(tert-butoxycarbonyl)(methyl)amino]-1,3-benzothiazol-2-yl}pyridin-2-yl)methylcarbamate

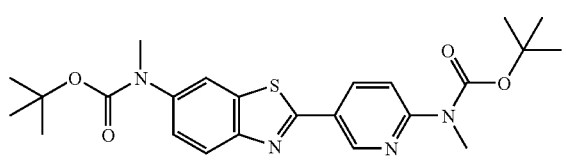

NaH (95%, 4.5 mg, 0.18 mmol) was added to a solution of tert-butyl (5-{6-[(tert-butoxycarbonyl)amino]-1,3-benzothiazol-2-yl}pyridin-2-yl)methylcarbamate (66 mg, 0.14 mmol) in DMF (2 mL). The mixture was cooled to 0° C. and MeI (10 μL, 0.16 mmol) was added. The reaction was stirred at rt on. Water was added and the mixture was extracted with EtOAc (3×) The combined organic phases were dried (MgSO₄) and concentrated. Flash chromatography (Heptane/EtOAc gradient) gave the product (60 mg) as a white solid. MS m/z (M+H) 471.

(b) N-Methyl-2-(6-methylaminopyridin-3-yl)benzothiazol-6-amine (title compound)

tert-Butyl (5-{6-[(tert-butoxycarbonyl)(methyl)amino]-1,3-benzothiazol-2-yl}pyridin-2-yl)methylcarbamate (53 mg, 0.11 mmol) was reacted according to the procedure used for the preparation of 2-(6-methylaminopyridin-3-yl)benzothiazol-6-amine. This gave the title compound (20 mg) as a yellow solid. ¹H NMR δ 8.56 (d, 1H) 7.91 (dd, 1H) 7.63 (d, 1H) 7.12 (br q, 1H) 7.00 (d, 1H) 6.75 (dd, 1H) 6.55 (d, 1H) 5.99 (br q, 1H) 2.84 (d, 3H) 2.73 (d, 3H); MS m/z (M+H) 271.

PRECURSOR EXAMPLES

Below follows a number of non-limiting examples of compounds of the invention. The below exemplified compounds are useful as precursors for the preparation of [¹¹C]methyl labeled compounds of the invention. The general methods used for the preparation of these precursors were the same as those used for the preparation of the compound examples herein.

Precursor Example 1

5-(6-{[tert-Butyl(dimethyl)silyl]oxy}-1,3-benzothiazol-2-yl)pyridin-2-amine

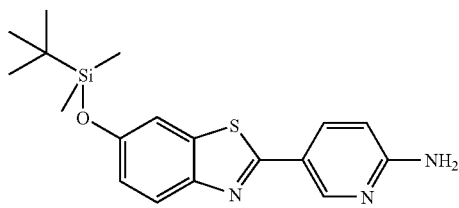

a) 6-{[tert-Butyl(dimethyl)silyl]oxy}-1,3-benzothiazol-2-anine

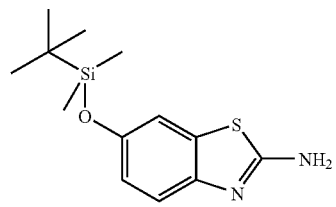

A solution of 2-amino-6-hydroxybenzothiazole (5.00 g, 30.1 mmol), TBDMSCl (5.40 g, 1.2 equiv) and imidazole (2.46 g, 1.2 equiv) in DMF (160 ml) was stirred at ambient temperature for 16 h. The reaction mixture was then partitioned between water and ethyl acetate. The aqueous phase was extracted twice with ethyl acetate and the combined organics dried (MgSO₄) and concentrated in vacuo. The crude product thus obtained was purified by silica gel chromatography by gradient elution (Q-heptane:ethyl acetate) to yield 3.0 g of the title compound as a yellowish solid. ¹H NMR δ 7.23 (br s, 2H) 7.18 (d, 1H) 7.16 (d, 1H) 6.70 (dd, 1H) 0.95 (s, 9H) 0.16 (s, 6H); MS m/z (M+H) 281.

(b) 2-Bromo-6-{[tert-butyl(dimethyl)silyl]oxy}-1,3-benzothiazole

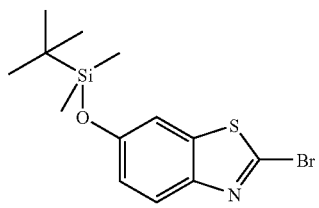

To a cool (0° C.) suspension of 6-{[tert-butyl(dimethyl)silyl]oxy}-1,3-benzothiazol-2-amine (2.00 g, 7.13 mmol) and copper(II) bromide (2.40 g, 1.5 equiv) in acetonitrile (70 ml), was added tert-butyl nitrite (1.27 ml, 1.5 equiv) in one portion. The reaction mixture was then allowed to come to ambient temperature and stirred for another 5 h before partitioning between water and ethyl acetate. The aqueous phase was extracted twice with ethyl acetate and the combined organics were washed successively with water and brine before drying (MgSO$_4$) and concentration in vacuo. The obtained crude product thus obtained was purified by silica gel chromatography by gradient elution (n-heptane:ethyl acetate) to yield 1.95 g of the title compound as a red oil. $^1$H NMR δ 7.85 (d, 1H) 7.62 (d, 1H) 7.03 (dd, 1H) 0.96 (s, 9H) 0.22 (s, 6H); MS m/z (M+H) 344, 346.

(c) 2-(6-Aminopyridin-3-yl)-1,3-benzothiazol-6-ol

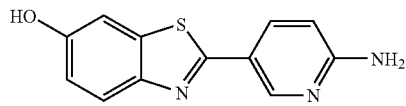

A mixture of 2-bromo-6-{[tert-butyl(dimethyl)silyl]oxy}-1,3-benzothiazole (500 mg, 1.45 mmol), 5-(4,4,5,5-tetramethyl-1,3,2-dioxaborolan-2-yl)pyridin-2-amine (383 mg, 1.2 equiv), aqueous potassium carbonate (2.0 M, 2.9 ml, 4.0 equiv) and Pd(dppf)Cl$_2$ (119 mg, 0.10 equiv) in DMF (6.0 ml) was stirred at 80° C. under argon for 2 h. The mixture was then added to DCM (100 ml), dried (Na$_2$SO$_4$) and concentrated in vacuo. The crude thus obtained was purified by silica gel chromatography by gradient elution (n-heptane:ethyl acetate) to yield 237 mg of the title compound. $^1$H NMR δ 9.74 (s, 1H) 8.53 (d, 1H) 7.94 (dd, 1H) 7.73 (d, 1H) 7.35 (d, 1H) 6.93 (dd, 1H) 6.61 (s, 2H) 6.55 (d, 1H); MS m/z (M+H) 244.

(d) 5-(6-{[tert-Butyl(dimethyl)silyl]oxy}-1,3-benzothiazol-2-yl)pyridin-2-amine (title compound)

A solution of 2-(6-aminopyridin-3-yl)-1,3-benzothiazol-6-ol (177 mg, 0.73 mmol), TBDMSCl (121 mg, 1.1 equiv) and imidazole (124 mg, 2.5 equiv) in DMF (2.0 ml) was stirred at ambient temperature for 2 h. The reaction mixture was then partitioned between water and ethyl acetate. The aqueous phase was extracted twice with ethyl acetate and the combined organics dried (MgSO$_4$) and concentrated in vacuo. The crude product thus obtained was purified by silica gel chromatography, using a mixture of DCM and methanol (95:5) as eluent, to yield 200 mg of the title compound as a white solid. $^1$H NMR δ 8.56 (d, 1H) 7.96 (dd, 1H) 7.80 (d, 1H) 7.54 (d, 1H) 6.98 (dd, 1H) 6.67 (s, 2H) 6.56 (d, 1H) 0.97 (s, 9H) 0.22 (s, 6H); MS m/z (M+H) 358.

Precursor Example 2

5-[6-(Ethoxymethoxy)-1,3-benzothiazol-2-yl]pyridin-2-amine

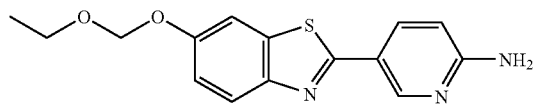

Chloromethyl ethyl ether (0.24 mL) was added in one portion to a rapidly stirred solution of 2-(6-aminopyridin-3-yl)-1,3-benzothiazol-6-ol (0.319 g, 1.31 mmol) and K$_2$CO$_3$ (0.543 g) in DMF (10 mL) at 0° C. The reaction was stirred at rt on. The mixture was concentrated under reduced pressure and the residue was subjected to flash chromatography (DCM/MeOH 99:1→95:5) to yield the title compound (31 mg). $^1$H NMR δ 8.57 (d, 1H) 7.97 (dd, 1H) 7.84 (d, 1H) 7.71 (d, 1H) 7.16 (dd, 1H) 6.66 (br s, 2H) 6.56 (d, 1H) 5.30 (s, 2H) 3.69 (q, 2H) 1.15 (t, 3H); MS m/z (M+H) 302, (M−H) 300.

$^{11}$C-LABELED COMPOUND EXAMPLES

Below follows non-limiting example(s) of compounds of the invention. The corresponding non-labeled analogs display an IC$_{50}$ of less than 20 μM in the competition binding assay described herein.

$^{11}$C-Example 1

[N-Methyl-$^{11}$C]-2-(6-Methylamino-pyridin-3-yl)-benzothiazol-6-ol

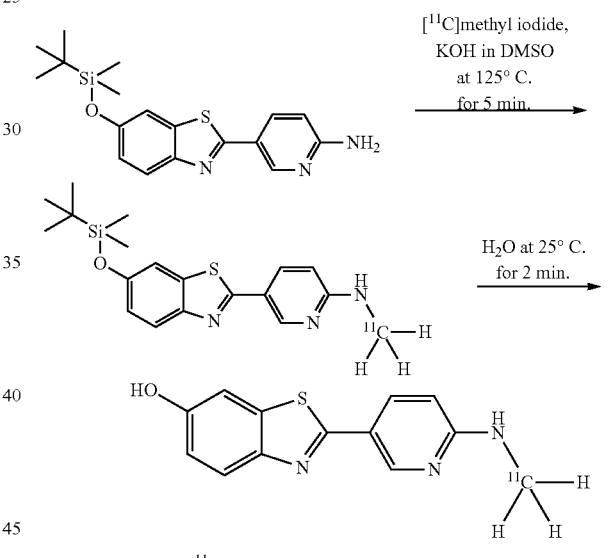

[N-Methyl-$^{11}$C]-2-(6-Methylamino-pyridin-3-yl)-benzothiazol-6-ol

Unlabeled 2-[6-(methylamino)pyridin-3-yl]-1,3-benzothiazol-6-ol, prepared as described herein, was used as analytical reference and standard. Other chemicals and reagents used were obtained from commercial sources and were of analytical grade. [$^{11}$C]methane was obtained via the $^{14}$N(p,α)$^{11}$C reaction on nitrogen with 10% hydrogen, with 18 MeV protons using a GEMS PET trace cyclotron. The [$^{11}$C]methane was passed through a heated column containing I$_2$ to produce [$^{11}$C]methyl iodide (Larsen et al. Appl. Radiat. Isot. 1997, 48, 153 and Sandell et al J. Labelled Compd Radiopharm. 2000, 43, 331). The generated [$^{11}$C]MeI was trapped at rt in a vessel containing 5-(6-{[tert-butyl(dimethyl)silyl]oxy}-1,3-benzothiazol-2-yl)pyridin-2-amine (2.5 mg), DMSO (300 μl) and KOH (10 mg). The reaction mixture was then heated at 125° C. for 5 min., followed by removal of the TBDMS-group by treatment with water (200 μl) at rt for 2 min. The crude material thus obtained was purified by reversed phase HPLC, using a Waters μ-Bondapak C-18 column (300×7.8 mm, 10 mm) equipped with a UV-detector (λ=254 nm) and GM tube for radiation detection, employing CH$_3$CN—aq. HCO$_2$NH$_4$ (0.1M) 30:70 v/v as the mobile phase at a flowrate of 6 ml/min. Analysis of the obtained title compound revealed an incorporation yield of [$^{11}$C]MeI of about 50%, a radiochemical purity of >99%, and a specific radioactivity of 3861 Ci/mmol.

BIOLOGICAL EXAMPLES

[N-Methyl-3H$_3$]-2-(6-Methylamino-pyridin-3-yl)-benzothiazol-6-ol (Example 32) and [N-methyl-$^{11}$C]-2-(6-methylamino-pyridin-3-yl)-benzothiazol-6-ol ($^{11}$C-Example 1), both compounds of the present invention, are referred to below either by these names or by "[$^3$H]AZAD" and "[$^{11}$C] AZAD", respectively. The following compounds were used as comparative compounds and are referred to in the text below by their indicated corresponding names.

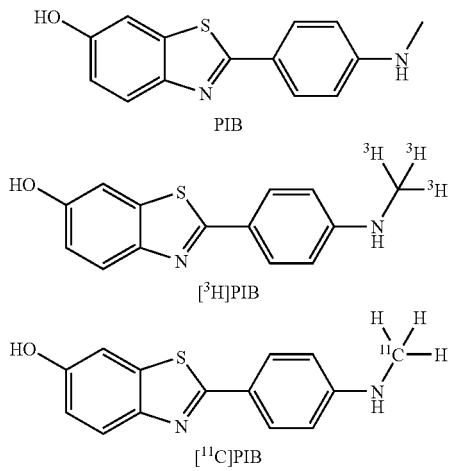

Compounds of the present invention were tested in one or several of the following assays/experiments/studies:
Competition Binding Assay Competition binding was performed in 384-well FB filter plates using synthetic Aβ 1-40 in 2.7 nM of [$^3$H]PIB (or another $^3$H-labeled radioligand when so mentioned) in phosphate buffer at pH 7.5, by adding various concentrations of non-radioactive compounds originally dissolved in DMSO. The binding mixture was incubated for 30 min at room temperature, followed by vacuum filtration, and subsequentially by washing twice with 1% Triton-X100. Scintillation fluid was thereafter added to the collected Aβ 1-40 on the filter plate, and the activity of the bound remaining radioligand ([$^3$H]PIB or another $^3$H-labeled radioligand) was measured using 1450 Microbeta from PerkinElmer.
Dissociation Experiments Dissociation experiments were performed in 96-well polypropylene deep well plates. 2 μM human synthetic Aβ 1-40 fibrils in phosphate buffer pH 7.5, or buffer alone as control, was incubated with 9 nM of a $^3$H-labeled radioligand of the present invention for 4 h at room temperature. Dissociation was started at different time points, by the addition of an equal volume of a non-labeled compound of the present invention, or a reference compound (10 μM), in 4% DMSO in phosphate buffer at pH 7.5. The radioactivity still bound to the Aβ 1-40 fibrils at the end of the incubation was detected on FB filters after filtration in a Brandel apparatus using a wash buffer containing 0.1% Triton-X100.

In Vivo Rat Brain Entry Studies

Brain exposure after i.v administration was determined in rat brains using cassette dosing. Four different compounds were dosed followed by plasma and brain sampling at 2 and 30 minutes after the dosing. 2 to 30 min brain concentration ratios, and percentage of total of injected dose after 2 mins found in brain, were calculated. The compound concentrations were determined by analysis of protein precipitated plasma samples by reversed-phase liquid chromatography coupled to a electrospray tandem mass spectrometer.
Binding to Amyloid Plagues in Post-Mortem Human AD Brains and Transgenic Mice Brains Slide-mounted brain sections (10 μm) from APP/PS1 transgenic mice were collected at the level of the lateral septum (bregma+0.98 mm; see Paxinos and Franklin, 2001). Human cortical sections (7 μm) from two AD patients and 1 control subject were obtained from a Dutch tissue bank.

Sections were preincubated for 30 minutes at room temperature in 50 mM Tris HCl (pH 7.4) in the presence or absence of 1 μM PIB. Sections were transferred to buffer containing tritium-labeled compound (1 nM) with or without PIB (1 μM) and incubated for 30 minutes at room temperature. Incubation was terminated by 3 consecutive 10 minute rinses in buffer (1° C.) followed by a rapid rinse in distilled water (1° C.). Sections were air dried in front of a fan. Dried sections and plastic tritium standards (Amersham microscales-3H) were apposed to phosphoimage plates (Fuji) in a cassette and exposed overnight. The following morning, the image plates were processed with a Fuji phosphoimager (BAS 2500) using BAS Reader software. The resulting image was converted to TIF format using Aida software, optimized with Adobe Photoshop (v 8.0) and quantified using Image-J (NIH). Data were statistically analyzed using Excel.
Binding in APP/PS1 Mouse Brain After Compound Administration In-Vivo Naïve, awake mice were restrained and intravenously infused via the tail vein with either a tritium labeled compound of the present invention, or a tritium labeled reference compound via the tail vein. In one type of experiment, the animals were rapidly anesthetized with isofluorane and decapitated twenty minutes after compound administration (1 mCi). In another type of experiment, mice were given 1 mCi of a compound and were anesthetized and decapitated at a timepoint of 20, 40 or 80 minutes after administration. Brains were removed and frozen with powdered dry ice. Brains were sectioned (10 μm) in the coronal plane at the level of the striatum with a cryostat, thaw-mounted onto superfrost microscope slides and air-dried.

Methods designed to optimize the imaging of bound ligand after in vivo administration were thereafter employed. To selectively reduce unbound radioactivity levels, one-half of the sections were rinsed (3×10 minutes) in cold (1° C.) Tris buffer (50 mM, pH7.4) followed by a rapid rinse in cold (1° C.) deionized water. Sections were then air dried in front of a fan. Rinsed as well as unrinsed sections and tritium standards were exposed to phosphoimage plates (Fuji). Phosphoimage plates were processed with a Fujifilm BAS-2500 phosphoimager using BAS Reader software.
PET Studies in Non-Human Primates The monkey PET study aimed to assess and compare a [$^{11}$C]-labelled compound of this invention to [$^{11}$C]PIB regarding measures of brain availability, non-specific binding in the brain, whole body biodistribution, elimination and exploration of regional differences in uptake. Five brain PET measurements were performed in three monkeys under anesthesia. In each PET-measurement a sterile physiological phosphate buffer (pH=7.4) solution containing 52-55 MBq of either a [$^{11}$C]-labelled compound of this invention, or [$^{11}$C] PIB, was injected as a bolus into a sural vein over a period of 5 seconds with simultaneous start of PET-data acquisition. Radioactivity in brain was measured continuously for 93 minutes. Only [$^{11}$C]PIB measurement was performed in the first monkey. In the other two monkeys a [$^{11}$C]-labelled compound of the present invention was measured first and [$^{11}$C] PIB was administered in a subsequent measurement. The time between radioligand injections was approx. 2 h. PET measurements were evaluated with respect to the time-activity curve for the whole brain expressed as percent injected radioactivity dose.

Whole body PET-measurement was performed in one monkey. A sterile physiological phosphate buffer pH=7.4) solution containing 51 MBq of [$^{11}$C]PIB in the first measurement, and 57 MBq of a [$^{11}$C]-labelled compound of the present invention in the second measurement, was injected as a bolus into a sural vein over a period of 5 seconds with simultaneous start of PET-data acquisition that lasted for 87 min. The time between radioligand injections was 2 h. PET measurements were assessed visually by creating planar maximum intensity projection images of decay uncorrected data and also converting decay corrected images to ones containing parts-per-million (ppm) values of the total injected radioactivity.

Biological Example 1

Characterization of Specific Binding of Novel Heteroaryl Substituted Benzothiazole Derivatives to Aβ Amyloid Fibrils In Vitro Specific binding was determined according to the competition binding assay described herein. The determined IC$_{50}$'s in the completion binding assays (using [$^{3}$H]PIB as radioligand) of 5 compounds of the present invention are shown in Table 1. Results (activity of remaining [$^{3}$H]PIB versus increasing concentration of non-labeled compounds) from typical completion assay experiments are exemplified in FIG. 1. In a similar way, competition studies with $^{3}$H-labeled heteroaryl substituted benzthiazole derivates of the present invention were also conducted. Such results, from a typical competition study, are examplified in FIG. 2. PIB and 2-[6-(methylamino)pyridin-3-yl]-1,3-benzothiazol-6-ol (a novel compound of the present invention) both displaced [N-methyl-3H$_{3}$]-2-(6-methylamino-pyridin-3-yl)-benzothiazol-6-ol (a $^{3}$H-labeled compound of the present invention). The binding of [N-methyl-3H$_{3}$]-2-(6-methylamino-pyridin-3-yl)-benzothiazol-6-ol (example 32) to Aβ1-40 fibrils, was reversible as evident from the dissociation experiment exemplified in FIG. 3.

TABLE 1

IC$_{50}$'s obtained of 5 exemplified compounds of the present invention when run in the competion binding assay.

| NAME | EXAMPLE | IC50 (nM) |
|---|---|---|
| 5-(6-Methoxy-1,3-benzothiazol-2-yl)-N-methylpyridin-2-amine | 25 | 58 |
| 2-[6-(Methylamino)pyridin-3-yl]-1,3-benzothiazol-6-ol | 27 | 58 |
| 2-(6-Methoxypyridin-3-yl)-1,3-benzothiazole-6-carboxamide | 9 | 170 |
| 2-[6-(4-Methylpiperazin-1-yl)pyridin-3-yl]-1,3-benzothiazol-6-ol Acetate | 6 | 176 |
| N-{2-[6-(4-Methylpiperazin-1-yl)pyridin-3-yl]-1,3-benzothiazol-6-yl}acetamide | 15 | 186 |

Biological Example 2

In Vivo Rat Brain Entry Study

With reference to FIG. 4, it can be seen that 2-[6-(methylamino)pyridin-3-yl]-1,3-benzothiazol-6-ol (example 27), a compound of the present invention, enters the rat brain quickly with an uptake value of 1% of the injected dose at the 2 min time point, and clears rapidly from rat brain tissue with a 2 minute to 30 minute brain concentration ratio of >15. The results from the corresponding experiment, run under the same settings but with PIB instead of 2-[6-(methylamino)pyridin-3-yl]-1,3-benzothiazol-6-ol, is included for comparison (FIG. 4).

Biological Example 3

Binding to Amyloid Plaques in Post-Mortem Human AD Brains and Transgenic Mice

Postmortem brain tissue sections from AD brain and aged APP/PS1 transgenic mice were stained with [N-methyl-$^{3}$H$_{3}$]-2-(6-methylamino-pyridin-3-yl)-benzothiazol-6-ol (example 32). The APP/PS1 mouse is a double transgenic model combining two human gene mutations known to cause AD. In APP/PS1 mouse brain sections and in human cortical sections, [N-methyl-3H$_{3}$]-2-(6-methylamino-pyridin-3-yl)-benzothiazol-6-ol and [$^{3}$H]PIB labeled dense core plaques. In both tissues, binding was attenuated by 1 μM PIB. In superficial gray matter regions of human cortical sections, dense core plaque labeling in gray matter was visible against a background of diffuse labeling. The diffuse labeling was confined to gray matter regions whereas dense core plaque labeling could be seen outside of the superficial gray regions.

[N-Methyl-$^{3}$H$_{3}$]-2-(6-methylamino-pyridin-3-yl)-benzothiazol-6-ol and [$^{3}$H]PIB labeling were quantified in gray and white matter regions of human cortical sections. Specific binding was determined by subtracting binding in tissues co-exposed to 1 μM PIB. Analysis of these data showed that specific [N-methyl-$^{3}$H$_{3}$]-2-(6-methylamino-pyridin-3-yl)-benzothiazol-6-ol binding levels in superficial gray layers of human cortex was approximately 40% greater than binding observed with [$^{3}$H]PIB (p=0.0033, t=4.13; Student's t-test). This difference was attributed to the substantially reduced levels of nonspecific binding observed in [N-methyl-$^{3}$H$_{3}$]-2-(6-methylamino-pyridin-3-yl)-benzothiazol-6-ol labeled tissues compared to those exposed to [$^{3}$H]PIB. Further analysis of labeling in superficial cortical layers of tissue treated with or without PIB revealed large differences between [N-methyl-$^{3}$H$_{3}$]-2-(6-methylamino-pyridin-3-yl)-benzothiazol-6-ol and [$^{3}$H]PIB in the ratio of total binding compared to nonspecific binding ([N-methyl-$^{3}$H$_{3}$]-2-(6-methylamino-pyridin-3-yl)-benzothiazol-6-ol; 10.78:1 vs PIB; 2.48:1). A representative example of [N-methyl-$^{3}$H$_{3}$]-2-(6-methylamino-pyridin-3-yl)-benzothiazol-6-ol (right hand pictures) and [$^{3}$H]PIB (left hand pictures) binding of amyloid plaques in human AD brain (upper pictures), and of APP/PS1 transgenic mice brain (lower pictures), is shown in FIG. 5.

Biological Example 4

Binding of [$^{3}$H]AZAD in APP/PS1 Mouse Brain After Compound Administration In Vivo The in vivo binding properties of [$^{3}$H]AZAD, a compound of the present invention (example 32), was explored in this example with special relevance to PET imaging methods in a transgenic mouse model (APP/PS1) engineered to overproduce human amyloid-β.

In one experiment the in vivo properties of [$^3$H]AZAD were directly compared with those of [$^3$H]PIB: After administration, followed by decapitation 20 minutes thereafter, both [$^3$H]AZAD and [$^3$H]PIB labeled cortical structures (FIG. 6), which based on their size and distribution resemble the appearance of amyloid plaques labeled immunohistochemically with amyloid-D antibodies (Klunk et al. J. Neurosci. 2005, 25, 10598). Background binding levels (quantified in FIG. 7), especially in white matter tracts such as the corpus callosum and anterior commissure, but also in regions composed primarily of gray matter such as the striatum were more heavily labeled with [$^3$H]PIB than with [$^3$H]AZAD in rinsed as well as in unrinsed tissue. In brain areas rich in gray matter such as the striatum, nonspecific binding was generally lower than in white matter regions for both compounds, and in unrinsed tissue, did not differ significantly between the compounds. However, while nonspecific binding was not significantly reduced in rinsed tissues from mice given [$^3$H]PIB in brain areas rich in gray matter (striatum), the in vitro rinse procedure did reduce nonspecific [$^3$H]AZAD binding by 78.5% (Ligand×Rinse interaction: p<0.0001; df=1.6; F=72.72). In white matter regions, exemplified by the corpus callosum, nonspecific [$^3$H]PIB binding was higher than that of [$^3$H]AZAD regardless of rinse condition. Furthermore, while the in vitro rinse was only marginally effective in corpus callosum from mice given [$^3$H]PIB, it dramatically reduced [$^3$H]AZAD levels in corpus callosum (ligand×rinse interaction: p<0.0001; df=1.6; F=107.8). The ratio of the cortical plaque labeling divided by the area of cortex measured for both [$^3$H]PIB and [$^3$H]AZAD on rinsed brain sections are shown in FIG. 8.

A second experiment focused on the timecourse of the uptake and clearance of [$^3$H]AZAD at timepoints relevant to [$^{11}$C]-PET imaging. Autoradiograms illustrating [$^3$H]AZAD binding in APP/PS1 transgenic mouse brain sections 20, 40 and 80 minutes after administration are shown in FIG. 9. One-way ANOVA of cortical plaque labeling in rinsed tissue at different exposure intervals (FIG. 10) showed that [$^3$H]AZAD binding was highest at 20 minutes and declined such that levels were barely detectable after 80 minutes (p=0.0424; df=2.5; F=10.84). In addition to [$^3$H]AZAD cortical plaque labeling, total radioactivity levels in plaque free regions were compared to provide a measure of nonspecific labeling (FIG. 11). Two-way ANOVA of total radioactivity levels at is different exposure intervals showed that levels decreased significantly as the duration of exposure increased (main effect of exposure duration, p=0.0063; df=2.6; F=13.26)

Biological Example 5

PET Studies in Monkey

The time course of total brain radioactivity reflects the availability of the ligand in the target organ. For reference radioligands, e.g. [$^{11}$C]raclopride, the fraction of the total injected radioactivity present in the brain during the first 5-10 min is usually above 1-2%. [$^{11}$C]AZAD rapidly entered brain and the exposure was about 1-3% of total injected radioactivity (FIG. 12). Brain uptake of [$^{11}$C]AZAD peaked in the first minute after injection surpassing that of [$^{11}$C]PIB at this early time point. Brain concentration of [$^{11}$C]AZAD thereafter declined rapidly with lower concentrations as compared to [$^{11}$C]PIB at all time points. Because of lack of specific binding sites, i.e. amyloid plaques, in the studied monkeys in this example, no comparison could be made between [$^{11}$C]AZAD and [$^{11}$C]PIB with regard to their in vivo binding characteristics to such plaques. The brain uptake in this experiment is, however, illustrative of and reflects unspecific binding (FIG. 13). Taken together, these findings support that [$^{11}$C]AZAD enters brain tissue in primates and has significantly lower unspecific binding as compared to [$^{11}$C]PIB at time points of relevance for PET-detection of amyloid plaques. Whole body PET measurements were performed to investigate and compare the peripheral distribution and elimination routes of [$^{11}$C]AZAD and [$^{11}$C]PIB. As can be seen in FIGS. 14 and 15, the two ligands have similar elimination routes consisting of urinary excretion and hepatobiliary secretion. 1 hour post administration, most of the radioactivity was localized in the bladder and gastroenteral tract. Accumulation in other organs, e.g. lungs or bone marrow, was very low. [$^{11}$C]AZAD had faster elimination and lower non-eliminatory (e.g. lung) disposition as compared to [$^{11}$C]PIB. These results indicate a favourable radiation safety of [$^{11}$C]AZAD.

Figure 1:
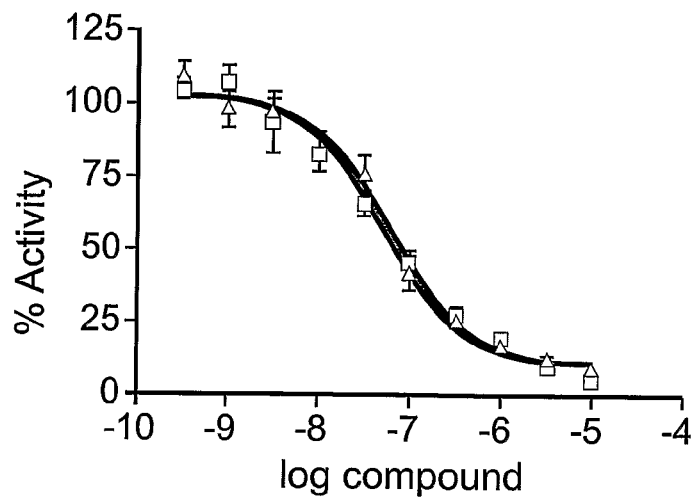
FIG. 1. Activity ("% Activity") of remaining [$^3$H]PIB versus increasing concentration of non-labeled compounds ("log compound") of the present invention (square: 2-[6-(methylamino)pyridin-3-yl]-1,3-benzothiazol-6-ol [ex. 27]; triangle: 5-(6-methoxy-1,3-benzothiazol-2-yl)-N-methylpyridin-2-amine [example 25]) in the competition binding assay.
Figure 2:
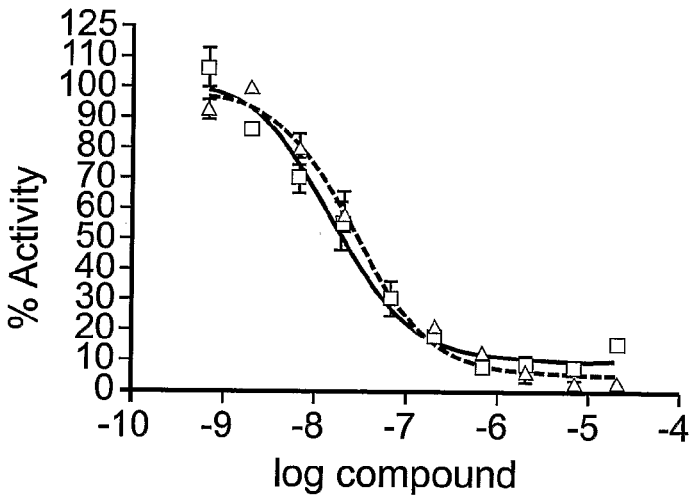
FIG. 2. Activity ("% Activity") of remaining [N-methyl-3H$_3$]-2-(6-methylamino-pyridin-3-yl)-benzothiazol-6-ol (example 32) versus increasing concentration ("log compound") of a non-labeled compound of the present invention (triangle: 2-[6-(methylamino)pyridin-3-yl]-1,3-benzothiazol-6-ol [example 27]), and PIB (squares) in the competition binding assay.
Figure 3:
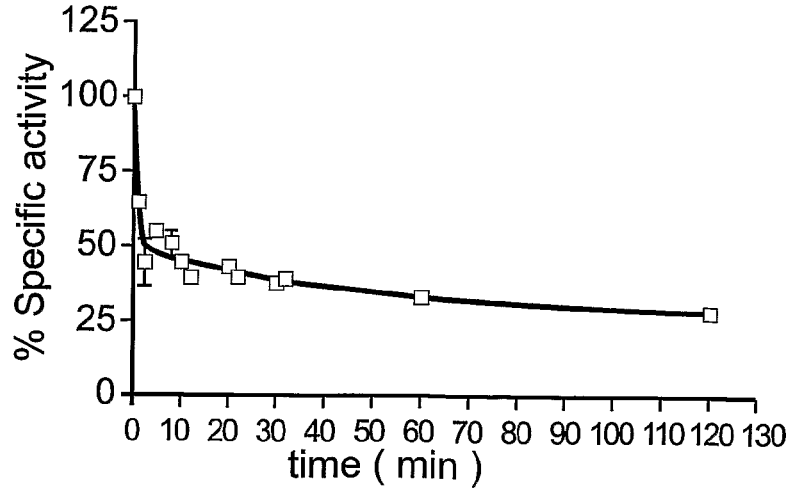
FIG. 3. Example of a dissociation experiment: Dissociation of [N-methyl-3H$_3$]-2-(6-methylamino-pyridin-3-yl)-benzothiazol-6-ol (example 32) from Aβ1-40 fibrils over time.
Figure 4A:
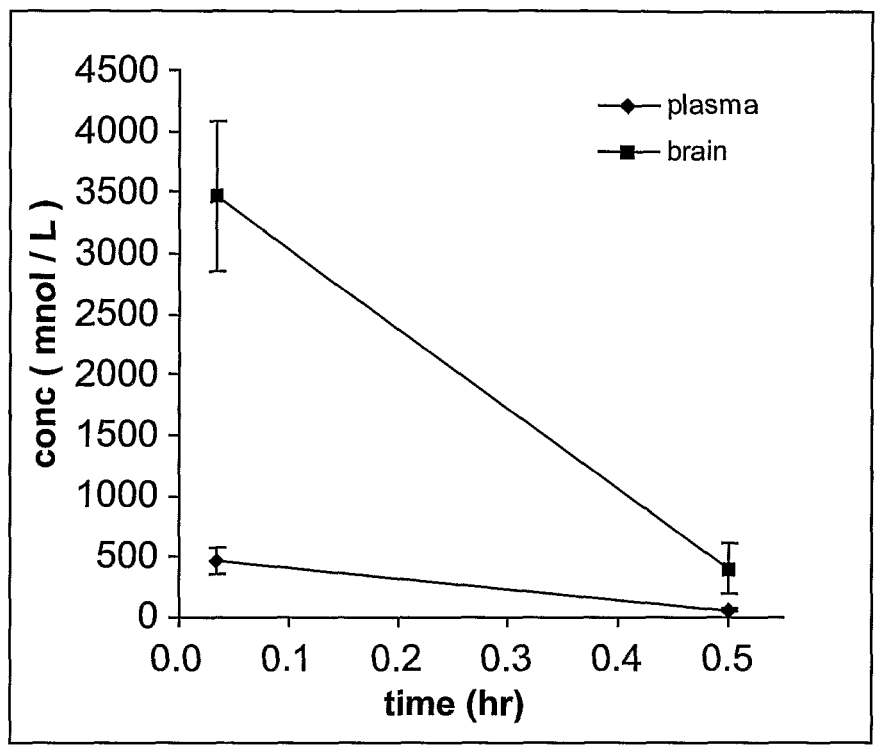
FIG. 4. Brain and plasma concentration at 2 and 30 minutes after i.v. administration in rat of PIB (upper graph "A"), and 2-[6-(methylamino)pyridin-3-yl]-1,3-benzothiazol-6-ol (lower graph "B"), a compound of the present intervention (example 27).
Figure 4B:
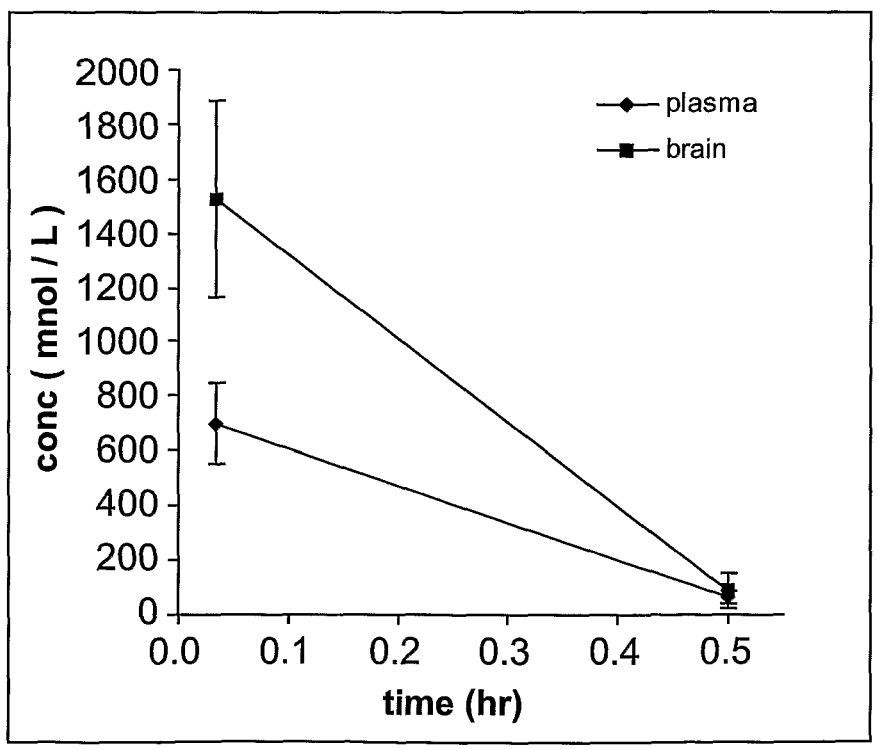
Figure 5:
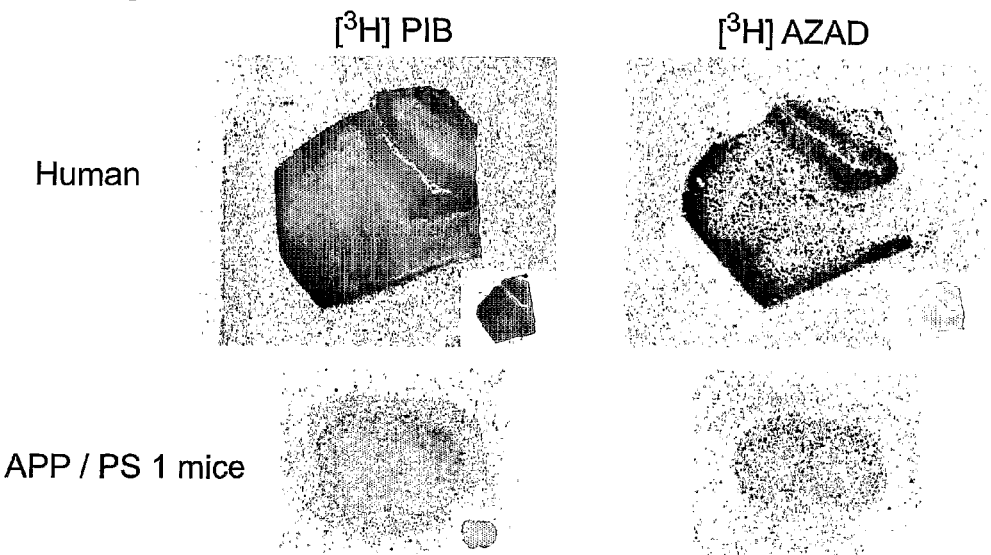
FIG. 5. Example of amyloid binding post mortem in human brain tissue section (upper) and APP/PS1 mice brain slice (lower), using [$^3$H]PIB (left) and [N-methyl-3H$_3$]-2-(6-methylamino-pyridin-3-yl)-benzothiazol-6-ol (right), a novel compound of the present intervention, for staining. The inserted panels shows the binding in the presence of 1 μM PIB.
Figure 6:
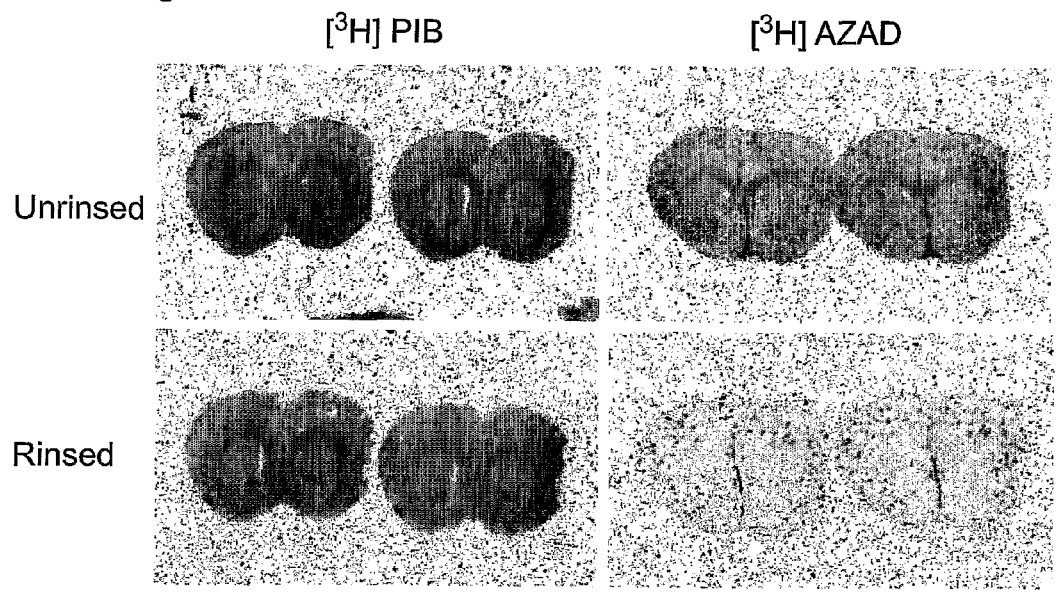
FIG. 6. Autoradiograms illustrating labeling after in vivo administration of [$^3$H]PIB (left pictures) and [$^3$H]AZAD (right pictures) in brain sections from APP/PS1 mice. The brain sections were either unrinsed (upper pictures) or rinsed (lower pictures).
Figure 7A:
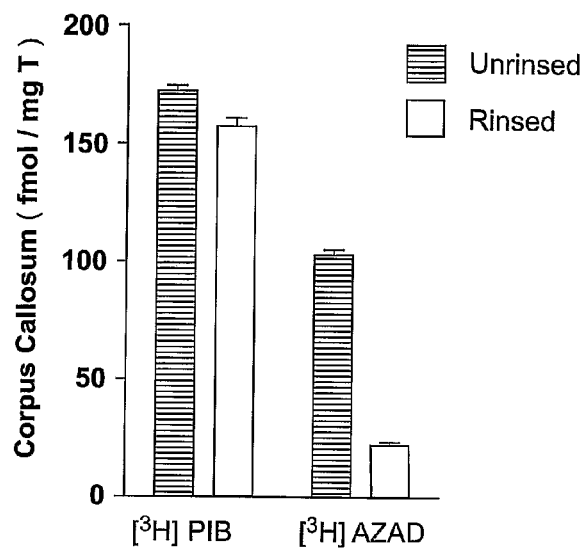
FIG. 7. Quantitative comparison of nonspecific binding between [$^3$H]PIB and [$^3$H]AZAD, A; white matter regions (Corpus Callosum), and B; in gray matter regions (Striatum).
Figure 7B:
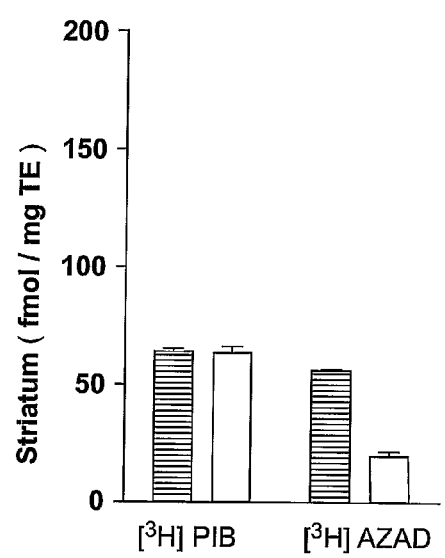
Figure 8:
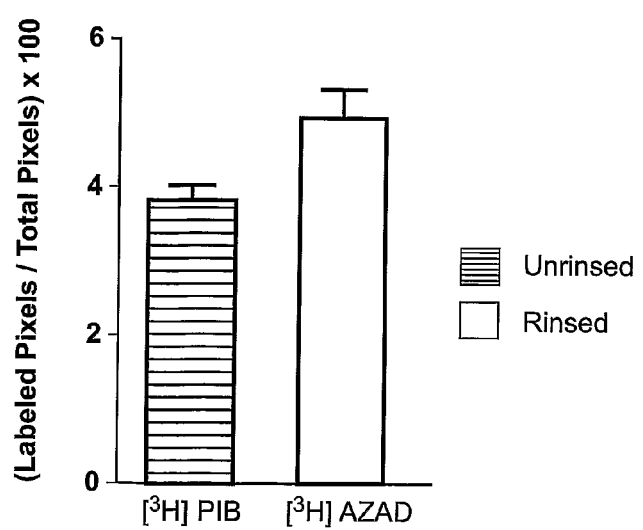
FIG. 8. Cortical plaque-load analysis. Data are expressed as a ratio of the cortical [$^3$H]AZAD plaque labeling divided by the area of cortex measured.
Figure 9:
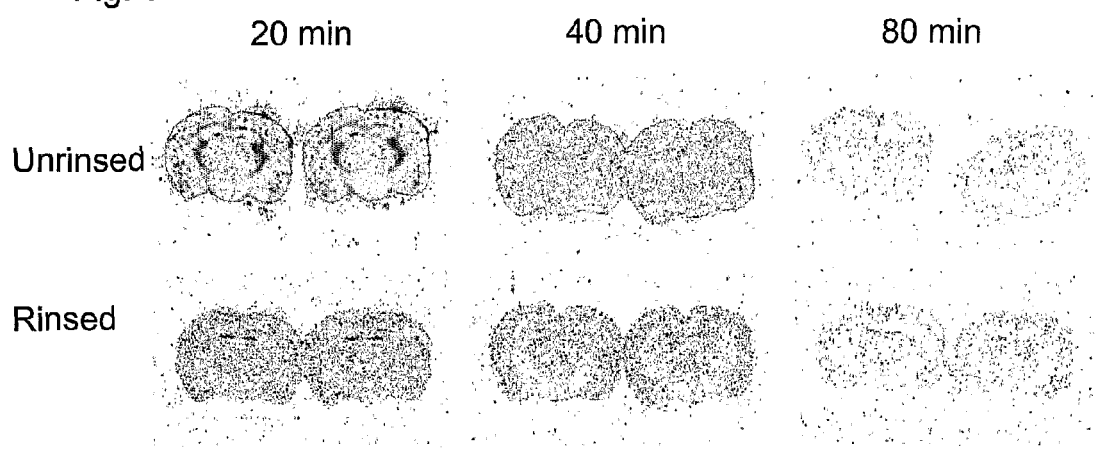
FIG. 9. Autoradiograms illustrating binding in rinsed and unrinsed sections at different exposure intervals after [$^3$H]AZAD administration in vivo.
Figure 10:
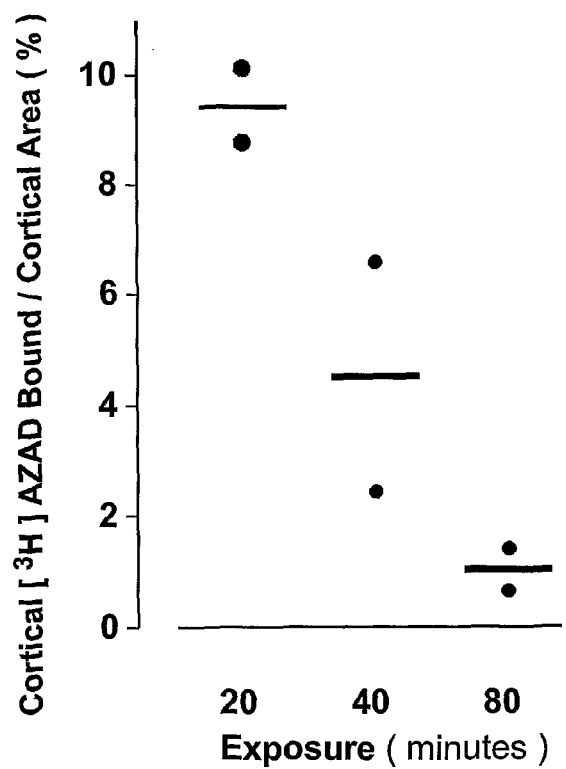
FIG. 10. Quantitative comparison of cortical plaque labelling with [$^3$H]AZAD after different exposure intervals in sections rinsed in vitro.
Figure 11:
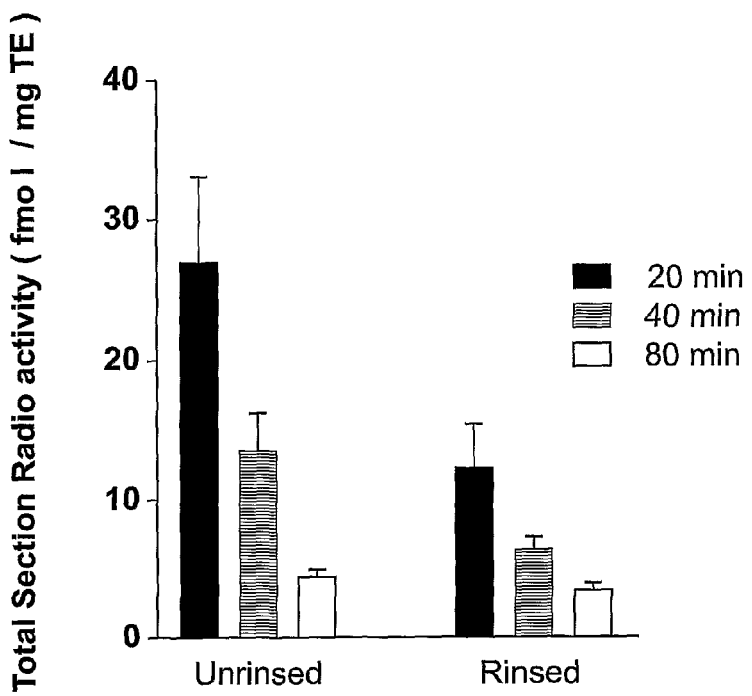
FIG. 11. Analysis of total radioactivity levels in rinsed and unrinsed sections collected from animals exposed in vivo to [$^3$H]AZAD for 20, 40 or 80 minutes.
Figure 12:
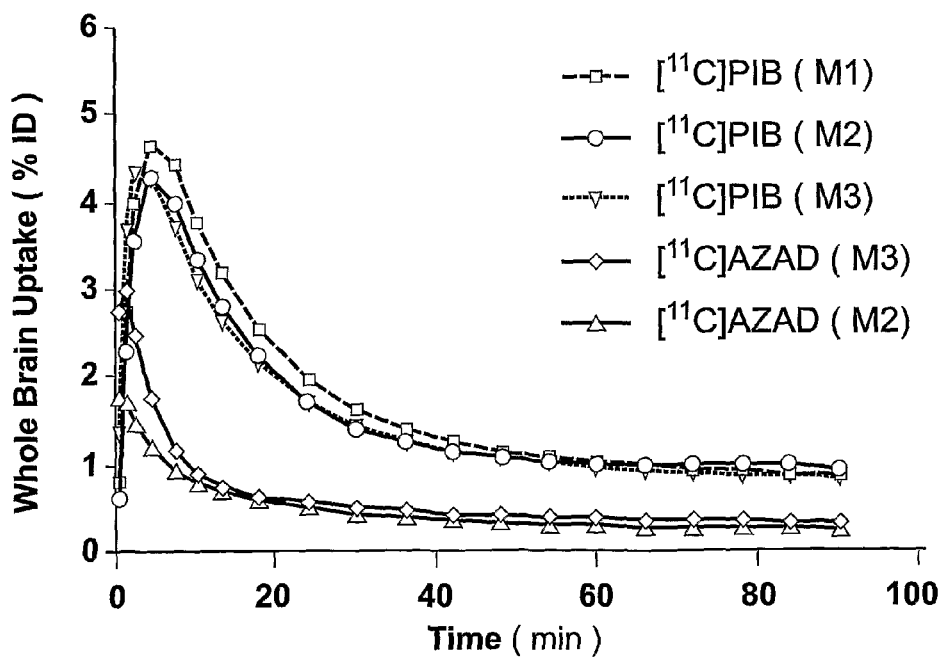
FIG. 12. Time course of brain uptake in monkey brain after administration of [$^{11}$C]AZAD and [$^{11}$C]PIB (MX means monkey X, where X is an integer each individual monkey has been assigned).
Figure 13:
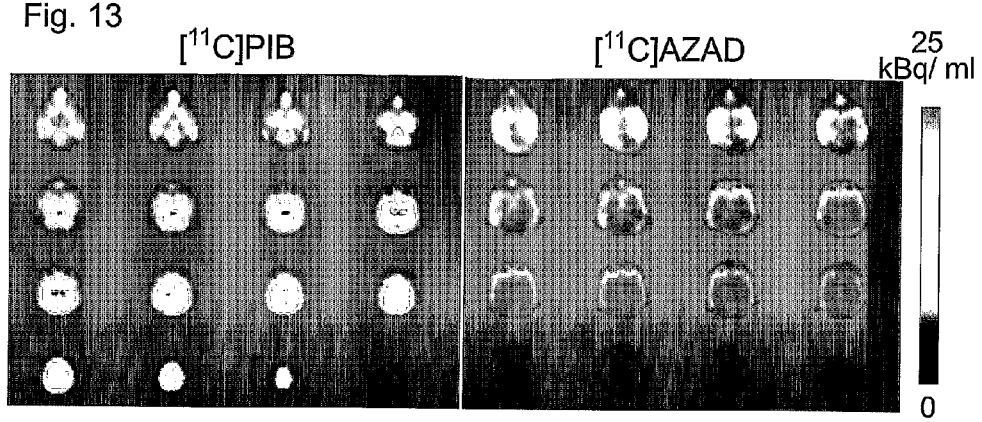
FIG. 13. Colour-coded PET images (summation images, 9-93 minutes) showing distribution of radioactivity in monkey brain after administration of [$^{11}$C]AZAD and [$^{11}$C]PIB.
Figure 14:
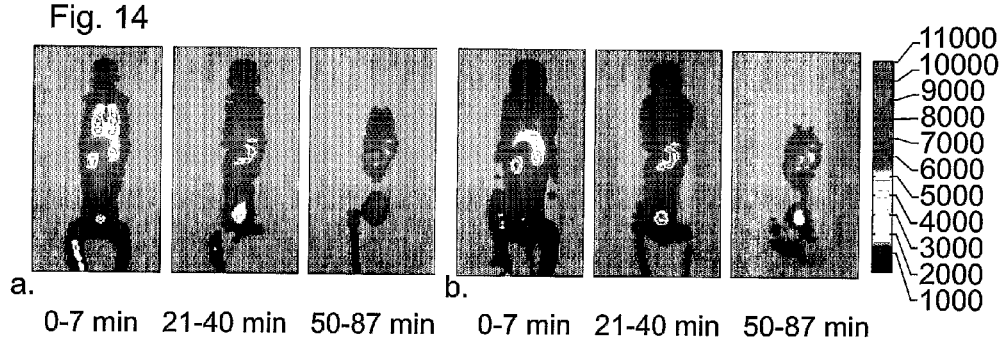
FIG. 14. Colour coded PET images showing radioactivity exposure in monkey whole body (coronal maximum intensity projections, decay uncorrected data) after injection of a: [$^{11}$C]PIB, b: [$^{11}$C]AZAD.
Figure 15:
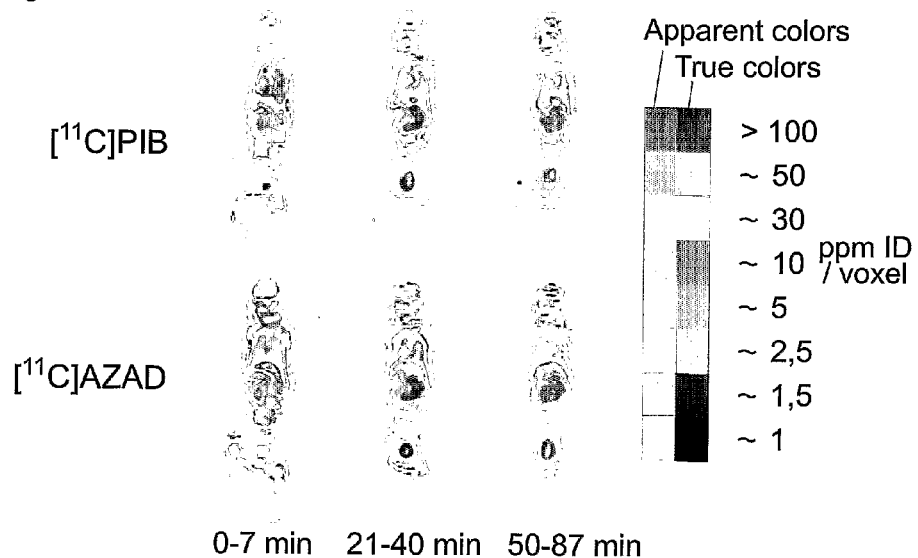
FIG. 15. Biodistribution of [$^{11}$C]PIB and [$^{11}$C]AZAD in monkey whole body (three-dimensional, left-oblique anterior view of parts-per-million injected dose images, decay corrected data). "ppm ID/voxel" denotes parts per million of injected (radioactivity) dose per voxel (decay corrected data).

The invention claimed is:

1. An optionally radiolabelled compound or salt thereof, wherein the compound corresponds to:

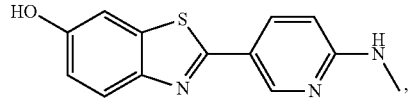

wherein:
one or more of the atoms is optionally replaced with a detectable isotope.

2. The compound or salt thereof according to claim 1, wherein:
one to three of the atoms is/are a detectable isotope selected from $^3$H, $^{19}$F, and $^{13}$C; or
one of the atoms is a detectable isotope selected from $^{18}$F, $^{11}$C, and $^{14}$C.

3. The compound or salt thereof according to claim 1, wherein one or more of the atoms is/are a detectable isotope selected from $^3$H, $^{18}$F, $^{19}$F, $^{11}$C, $^{13}$C, $^{14}$C, $^{75}$Br, $^{76}$Br, $^{120}$I, $^{123}$I, $^{125}$I, and $^{131}$I.

4. The compound or salt thereof according to claim 3, wherein:
one atom is a detectable isotope, and
the detectable isotope is selected from $^{18}$F and $^{11}$C.

5. The compound or salt thereof according to claim 4, wherein the compound corresponds to:

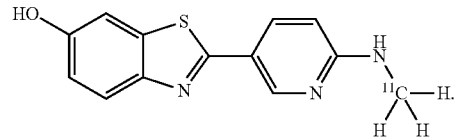

6. A compound, wherein the compound corresponds to:

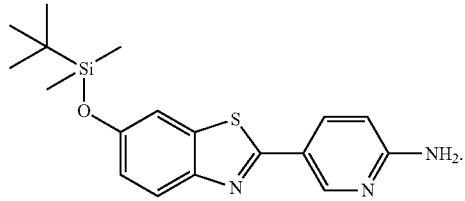

7. A pharmaceutical composition, wherein the composition comprises:
a compound or salt thereof according to claim 1, and
a pharmaceutically acceptable carrier.

8. A pharmaceutical composition for in vivo imaging of amyloid deposits, wherein the composition comprises:
a compound or salt thereof according to claim 3, and
a pharmaceutically acceptable carrier.

9. A pharmaceutical composition for in vivo imaging of amyloid deposits, wherein the composition comprises:
a compound or salt thereof according to claim 4, and
a pharmaceutically acceptable carrier.

10. A pharmaceutical composition for in vivo imaging of amyloid deposits, wherein the composition comprises:
a compound or salt thereof according to claim 5, and
a pharmaceutically acceptable carrier.

* * * * *